(12) United States Patent
Erez et al.

(10) Patent No.: US 8,067,473 B2
(45) Date of Patent: Nov. 29, 2011

(54) METHODS FOR ENHANCING THE THERAPEUTIC EFFICACY OF TOPOISOMERASE INHIBITORS

(75) Inventors: Omri Erez, Rehovot (IL); Iris Alchanati, Raanana (IL); Philippe Nakache, Nes Ziona (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 390 days.

(21) Appl. No.: 12/009,310

(22) Filed: Jan. 16, 2008

(65) Prior Publication Data
US 2008/0227727 A1 Sep. 18, 2008

Related U.S. Application Data

(60) Provisional application No. 61/005,636, filed on Dec. 5, 2007, provisional application No. 60/880,775, filed on Jan. 16, 2007.

(51) Int. Cl.
*A01N 43/40* (2006.01)
*A01N 43/42* (2006.01)
*A01N 29/04* (2006.01)
*A61K 31/44* (2006.01)
*A61K 31/25* (2006.01)

(52) U.S. Cl. .......... 514/755; 514/277; 514/290; 546/79
(58) Field of Classification Search .................. 514/277, 514/290, 755; 546/79
See application file for complete search history.

(56) References Cited

U.S. PATENT DOCUMENTS
2004/0180889 A1* 9/2004 Suto et al. ................. 514/235.2

FOREIGN PATENT DOCUMENTS
WO WO 03/059290 7/2003
WO WO 2008/087643 7/2008

OTHER PUBLICATIONS

PCT International Search Report issued Dec. 23, 2008 in connection with PCT/IL2008/000073, filed Jan. 16, 2008.
Fickentscher, Kurt et al. (1980) "Synthesis and Teratogenic . . . Indane-1,3-diones" Archiv Der Pharmazie (Weinheim, Germany) 313(6), 481-7 (including English-language abstract).
Written Opinion of International Searching Authority issued on Jul. 16, 2009 in connection with PCT/IL2008/000073, filed on Jan. 16, 2008.
PCT International Preliminary Report on Patentability issued on Jul. 21, 2009 in connection with PCT/IL2008/000073, filed on Jan. 16, 2008.
Gurrieri, C., et al. (2004) "Loss of the tumor suppressor PML in human cancers of multiple histologic origins." J Natl Cancer Inst. 96(4):269-79.
Berezovska, O.P., et al. (2006) "Essential role for activation of the Polycomb group (PcG) protein chromatin silencing pathway in metastatic prostate cancer." Cell Cycle, 5:1886-901 (Exhibit 1).
Cao, R., et al. (2005) "Role of Bmi-1 and Ring1A in H2A ubiquitylation and HOX gene silencing." Mol. Cell, 20:845-54 (Exhibit 2).
de Napoles, M., et al., (2004) "Polycomb group proteins Ring1A/B link ubiquitylation of histone H2A to heritable gene silencing and X inactivation." Dev. Cell, 7:663-76 (Exhibit 3).
Fang, J., et al., (2004) "Ring1b-mediated H2A ubiquitination associates with inactive X chromosomes and is involved in initiation of X inactivation." J Biol. Chem., 279:52812-5 (Exhibit 4).
Gambacorta, M., et al. (1996) "Heterogeneous nuclear expression of the promyelocytic leukemia (PML) protein in normal and neoplastic human tissues." Am. J Pathol., 149(6):2023-35 (Exhibit 5).
He, D., et al. (1997) "Adenovirus-mediated expression of PML suppresses growth and tumorigenicity of prostate cancer cells." Cancer Res., 57(10):1868-72 (Exhibit 6).
He, D., et al. (2003) "Overexpression of the promyelocytic leukemia gene suppresses growth of human bladder cancer cells by inducing G1 cell cycle arrest and apoptosis." Chin. Med. J (Engl), 116(9):1394-8 (Exhibit 7).
Hernandez-Munoz, I., et al., (2005) "Stable X chromosome inactivation involves the PRC1 Polycomb complex and requires histone MACROH2A1 and the CULLIN3/SPOP ubiquitin E3 ligase." PNAS, 102:7635-40 (Exhibit 8).
Koken, M.H., et al. (1995) "The PML growth-suppressor has an altered expression in human oncogenesis." Oncogene, 10(7):1315-24, (Abstract Only), (Exhibit 9).
Le, X.F., et al. (1998) "Recombinant PML adenovirus suppresses growth and tumorigenicity of human breast cancer cells by inducing G1 cell cycle arrest and apoptosis." Oncogene, 16(14):1839-49 (Exhibit 10).
Liu, L. et al., (2006) "Loss of the human polycomb group protein BMI1 promotes cancer-specific cell death." Oncogene, 25:4370-5 (Exhibit 11).
Melnick, A. and J.D. Licht, (1999) "Deconstructing a disease: RARalpha, its fusion partners, and their roles in the pathogenesis of acute promyelocytic leukemia." Blood, 93(10):3167-215 (Exhibit 12). Piazza, F. et al. (2001) "The theory of APL." Oncogene, 20(49):7216-22 (Exhibit 13).
Sasaki, M., et al., (2006) "Decreased expression of Bmi1 is closely associated with cellular senescence in small bile ducts in primary biliary cirrhosis." Am. J Pathol., 169:831-45 (Exhibit 14).
Son, S.H., et al. (2004) "Promyelocytic leukemia protein-induced growth suppression and cell death in liver cancer cells." Cancer Gene Ther., 5:5 (Exhibit 15).
Wang, H., et al. (2004) "Role of histone H2A ubiquitination in Polycomb silencing." Nature, 431:873-8 (Exhibit 16).
Wei, J. et al. (2006) "Role of Bmi1 in H2A ubiquitylation and Hox gene silencing." J Biol. Chem., 21:22537-44 (Exhibit 17).
Yu, J.H., et al. (2004) "Restoration of promyelocytic leukemia protein-nuclear bodies in neuroblastoma cells enhances retinoic acid responsiveness." Cancer Res., 64(3):928-33 (Exhibit 18); and.
Zhang, P., et al. (2000) "Lack of expression for the suppressor PML in human small cell lung carcinoma." Int. J Cancer, 85(5):599-605 (Exhibit 19).

* cited by examiner

*Primary Examiner* — Sreeni Padmanabhan
*Assistant Examiner* — Kendra D Carter
(74) *Attorney, Agent, or Firm* — John P. White; Cooper & Dunham LLP

(57) ABSTRACT

Disclosed are methods and compositions useful in identifying an E3 ubiquitin ligase inhibitor and modulating cell growth, comprising contacting a cell with an effective amount of an inhibitor of an E3 ubiquitin ligase, and contacting the cell with an effective amount of a topoisomerase inhibitor, wherein the treatment with the E3 ubiquitin ligase inhibitor and topoisomerase inhibitor modulates cell growth in comparison to a cell treated with the topoisomerase inhibitor alone. The present invention further provides methods for identifying and making an E3 ubiquitin ligase inhibitor.

12 Claims, 15 Drawing Sheets

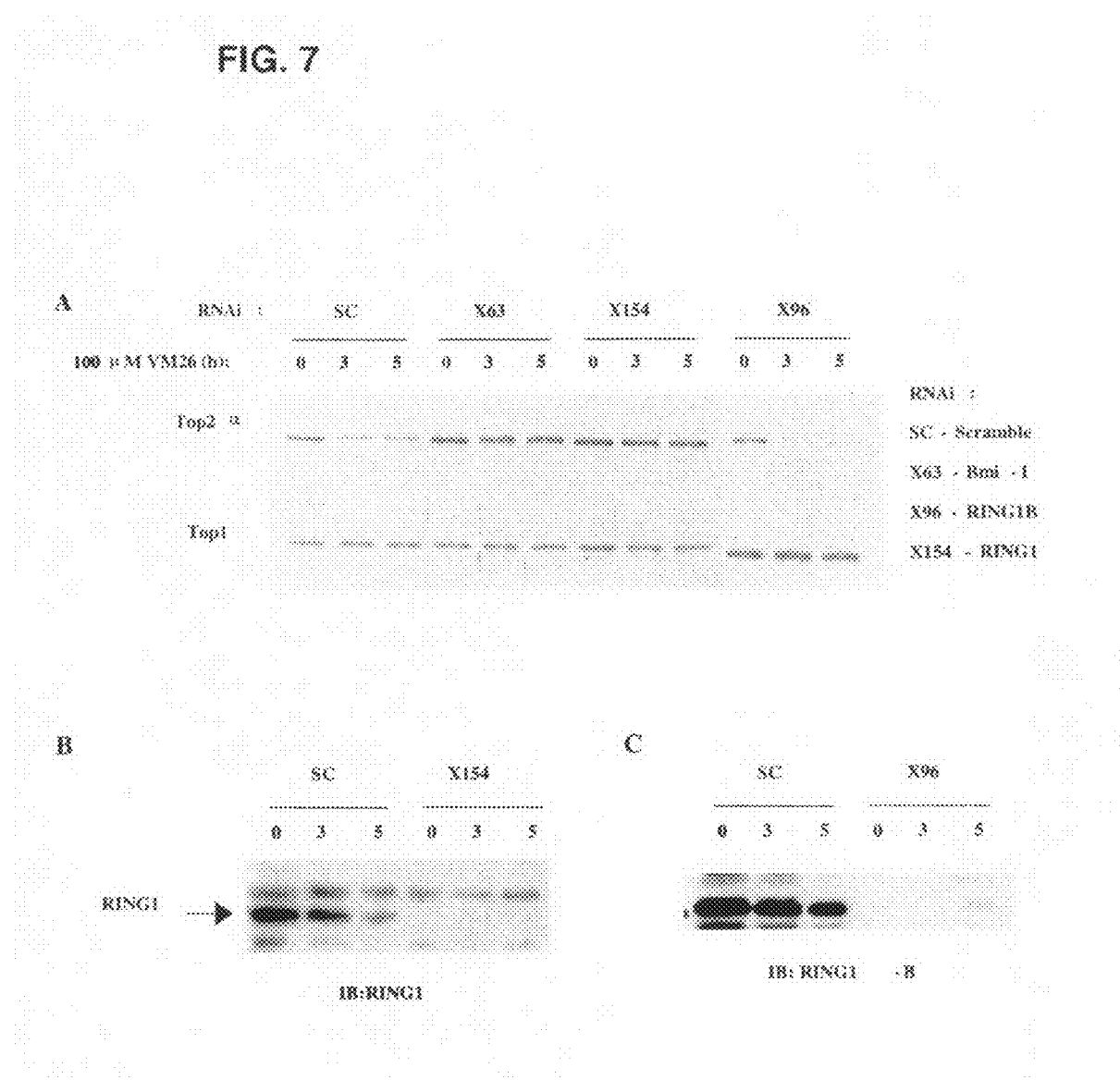

SEQUENCE LISTING

```
<160> NUMBER OF SEQ ID NOS: 348

<210> SEQ ID NO 1
<211> LENGTH: 21
<212> TYPE: DNA
<213> ORGANISM: Human

<400> SEQUENCE: 1
tgctcccacc aaggatccaa a                                              21
```

<210> SEQ ID NO 2
<211> LENGTH: 25
<212> TYPE: DNA
<213> ORGANISM: Human

<400> SEQUENCE: 2
ctcccaccaa ggatccaaag tgacc                                              25

<210> SEQ ID NO 3
<211> LENGTH: 27
<212> TYPE: RNA
<213> ORGANISM: Artificial Sequence
<220> FEATURE:
<223> OTHER INFORMATION: Antisense

<400> SEQUENCE: 3
augggucauc agcaacuucu ucudgdg                                            27

<210> SEQ ID NO 4
<211> LENGTH: 27
<212> TYPE: RNA
<213> ORGANISM: Artificial
<220> FEATURE:
<223> OTHER INFORMATION: Antisense

<400> SEQUENCE: 4
ccagaagaag uugcugauga cccauuu                                            27

<210> SEQ ID NO 5
<211> LENGTH: 27
<212> TYPE: RNA
<213> ORGANISM: Artificial
<220> FEATURE:
<223> OTHER INFORMATION: Antisense

<400> SEQUENCE: 5
aacucuccaa gauauuguau acadada                                            27

<210> SEQ ID NO 6
<211> LENGTH: 27
<212> TYPE: RNA
<213> ORGANISM: Artificial
<220> FEATURE:
<223> OTHER INFORMATION: Antisense

<400> SEQUENCE: 6
uuuguauaca auaucuugga gaguuuu                                            27

<210> SEQ ID NO 7
<211> LENGTH: 27
<212> TYPE: RNA
<213> ORGANISM: Artificial
<220> FEATURE:
<223> OTHER INFORMATION: Antisense

<400> SEQUENCE: 7
cugcauuguc acagcccuac ggadgdc                                            27

<210> SEQ ID NO 8
<211> LENGTH: 27
<212> TYPE: RNA
<213> ORGANISM: Artificial
<220> FEATURE:
<223> OTHER INFORMATION: Antisense

<400> SEQUENCE: 8

```
gcuccguagg gcugugacaa ugcaguu                                              27

<210> SEQ ID NO 9
<211> LENGTH: 27
<212> TYPE: RNA
<213> ORGANISM: Artificial
<220> FEATURE:
<223> OTHER INFORMATION: Antisense

<400> SEQUENCE: 9
agaucuaucc uagccgggag gaaduda                                              27

<210> SEQ ID NO 10
<211> LENGTH: 27
<212> TYPE: RNA
<213> ORGANISM: Artificial
<220> FEATURE:
<223> OTHER INFORMATION: Antisense

<400> SEQUENCE: 10
uauuccuccc ggcuaggaua gaucuuu                                              27

<210> SEQ ID NO 11
<211> LENGTH: 27
<212> TYPE: RNA
<213> ORGANISM: Artificial
<220> FEATURE:
<223> OTHER INFORMATION: Antisense

<400> SEQUENCE: 11
gcacaaauga gccuuuaaaa accdada                                              27

<210> SEQ ID NO 12
<211> LENGTH: 27
<212> TYPE: RNA
<213> ORGANISM: Artificial
<220> FEATURE:
<223> OTHER INFORMATION: Antisense

<400> SEQUENCE: 12
uugguuuuua aaggcucauu ugugcuu                                              27

<210> SEQ ID NO 13
<211> LENGTH: 21
<212> TYPE: DNA
<213> ORGANISM: Human

<400> SEQUENCE: 13
aaatgcatcg aacaacgaga a                                                    21

<210> SEQ ID NO 14
<211> LENGTH: 25
<212> TYPE: DNA
<213> ORGANISM: Human

<400> SEQUENCE: 14
atgcatcgaa caacgagaat caaga                                                25

<210> SEQ ID NO 15
<211> LENGTH: 21
<212> TYPE: DNA
<213> ORGANISM: Human

<400> SEQUENCE: 15
gtgtattgtt cgttacctgg a                                                    21
```

```
<210> SEQ ID NO 16
<211> LENGTH: 25
<212> TYPE: DNA
<213> ORGANISM: Human

<400> SEQUENCE: 16
gtattgttcg ttacctggag accag                                        25

<210> SEQ ID NO 17
<211> LENGTH: 21
<212> TYPE: DNA
<213> ORGANISM: Human

<400> SEQUENCE: 17
tgtattgttc gttacctgga g                                            21

<210> SEQ ID NO 18
<211> LENGTH: 25
<212> TYPE: DNA
<213> ORGANISM: Human

<400> SEQUENCE: 18
tattgttcgt tacctggaga ccagc                                        25

<210> SEQ ID NO 19
<211> LENGTH: 21
<212> TYPE: DNA
<213> ORGANISM: Human

<400> SEQUENCE: 19
gtattgttcg ttacctggag a                                            21

<210> SEQ ID NO 20
<211> LENGTH: 25
<212> TYPE: DNA
<213> ORGANISM: Human

<400> SEQUENCE: 20
attgttcgtt acctggagac cagca                                        25

<210> SEQ ID NO 21
<211> LENGTH: 21
<212> TYPE: DNA
<213> ORGANISM: Human

<400> SEQUENCE: 21
attgttcgtt acctggagac c                                            21

<210> SEQ ID NO 22
<211> LENGTH: 25
<212> TYPE: DNA
<213> ORGANISM: Human

<400> SEQUENCE: 22
tgttcgttac ctggagacca gcaag                                        25

<210> SEQ ID NO 23
<211> LENGTH: 21
<212> TYPE: DNA
<213> ORGANISM: Human

<400> SEQUENCE: 23
tgttcgttac ctggagacca g                                            21
```

```
<210> SEQ ID NO 24
<211> LENGTH: 25
<212> TYPE: DNA
<213> ORGANISM: Human

<400> SEQUENCE: 24
ttcgttacct ggagaccagc aagta                                            25

<210> SEQ ID NO 25
<211> LENGTH: 21
<212> TYPE: DNA
<213> ORGANISM: Human

<400> SEQUENCE: 25
cagcaagtat tgtcctattt g                                                21

<210> SEQ ID NO 26
<211> LENGTH: 25
<212> TYPE: DNA
<213> ORGANISM: Human

<400> SEQUENCE: 26
gcaagtattg tcctatttgt gatgt                                            25

<210> SEQ ID NO 27
<211> LENGTH: 21
<212> TYPE: DNA
<213> ORGANISM: Human

<400> SEQUENCE: 27
tatttgtgat gtccaagttc a                                                21

<210> SEQ ID NO 28
<211> LENGTH: 25
<212> TYPE: DNA
<213> ORGANISM: Human

<400> SEQUENCE: 28
tttgtgatgt ccaagttcac aagac                                            25

<210> SEQ ID NO 29
<211> LENGTH: 21
<212> TYPE: DNA
<213> ORGANISM: Human

<400> SEQUENCE: 29
atttgtgatg tccaagttca c                                                21

<210> SEQ ID NO 30
<211> LENGTH: 25
<212> TYPE: DNA
<213> ORGANISM: Human

<400> SEQUENCE: 30
ttgtgatgtc caagttcaca agacc                                            25

<210> SEQ ID NO 31
<211> LENGTH: 21
<212> TYPE: DNA
<213> ORGANISM: Human

<400> SEQUENCE: 31
tttgtgatgt ccaagttcac a                                                21
```

-continued

```
<210> SEQ ID NO 32
<211> LENGTH: 25
<212> TYPE: DNA
<213> ORGANISM: Human

<400> SEQUENCE: 32
tgtgatgtcc aagttcacaa gacca                                  25

<210> SEQ ID NO 33
<211> LENGTH: 21
<212> TYPE: DNA
<213> ORGANISM: Human

<400> SEQUENCE: 33
gtgatgtcca agttcacaag a                                      21

<210> SEQ ID NO 34
<211> LENGTH: 25
<212> TYPE: DNA
<213> ORGANISM: Human

<400> SEQUENCE: 34
gatgtccaag ttcacaagac cagac                                  25

<210> SEQ ID NO 35
<211> LENGTH: 21
<212> TYPE: DNA
<213> ORGANISM: Human

<400> SEQUENCE: 35
gagaatcaag atcactgagc t                                      21

<210> SEQ ID NO 36
<211> LENGTH: 25
<212> TYPE: DNA
<213> ORGANISM: Human

<400> SEQUENCE: 36
gaatcaagat cactgagcta aatcc                                  25

<210> SEQ ID NO 37
<211> LENGTH: 21
<212> TYPE: DNA
<213> ORGANISM: Human

<400> SEQUENCE: 37
gatgtccaag ttcacaagac c                                      21

<210> SEQ ID NO 38
<211> LENGTH: 25
<212> TYPE: DNA
<213> ORGANISM: Human

<400> SEQUENCE: 38
tgtccaagtt cacaagacca gacca                                  25

<210> SEQ ID NO 39
<211> LENGTH: 21
<212> TYPE: DNA
<213> ORGANISM: Human

<400> SEQUENCE: 39
agttcacaag accagaccac t                                      21
```

```
<210> SEQ ID NO 40
<211> LENGTH: 25
<212> TYPE: DNA
<213> ORGANISM: Human

<400> SEQUENCE: 40
ttcacaagac cagaccacta ctgaa                                          25

<210> SEQ ID NO 41
<211> LENGTH: 21
<212> TYPE: DNA
<213> ORGANISM: Human

<400> SEQUENCE: 41
gttcacaaga ccagaccact a                                              21

<210> SEQ ID NO 42
<211> LENGTH: 25
<212> TYPE: DNA
<213> ORGANISM: Human

<400> SEQUENCE: 42
tcacaagacc agaccactac tgaat                                          25

<210> SEQ ID NO 43
<211> LENGTH: 21
<212> TYPE: DNA
<213> ORGANISM: Human

<400> SEQUENCE: 43
ccactactga atataaggtc a                                              21

<210> SEQ ID NO 44
<211> LENGTH: 25
<212> TYPE: DNA
<213> ORGANISM: Human

<400> SEQUENCE: 44
actactgaat ataaggtcag ataaa                                          25

<210> SEQ ID NO 45
<211> LENGTH: 21
<212> TYPE: DNA
<213> ORGANISM: Human

<400> SEQUENCE: 45
aatgcatcga acaacgagaa t                                              21

<210> SEQ ID NO 46
<211> LENGTH: 25
<212> TYPE: DNA
<213> ORGANISM: Human

<400> SEQUENCE: 46
tgcatcgaac aacgagaatc aagat                                          25

<210> SEQ ID NO 47
<211> LENGTH: 21
<212> TYPE: DNA
<213> ORGANISM: Human

<400> SEQUENCE: 47
aaaactctcc aagatattgt a                                              21
```

```
<210> SEQ ID NO 48
<211> LENGTH: 25
<212> TYPE: DNA
<213> ORGANISM: Human

<400> SEQUENCE: 48
aactctccaa gatattgtat acaaa                                             25

<210> SEQ ID NO 49
<211> LENGTH: 21
<212> TYPE: DNA
<213> ORGANISM: Human

<400> SEQUENCE: 49
tacaaattag ttccagggct t                                                 21

<210> SEQ ID NO 50
<211> LENGTH: 25
<212> TYPE: DNA
<213> ORGANISM: Human

<400> SEQUENCE: 50
caaattagtt ccagggcttt tcaaa                                             25

<210> SEQ ID NO 51
<211> LENGTH: 21
<212> TYPE: DNA
<213> ORGANISM: Human

<400> SEQUENCE: 51
acaaattagt tccagggctt t                                                 21

<210> SEQ ID NO 52
<211> LENGTH: 25
<212> TYPE: DNA
<213> ORGANISM: Human

<400> SEQUENCE: 52
aaattagttc cagggctttt caaaa                                             25

<210> SEQ ID NO 53
<211> LENGTH: 21
<212> TYPE: DNA
<213> ORGANISM: Human

<400> SEQUENCE: 53
aaaatgaaat gaagagaaga a                                                 21

<210> SEQ ID NO 54
<211> LENGTH: 25
<212> TYPE: DNA
<213> ORGANISM: Human

<400> SEQUENCE: 54
aatgaaatga agagaagaag ggatt                                             25

<210> SEQ ID NO 55
<211> LENGTH: 21
<212> TYPE: DNA
<213> ORGANISM: Human

<400> SEQUENCE: 55
gcagctcatc cttctgctga t                                                 21
```

```
<210> SEQ ID NO 56
<211> LENGTH: 25
<212> TYPE: DNA
<213> ORGANISM: Human

<400> SEQUENCE: 56
agctcatcct tctgctgatg ctgcc                                              25

<210> SEQ ID NO 57
<211> LENGTH: 21
<212> TYPE: DNA
<213> ORGANISM: Human

<400> SEQUENCE: 57
atccttctgc tgatgctgcc a                                                  21

<210> SEQ ID NO 58
<211> LENGTH: 25
<212> TYPE: DNA
<213> ORGANISM: Human

<400> SEQUENCE: 58
ccttctgctg atgctgccaa tggct                                              25

<210> SEQ ID NO 59
<211> LENGTH: 21
<212> TYPE: DNA
<213> ORGANISM: Human

<400> SEQUENCE: 59
tccttctgct gatgctgcca a                                                  21

<210> SEQ ID NO 60
<211> LENGTH: 25
<212> TYPE: DNA
<213> ORGANISM: Human

<400> SEQUENCE: 60
cttctgctga tgctgccaat ggctc                                              25

<210> SEQ ID NO 61
<211> LENGTH: 21
<212> TYPE: DNA
<213> ORGANISM: Human

<400> SEQUENCE: 61
ttctgctgat gctgccaatg g                                                  21

<210> SEQ ID NO 62
<211> LENGTH: 25
<212> TYPE: DNA
<213> ORGANISM: Human

<400> SEQUENCE: 62
ctgctgatgc tgccaatggc tctaa                                              25

<210> SEQ ID NO 63
<211> LENGTH: 21
<212> TYPE: DNA
<213> ORGANISM: Human

<400> SEQUENCE: 63
tctgctgatg ctgccaatgg c                                                  21
```

-continued

<210> SEQ ID NO 64
<211> LENGTH: 25
<212> TYPE: DNA
<213> ORGANISM: Human

<400> SEQUENCE: 64
tgctgatgct gccaatggct ctaat                                          25

<210> SEQ ID NO 65
<211> LENGTH: 21
<212> TYPE: DNA
<213> ORGANISM: Human

<400> SEQUENCE: 65
gaagatagag gagaggttgc a                                              21

<210> SEQ ID NO 66
<211> LENGTH: 25
<212> TYPE: DNA
<213> ORGANISM: Human

<400> SEQUENCE: 66
agatagagga gaggttgcag atgaa                                          25

<210> SEQ ID NO 67
<211> LENGTH: 21
<212> TYPE: DNA
<213> ORGANISM: Human

<400> SEQUENCE: 67
gataataagc ttatccattg a                                              21

<210> SEQ ID NO 68
<211> LENGTH: 25
<212> TYPE: DNA
<213> ORGANISM: Human

<400> SEQUENCE: 68
taataagctt atccattgaa ttctt                                          25

<210> SEQ ID NO 69
<211> LENGTH: 21
<212> TYPE: DNA
<213> ORGANISM: Human

<400> SEQUENCE: 69
taagcttatc cattgaattc t                                              21

<210> SEQ ID NO 70
<211> LENGTH: 25
<212> TYPE: DNA
<213> ORGANISM: Human

<400> SEQUENCE: 70
agcttatcca ttgaattctt tgacc                                          25

<210> SEQ ID NO 71
<211> LENGTH: 21
<212> TYPE: DNA
<213> ORGANISM: Human

<400> SEQUENCE: 71
tgcatcgaac aacgagaatc a                                              21

```
<210> SEQ ID NO 72
<211> LENGTH: 25
<212> TYPE: DNA
<213> ORGANISM: Human

<400> SEQUENCE: 72
catcgaacaa cgagaatcaa gatca                                              25

<210> SEQ ID NO 73
<211> LENGTH: 21
<212> TYPE: DNA
<213> ORGANISM: Human

<400> SEQUENCE: 73
aacagattgg atcggaaagt a                                                  21

<210> SEQ ID NO 74
<211> LENGTH: 25
<212> TYPE: DNA
<213> ORGANISM: Human

<400> SEQUENCE: 74
cagattggat cggaaagtaa acaaa                                              25

<210> SEQ ID NO 75
<211> LENGTH: 21
<212> TYPE: DNA
<213> ORGANISM: Human

<400> SEQUENCE: 75
acagattgga tcggaaagta a                                                  21

<210> SEQ ID NO 76
<211> LENGTH: 25
<212> TYPE: DNA
<213> ORGANISM: Human

<400> SEQUENCE: 76
agattggatc ggaaagtaaa caaag                                              25

<210> SEQ ID NO 77
<211> LENGTH: 21
<212> TYPE: DNA
<213> ORGANISM: Human

<400> SEQUENCE: 77
cagattggat cggaaagtaa a                                                  21

<210> SEQ ID NO 78
<211> LENGTH: 25
<212> TYPE: DNA
<213> ORGANISM: Human

<400> SEQUENCE: 78
gattggatcg gaaagtaaac aaaga                                              25

<210> SEQ ID NO 79
<211> LENGTH: 21
<212> TYPE: DNA
<213> ORGANISM: Human

<400> SEQUENCE: 79
gattggatcg gaaagtaaac a                                                  21
```

```
<210> SEQ ID NO 80
<211> LENGTH: 25
<212> TYPE: DNA
<213> ORGANISM: Human

<400> SEQUENCE: 80
ttggatcgga agtaaacaa agaca                                          25

<210> SEQ ID NO 81
<211> LENGTH: 21
<212> TYPE: DNA
<213> ORGANISM: Human

<400> SEQUENCE: 81
attggatcgg aaagtaaaca a                                             21

<210> SEQ ID NO 82
<211> LENGTH: 25
<212> TYPE: DNA
<213> ORGANISM: Human

<400> SEQUENCE: 82
tggatcggaa agtaaacaaa gacaa                                         25

<210> SEQ ID NO 83
<211> LENGTH: 21
<212> TYPE: DNA
<213> ORGANISM: Human

<400> SEQUENCE: 83
ttggatcgga aagtaaacaa a                                             21

<210> SEQ ID NO 84
<211> LENGTH: 25
<212> TYPE: DNA
<213> ORGANISM: Human

<400> SEQUENCE: 84
ggatcggaaa gtaaacaaag acaaa                                         25

<210> SEQ ID NO 85
<211> LENGTH: 21
<212> TYPE: DNA
<213> ORGANISM: Human

<400> SEQUENCE: 85
gaaagtaaac aaagacaaag a                                             21

<210> SEQ ID NO 86
<211> LENGTH: 25
<212> TYPE: DNA
<213> ORGANISM: Human

<400> SEQUENCE: 86
aagtaaacaa agacaaagag aaatc                                         25

<210> SEQ ID NO 87
<211> LENGTH: 21
<212> TYPE: DNA
<213> ORGANISM: Human

<400> SEQUENCE: 87
aagtaaacaa agacaaagag a                                             21
```

```
<210> SEQ ID NO 88
<211> LENGTH: 25
<212> TYPE: DNA
<213> ORGANISM: Human

<400> SEQUENCE: 88
gtaaacaaag acaaagagaa atcta                                        25

<210> SEQ ID NO 89
<211> LENGTH: 21
<212> TYPE: DNA
<213> ORGANISM: Human

<400> SEQUENCE: 89
gtaaacaaag acaaagagaa a                                            21

<210> SEQ ID NO 90
<211> LENGTH: 25
<212> TYPE: DNA
<213> ORGANISM: Human

<400> SEQUENCE: 90
aaacaaagac aaagagaaat ctaag                                        25

<210> SEQ ID NO 91
<211> LENGTH: 21
<212> TYPE: DNA
<213> ORGANISM: Human

<400> SEQUENCE: 91
acaaagacaa agagaaatct a                                            21

<210> SEQ ID NO 92
<211> LENGTH: 25
<212> TYPE: DNA
<213> ORGANISM: Human

<400> SEQUENCE: 92
aaagacaaag agaaatctaa ggagg                                        25

<210> SEQ ID NO 93
<211> LENGTH: 21
<212> TYPE: DNA
<213> ORGANISM: Human

<400> SEQUENCE: 93
caaagacaaa gagaaatcta a                                            21

<210> SEQ ID NO 94
<211> LENGTH: 25
<212> TYPE: DNA
<213> ORGANISM: Human

<400> SEQUENCE: 94
aagacaaaga gaaatctaag gagga                                        25

<210> SEQ ID NO 95
<211> LENGTH: 21
<212> TYPE: DNA
<213> ORGANISM: Human

<400> SEQUENCE: 95
aaagacaaag agaaatctaa g                                            21
```

```
<210> SEQ ID NO 96
<211> LENGTH: 25
<212> TYPE: DNA
<213> ORGANISM: Human

<400> SEQUENCE: 96
agacaaagag aaatctaagg aggag                                  25

<210> SEQ ID NO 97
<211> LENGTH: 21
<212> TYPE: DNA
<213> ORGANISM: Human

<400> SEQUENCE: 97
agaaatctaa ggaggaggtg a                                      21

<210> SEQ ID NO 98
<211> LENGTH: 25
<212> TYPE: DNA
<213> ORGANISM: Human

<400> SEQUENCE: 98
aaatctaagg aggaggtgaa tgata                                  25

<210> SEQ ID NO 99
<211> LENGTH: 21
<212> TYPE: DNA
<213> ORGANISM: Human

<400> SEQUENCE: 99
gaaatctaag gaggaggtga a                                      21

<210> SEQ ID NO 100
<211> LENGTH: 25
<212> TYPE: DNA
<213> ORGANISM: Human

<400> SEQUENCE: 100
aatctaagga ggaggtgaat gataa                                  25

<210> SEQ ID NO 101
<211> LENGTH: 21
<212> TYPE: DNA
<213> ORGANISM: Human

<400> SEQUENCE: 101
taaaagatac ttacgatgcc c                                      21

<210> SEQ ID NO 102
<211> LENGTH: 25
<212> TYPE: DNA
<213> ORGANISM: Human

<400> SEQUENCE: 102
aaagatactt acgatgccca gcagc                                  25

<210> SEQ ID NO 103
<211> LENGTH: 21
<212> TYPE: DNA
<213> ORGANISM: Human

<400> SEQUENCE: 103
aaagatactt acgatgccca g                                      21
```

```
<210> SEQ ID NO 104
<211> LENGTH: 25
<212> TYPE: DNA
<213> ORGANISM: Human

<400> SEQUENCE: 104
agatacttac gatgcccagc agcaa                                    25

<210> SEQ ID NO 105
<211> LENGTH: 21
<212> TYPE: DNA
<213> ORGANISM: Human

<400> SEQUENCE: 105
agatacttac gatgcccagc a                                        21

<210> SEQ ID NO 106
<211> LENGTH: 25
<212> TYPE: DNA
<213> ORGANISM: Human

<400> SEQUENCE: 106
atacttacga tgcccagcag caatg                                    25

<210> SEQ ID NO 107
<211> LENGTH: 21
<212> TYPE: DNA
<213> ORGANISM: Human

<400> SEQUENCE: 107
gatacttacg atgcccagca g                                        21

<210> SEQ ID NO 108
<211> LENGTH: 25
<212> TYPE: DNA
<213> ORGANISM: Human

<400> SEQUENCE: 108
tacttacgat gcccagcagc aatga                                    25

<210> SEQ ID NO 109
<211> LENGTH: 21
<212> TYPE: DNA
<213> ORGANISM: Human

<400> SEQUENCE: 109
atgactgtga tgcacttaag a                                        21

<210> SEQ ID NO 110
<211> LENGTH: 25
<212> TYPE: DNA
<213> ORGANISM: Human

<400> SEQUENCE: 110
gactgtgatg cacttaagaa agttt                                    25

<210> SEQ ID NO 111
<211> LENGTH: 21
<212> TYPE: DNA
<213> ORGANISM: Human

<400> SEQUENCE: 111
taagaaagtt tctcagaagt a                                        21
```

-continued

```
<210> SEQ ID NO 112
<211> LENGTH: 25
<212> TYPE: DNA
<213> ORGANISM: Human

<400> SEQUENCE: 112
agaaagtttc tcagaagtaa aatgg                                              25

<210> SEQ ID NO 113
<211> LENGTH: 21
<212> TYPE: DNA
<213> ORGANISM: Human

<400> SEQUENCE: 113
aaaatggaca tacctaatac t                                                  21

<210> SEQ ID NO 114
<211> LENGTH: 25
<212> TYPE: DNA
<213> ORGANISM: Human

<400> SEQUENCE: 114
aatggacata cctaatactt tccag                                              25

<210> SEQ ID NO 115
<211> LENGTH: 21
<212> TYPE: DNA
<213> ORGANISM: Human

<400> SEQUENCE: 115
aaatggacat acctaatact t                                                  21

<210> SEQ ID NO 116
<211> LENGTH: 25
<212> TYPE: DNA
<213> ORGANISM: Human

<400> SEQUENCE: 116
atggacatac ctaatacttt ccaga                                              25

<210> SEQ ID NO 117
<211> LENGTH: 21
<212> TYPE: DNA
<213> ORGANISM: Human

<400> SEQUENCE: 117
aatggacata cctaatactt t                                                  21

<210> SEQ ID NO 118
<211> LENGTH: 25
<212> TYPE: DNA
<213> ORGANISM: Human

<400> SEQUENCE: 118
tggacatacc taatactttc cagat                                              25

<210> SEQ ID NO 119
<211> LENGTH: 21
<212> TYPE: DNA
<213> ORGANISM: Human

<400> SEQUENCE: 119
atggacatac ctaatacttt c                                                  21
```

-continued

```
<210> SEQ ID NO 120
<211> LENGTH: 25
<212> TYPE: DNA
<213> ORGANISM: Human

<400> SEQUENCE: 120
ggacatacct aatactttcc agatt                                          25

<210> SEQ ID NO 121
<211> LENGTH: 21
<212> TYPE: DNA
<213> ORGANISM: Human

<400> SEQUENCE: 121
tggacatacc taatactttc c                                              21

<210> SEQ ID NO 122
<211> LENGTH: 25
<212> TYPE: DNA
<213> ORGANISM: Human

<400> SEQUENCE: 122
gacataccta atactttcca gattg                                          25

<210> SEQ ID NO 123
<211> LENGTH: 21
<212> TYPE: DNA
<213> ORGANISM: Human

<400> SEQUENCE: 123
ggacatacct aatactttcc a                                              21

<210> SEQ ID NO 124
<211> LENGTH: 25
<212> TYPE: DNA
<213> ORGANISM: Human

<400> SEQUENCE: 124
acatacctaa tactttccag attga                                          25

<210> SEQ ID NO 125
<211> LENGTH: 21
<212> TYPE: DNA
<213> ORGANISM: Human

<400> SEQUENCE: 125
tcatgtatga ggaggaacct t                                              21

<210> SEQ ID NO 126
<211> LENGTH: 25
<212> TYPE: DNA
<213> ORGANISM: Human

<400> SEQUENCE: 126
atgtatgagg aggaaccttt aaagg                                          25

<210> SEQ ID NO 127
<211> LENGTH: 21
<212> TYPE: DNA
<213> ORGANISM: Human

<400> SEQUENCE: 127
tgtatgagga ggaaccttta a                                              21
```

```
<210> SEQ ID NO 128
<211> LENGTH: 25
<212> TYPE: DNA
<213> ORGANISM: Human

<400> SEQUENCE: 128
tatgaggagg aacctttaaa ggatt                                        25

<210> SEQ ID NO 129
<211> LENGTH: 21
<212> TYPE: DNA
<213> ORGANISM: Human

<400> SEQUENCE: 129
ctaatggata ttgcctacat t                                            21

<210> SEQ ID NO 130
<211> LENGTH: 25
<212> TYPE: DNA
<213> ORGANISM: Human

<400> SEQUENCE: 130
aatggatatt gcctacattt atacc                                        25

<210> SEQ ID NO 131
<211> LENGTH: 21
<212> TYPE: DNA
<213> ORGANISM: Human

<400> SEQUENCE: 131
acatttatac ctggagaagg a                                            21

<210> SEQ ID NO 132
<211> LENGTH: 25
<212> TYPE: DNA
<213> ORGANISM: Human

<400> SEQUENCE: 132
atttatacct ggagaaggaa tggtc                                        25

<210> SEQ ID NO 133
<211> LENGTH: 21
<212> TYPE: DNA
<213> ORGANISM: Human

<400> SEQUENCE: 133
catttatacc tggagaagga a                                            21

<210> SEQ ID NO 134
<211> LENGTH: 25
<212> TYPE: DNA
<213> ORGANISM: Human

<400> SEQUENCE: 134
tttatacctg gagaaggaat ggtcc                                        25

<210> SEQ ID NO 135
<211> LENGTH: 21
<212> TYPE: DNA
<213> ORGANISM: Human

<400> SEQUENCE: 135
acctggagaa ggaatggtcc a                                            21
```

```
<210> SEQ ID NO 136
<211> LENGTH: 25
<212> TYPE: DNA
<213> ORGANISM: Human

<400> SEQUENCE: 136
ctggagaagg aatggtccac ttcca                                              25

<210> SEQ ID NO 137
<211> LENGTH: 21
<212> TYPE: DNA
<213> ORGANISM: Human

<400> SEQUENCE: 137
tccattgaaa tacagagttc g                                                  21

<210> SEQ ID NO 138
<211> LENGTH: 25
<212> TYPE: DNA
<213> ORGANISM: Human

<400> SEQUENCE: 138
cattgaaata cagagttcga cctac                                              25

<210> SEQ ID NO 139
<211> LENGTH: 21
<212> TYPE: DNA
<213> ORGANISM: Human

<400> SEQUENCE: 139
ccattgaaat acagagttcg a                                                  21

<210> SEQ ID NO 140
<211> LENGTH: 25
<212> TYPE: DNA
<213> ORGANISM: Human

<400> SEQUENCE: 140
attgaaatac agagttcgac ctact                                              25

<210> SEQ ID NO 141
<211> LENGTH: 21
<212> TYPE: DNA
<213> ORGANISM: Human

<400> SEQUENCE: 141
tacagagttc gacctacttg t                                                  21

<210> SEQ ID NO 142
<211> LENGTH: 25
<212> TYPE: DNA
<213> ORGANISM: Human

<400> SEQUENCE: 142
cagagttcga cctacttgta aaaga                                              25

<210> SEQ ID NO 143
<211> LENGTH: 21
<212> TYPE: DNA
<213> ORGANISM: Human

<400> SEQUENCE: 143
gaagatcagt caccagagag a                                                  21
```

```
<210> SEQ ID NO 144
<211> LENGTH: 25
<212> TYPE: DNA
<213> ORGANISM: Human

<400> SEQUENCE: 144
agatcagtca ccagagagat ggact                                           25

<210> SEQ ID NO 145
<211> LENGTH: 21
<212> TYPE: DNA
<213> ORGANISM: Human

<400> SEQUENCE: 145
aagatcagtc accagagaga t                                               21

<210> SEQ ID NO 146
<211> LENGTH: 25
<212> TYPE: DNA
<213> ORGANISM: Human

<400> SEQUENCE: 146
gatcagtcac cagagagatg gactg                                           25

<210> SEQ ID NO 147
<211> LENGTH: 21
<212> TYPE: DNA
<213> ORGANISM: Human

<400> SEQUENCE: 147
cattgatgcc acaaccataa t                                               21

<210> SEQ ID NO 148
<211> LENGTH: 25
<212> TYPE: DNA
<213> ORGANISM: Human

<400> SEQUENCE: 148
ttgatgccac aaccataata gaatg                                           25

<210> SEQ ID NO 149
<211> LENGTH: 21
<212> TYPE: DNA
<213> ORGANISM: Human

<400> SEQUENCE: 149
attgatgcca caaccataat a                                               21

<210> SEQ ID NO 150
<211> LENGTH: 25
<212> TYPE: DNA
<213> ORGANISM: Human

<400> SEQUENCE: 150
tgatgccaca accataatag aatgt                                           25

<210> SEQ ID NO 151
<211> LENGTH: 21
<212> TYPE: DNA
<213> ORGANISM: Human

<400> SEQUENCE: 151
tgatgccaca accataatag a                                               21
```

```
<210> SEQ ID NO 152
<211> LENGTH: 25
<212> TYPE: DNA
<213> ORGANISM: Human

<400> SEQUENCE: 152
atgccacaac cataatagaa tgtct                                     25

<210> SEQ ID NO 153
<211> LENGTH: 21
<212> TYPE: DNA
<213> ORGANISM: Human

<400> SEQUENCE: 153
tgcagtctcc tcatccacag t                                         21

<210> SEQ ID NO 154
<211> LENGTH: 25
<212> TYPE: DNA
<213> ORGANISM: Human

<400> SEQUENCE: 154
cagtctcctc atccacagtt tcctc                                     25

<210> SEQ ID NO 155
<211> LENGTH: 21
<212> TYPE: DNA
<213> ORGANISM: Human

<400> SEQUENCE: 155
agtctcctca tccacagttt c                                         21

<210> SEQ ID NO 156
<211> LENGTH: 25
<212> TYPE: DNA
<213> ORGANISM: Human

<400> SEQUENCE: 156
tctcctcatc cacagtttcc tcaca                                     25

<210> SEQ ID NO 157
<211> LENGTH: 21
<212> TYPE: DNA
<213> ORGANISM: Human

<400> SEQUENCE: 157
tttccagtac tatgaatgga a                                         21

<210> SEQ ID NO 158
<211> LENGTH: 25
<212> TYPE: DNA
<213> ORGANISM: Human

<400> SEQUENCE: 158
tccagtacta tgaatggaac cagca                                     25

<210> SEQ ID NO 159
<211> LENGTH: 21
<212> TYPE: DNA
<213> ORGANISM: Human

<400> SEQUENCE: 159
ttccagtact atgaatggaa c                                         21
```

```
<210> SEQ ID NO 160
<211> LENGTH: 25
<212> TYPE: DNA
<213> ORGANISM: Human

<400> SEQUENCE: 160
ccagtactat gaatggaacc agcaa                                              25

<210> SEQ ID NO 161
<211> LENGTH: 21
<212> TYPE: DNA
<213> ORGANISM: Human

<400> SEQUENCE: 161
ccagtactat gaatggaacc a                                                  21

<210> SEQ ID NO 162
<211> LENGTH: 25
<212> TYPE: DNA
<213> ORGANISM: Human

<400> SEQUENCE: 162
agtactatga atggaaccag caaca                                              25

<210> SEQ ID NO 163
<211> LENGTH: 21
<212> TYPE: DNA
<213> ORGANISM: Human

<400> SEQUENCE: 163
agtactatga atggaaccag c                                                  21

<210> SEQ ID NO 164
<211> LENGTH: 25
<212> TYPE: DNA
<213> ORGANISM: Human

<400> SEQUENCE: 164
tactatgaat ggaaccagca acagc                                              25

<210> SEQ ID NO 165
<211> LENGTH: 21
<212> TYPE: DNA
<213> ORGANISM: Human

<400> SEQUENCE: 165
ttttgccaat agacctcgaa a                                                  21

<210> SEQ ID NO 166
<211> LENGTH: 25
<212> TYPE: DNA
<213> ORGANISM: Human

<400> SEQUENCE: 166
ttgccaatag acctcgaaaa tcatc                                              25

<210> SEQ ID NO 167
<211> LENGTH: 21
<212> TYPE: DNA
<213> ORGANISM: Human

<400> SEQUENCE: 167
cagtaaatgg gtcatcagca a                                                  21
```

```
<210> SEQ ID NO 168
<211> LENGTH: 25
<212> TYPE: DNA
<213> ORGANISM: Human

<400> SEQUENCE: 168
gtaaatgggt catcagcaac ttctt                                    25

<210> SEQ ID NO 169
<211> LENGTH: 21
<212> TYPE: DNA
<213> ORGANISM: Human

<400> SEQUENCE: 169
agtaaatggg tcatcagcaa c                                        21

<210> SEQ ID NO 170
<211> LENGTH: 25
<212> TYPE: DNA
<213> ORGANISM: Human

<400> SEQUENCE: 170
taaatgggtc atcagcaact tcttc                                    25

<210> SEQ ID NO 171
<211> LENGTH: 21
<212> TYPE: DNA
<213> ORGANISM: Human

<400> SEQUENCE: 171
aaatgggtca tcagcaactt c                                        21

<210> SEQ ID NO 172
<211> LENGTH: 25
<212> TYPE: DNA
<213> ORGANISM: Human

<400> SEQUENCE: 172
atgggtcatc agcaacttct tctgg                                    25

<210> SEQ ID NO 173
<211> LENGTH: 21
<212> TYPE: DNA
<213> ORGANISM: Human

<400> SEQUENCE: 173
tcccctcggt cactgcattc a                                        21

<210> SEQ ID NO 174
<211> LENGTH: 25
<212> TYPE: DNA
<213> ORGANISM: Human

<400> SEQUENCE: 174
ccctcggtca ctgcattcag aactc                                    25

<210> SEQ ID NO 175
<211> LENGTH: 21
<212> TYPE: DNA
<213> ORGANISM: Human

<400> SEQUENCE: 175
cccctcggtc actgcattca g                                        21
```

```
<210> SEQ ID NO 176
<211> LENGTH: 25
<212> TYPE: DNA
<213> ORGANISM: Human

<400> SEQUENCE: 176
cctcggtcac tgcattcaga actca                                    25

<210> SEQ ID NO 177
<211> LENGTH: 21
<212> TYPE: DNA
<213> ORGANISM: Human

<400> SEQUENCE: 177
ccctcggtca ctgcattcag a                                        21

<210> SEQ ID NO 178
<211> LENGTH: 25
<212> TYPE: DNA
<213> ORGANISM: Human

<400> SEQUENCE: 178
ctcggtcact gcattcagaa ctcat                                    25

<210> SEQ ID NO 179
<211> LENGTH: 21
<212> TYPE: DNA
<213> ORGANISM: Human

<400> SEQUENCE: 179
ggtcactgca ttcagaactc a                                        21

<210> SEQ ID NO 180
<211> LENGTH: 25
<212> TYPE: DNA
<213> ORGANISM: Human

<400> SEQUENCE: 180
tcactgcatt cagaactcat gtgcc                                    25

<210> SEQ ID NO 181
<211> LENGTH: 21
<212> TYPE: DNA
<213> ORGANISM: Human

<400> SEQUENCE: 181
gtcactgcat tcagaactca t                                        21

<210> SEQ ID NO 182
<211> LENGTH: 25
<212> TYPE: DNA
<213> ORGANISM: Human

<400> SEQUENCE: 182
cactgcattc agaactcatg tgccc                                    25

<210> SEQ ID NO 183
<211> LENGTH: 21
<212> TYPE: DNA
<213> ORGANISM: Human

<400> SEQUENCE: 183
tcactgcatt cagaactcat g                                        21
```

```
<210> SEQ ID NO 184
<211> LENGTH: 25
<212> TYPE: DNA
<213> ORGANISM: Human

<400> SEQUENCE: 184
actgcattca gaactcatgt gccct                                    25

<210> SEQ ID NO 185
<211> LENGTH: 21
<212> TYPE: DNA
<213> ORGANISM: Human

<400> SEQUENCE: 185
tgcattcaga actcatgtgc c                                        21

<210> SEQ ID NO 186
<211> LENGTH: 25
<212> TYPE: DNA
<213> ORGANISM: Human

<400> SEQUENCE: 186
cattcagaac tcatgtgccc tatct                                    25

<210> SEQ ID NO 187
<211> LENGTH: 21
<212> TYPE: DNA
<213> ORGANISM: Human

<400> SEQUENCE: 187
cattcagaac tcatgtgccc t                                        21

<210> SEQ ID NO 188
<211> LENGTH: 25
<212> TYPE: DNA
<213> ORGANISM: Human

<400> SEQUENCE: 188
ttcagaactc atgtgcccta tctgc                                    25

<210> SEQ ID NO 189
<211> LENGTH: 21
<212> TYPE: DNA
<213> ORGANISM: Human

<400> SEQUENCE: 189
attcagaact catgtgccct a                                        21

<210> SEQ ID NO 190
<211> LENGTH: 25
<212> TYPE: DNA
<213> ORGANISM: Human

<400> SEQUENCE: 190
tcagaactca tgtgccctat ctgcc                                    25

<210> SEQ ID NO 191
<211> LENGTH: 21
<212> TYPE: DNA
<213> ORGANISM: Human

<400> SEQUENCE: 191
ctgaagaata cgatgaccac c                                        21
```

```
<210> SEQ ID NO 192
<211> LENGTH: 25
<212> TYPE: DNA
<213> ORGANISM: Human

<400> SEQUENCE: 192
gaagaatacg atgaccacca aggag                                         25

<210> SEQ ID NO 193
<211> LENGTH: 21
<212> TYPE: DNA
<213> ORGANISM: Human

<400> SEQUENCE: 193
tgaagaatac gatgaccacc a                                             21

<210> SEQ ID NO 194
<211> LENGTH: 25
<212> TYPE: DNA
<213> ORGANISM: Human

<400> SEQUENCE: 194
aagaatacga tgaccaccaa ggagt                                         25

<210> SEQ ID NO 195
<211> LENGTH: 21
<212> TYPE: DNA
<213> ORGANISM: Human

<400> SEQUENCE: 195
gaagaatacg atgaccacca a                                             21

<210> SEQ ID NO 196
<211> LENGTH: 25
<212> TYPE: DNA
<213> ORGANISM: Human

<400> SEQUENCE: 196
agaatacgat gaccaccaag gagtg                                         25

<210> SEQ ID NO 197
<211> LENGTH: 21
<212> TYPE: DNA
<213> ORGANISM: Human

<400> SEQUENCE: 197
gaatacgatg accaccaagg a                                             21

<210> SEQ ID NO 198
<211> LENGTH: 25
<212> TYPE: DNA
<213> ORGANISM: Human

<400> SEQUENCE: 198
atacgatgac caccaaggag tgcct                                         25

<210> SEQ ID NO 199
<211> LENGTH: 21
<212> TYPE: DNA
<213> ORGANISM: Human

<400> SEQUENCE: 199
gaccaccaag gagtgcctcc a                                             21
```

```
<210> SEQ ID NO 200
<211> LENGTH: 25
<212> TYPE: DNA
<213> ORGANISM: Human

<400> SEQUENCE: 200
ccaccaagga gtgcctccac agatt                                          25

<210> SEQ ID NO 201
<211> LENGTH: 21
<212> TYPE: DNA
<213> ORGANISM: Human

<400> SEQUENCE: 201
accaccaagg agtgcctcca c                                              21

<210> SEQ ID NO 202
<211> LENGTH: 25
<212> TYPE: DNA
<213> ORGANISM: Human

<400> SEQUENCE: 202
caccaaggag tgcctccaca gattc                                          25

<210> SEQ ID NO 203
<211> LENGTH: 21
<212> TYPE: DNA
<213> ORGANISM: Human

<400> SEQUENCE: 203
ccaccaagga gtgcctccac a                                              21

<210> SEQ ID NO 204
<211> LENGTH: 25
<212> TYPE: DNA
<213> ORGANISM: Human

<400> SEQUENCE: 204
accaaggagt gcctccacag attct                                          25

<210> SEQ ID NO 205
<211> LENGTH: 21
<212> TYPE: DNA
<213> ORGANISM: Human

<400> SEQUENCE: 205
aggagtgcct ccacagattc t                                              21

<210> SEQ ID NO 206
<211> LENGTH: 25
<212> TYPE: DNA
<213> ORGANISM: Human

<400> SEQUENCE: 206
gagtgcctcc acagattctg ctctg                                          25

<210> SEQ ID NO 207
<211> LENGTH: 21
<212> TYPE: DNA
<213> ORGANISM: Human

<400> SEQUENCE: 207
cacagattct gctctgactg c                                              21
```

```
<210> SEQ ID NO 208
<211> LENGTH: 25
<212> TYPE: DNA
<213> ORGANISM: Human

<400> SEQUENCE: 208
cagattctgc tctgactgca ttgtc                                              25

<210> SEQ ID NO 209
<211> LENGTH: 21
<212> TYPE: DNA
<213> ORGANISM: Human

<400> SEQUENCE: 209
tgctctgact gcattgtcac a                                                  21

<210> SEQ ID NO 210
<211> LENGTH: 25
<212> TYPE: DNA
<213> ORGANISM: Human

<400> SEQUENCE: 210
ctctgactgc attgtcacag cccta                                              25

<210> SEQ ID NO 211
<211> LENGTH: 21
<212> TYPE: DNA
<213> ORGANISM: Human

<400> SEQUENCE: 211
ctctgactgc attgtcacag c                                                  21

<210> SEQ ID NO 212
<211> LENGTH: 25
<212> TYPE: DNA
<213> ORGANISM: Human

<400> SEQUENCE: 212
ctgactgcat tgtcacagcc ctacg                                              25

<210> SEQ ID NO 213
<211> LENGTH: 21
<212> TYPE: DNA
<213> ORGANISM: Human

<400> SEQUENCE: 213
tgactgcatt gtcacagccc t                                                  21

<210> SEQ ID NO 214
<211> LENGTH: 25
<212> TYPE: DNA
<213> ORGANISM: Human

<400> SEQUENCE: 214
actgcattgt cacagcccta cggag                                              25

<210> SEQ ID NO 215
<211> LENGTH: 21
<212> TYPE: DNA
<213> ORGANISM: Human

<400> SEQUENCE: 215
gactgcattg tcacagccct a                                                  21
```

-continued

```
<210> SEQ ID NO 216
<211> LENGTH: 25
<212> TYPE: DNA
<213> ORGANISM: Human

<400> SEQUENCE: 216
ctgcattgtc acagccctac ggagc                                         25

<210> SEQ ID NO 217
<211> LENGTH: 21
<212> TYPE: DNA
<213> ORGANISM: Human

<400> SEQUENCE: 217
actgcattgt cacagcccta c                                             21

<210> SEQ ID NO 218
<211> LENGTH: 25
<212> TYPE: DNA
<213> ORGANISM: Human

<400> SEQUENCE: 218
tgcattgtca cagccctacg gagcg                                         25

<210> SEQ ID NO 219
<211> LENGTH: 21
<212> TYPE: DNA
<213> ORGANISM: Human

<400> SEQUENCE: 219
ctgcattgtc acagccctac g                                             21

<210> SEQ ID NO 220
<211> LENGTH: 25
<212> TYPE: DNA
<213> ORGANISM: Human

<400> SEQUENCE: 220
gcattgtcac agccctacgg agcgg                                         25

<210> SEQ ID NO 221
<211> LENGTH: 21
<212> TYPE: DNA
<213> ORGANISM: Human

<400> SEQUENCE: 221
gcattgtcac agccctacgg a                                             21

<210> SEQ ID NO 222
<211> LENGTH: 25
<212> TYPE: DNA
<213> ORGANISM: Human

<400> SEQUENCE: 222
attgtcacag ccctacggag cggga                                         25

<210> SEQ ID NO 223
<211> LENGTH: 21
<212> TYPE: DNA
<213> ORGANISM: Human

<400> SEQUENCE: 223
attgtcacag ccctacggag c                                             21
```

```
<210> SEQ ID NO 224
<211> LENGTH: 25
<212> TYPE: DNA
<213> ORGANISM: Human

<400> SEQUENCE: 224
tgtcacagcc ctacggagcg ggaac                                         25

<210> SEQ ID NO 225
<211> LENGTH: 21
<212> TYPE: DNA
<213> ORGANISM: Human

<400> SEQUENCE: 225
agccctacgg agcgggaaca a                                             21

<210> SEQ ID NO 226
<211> LENGTH: 25
<212> TYPE: DNA
<213> ORGANISM: Human

<400> SEQUENCE: 226
ccctacggag cgggaacaag gagtg                                         25

<210> SEQ ID NO 227
<211> LENGTH: 21
<212> TYPE: DNA
<213> ORGANISM: Human

<400> SEQUENCE: 227
gccctacgga gcgggaacaa g                                             21

<210> SEQ ID NO 228
<211> LENGTH: 25
<212> TYPE: DNA
<213> ORGANISM: Human

<400> SEQUENCE: 228
cctacggagc gggaacaagg agtgt                                         25

<210> SEQ ID NO 229
<211> LENGTH: 21
<212> TYPE: DNA
<213> ORGANISM: Human

<400> SEQUENCE: 229
cctacggagc gggaacaagg a                                             21

<210> SEQ ID NO 230
<211> LENGTH: 25
<212> TYPE: DNA
<213> ORGANISM: Human

<400> SEQUENCE: 230
tacggagcgg gaacaaggag tgtcc                                         25

<210> SEQ ID NO 231
<211> LENGTH: 21
<212> TYPE: DNA
<213> ORGANISM: Human

<400> SEQUENCE: 231
agcgggaaca aggagtgtcc t                                             21
```

```
<210> SEQ ID NO 232
<211> LENGTH: 25
<212> TYPE: DNA
<213> ORGANISM: Human

<400> SEQUENCE: 232
cgggaacaag gagtgtccta cctgc                                          25

<210> SEQ ID NO 233
<211> LENGTH: 21
<212> TYPE: DNA
<213> ORGANISM: Human

<400> SEQUENCE: 233
gcgggaacaa ggagtgtcct a                                              21

<210> SEQ ID NO 234
<211> LENGTH: 25
<212> TYPE: DNA
<213> ORGANISM: Human

<400> SEQUENCE: 234
gggaacaagg agtgtcctac ctgcc                                          25

<210> SEQ ID NO 235
<211> LENGTH: 21
<212> TYPE: DNA
<213> ORGANISM: Human

<400> SEQUENCE: 235
cgggaacaag gagtgtccta c                                              21

<210> SEQ ID NO 236
<211> LENGTH: 25
<212> TYPE: DNA
<213> ORGANISM: Human

<400> SEQUENCE: 236
ggaacaagga gtgtcctacc tgccg                                          25

<210> SEQ ID NO 237
<211> LENGTH: 21
<212> TYPE: DNA
<213> ORGANISM: Human

<400> SEQUENCE: 237
gggaacaagg agtgtcctac c                                              21

<210> SEQ ID NO 238
<211> LENGTH: 25
<212> TYPE: DNA
<213> ORGANISM: Human

<400> SEQUENCE: 238
gaacaaggag tgtcctacct gccga                                          25

<210> SEQ ID NO 239
<211> LENGTH: 21
<212> TYPE: DNA
<213> ORGANISM: Human

<400> SEQUENCE: 239
acaaggagtg tcctacctgc c                                              21
```

```
<210> SEQ ID NO 240
<211> LENGTH: 25
<212> TYPE: DNA
<213> ORGANISM: Human

<400> SEQUENCE: 240
aaggagtgtc ctacctgccg aaaga                                    25

<210> SEQ ID NO 241
<211> LENGTH: 21
<212> TYPE: DNA
<213> ORGANISM: Human

<400> SEQUENCE: 241
agtgtcctac ctgccgaaag a                                        21

<210> SEQ ID NO 242
<211> LENGTH: 25
<212> TYPE: DNA
<213> ORGANISM: Human

<400> SEQUENCE: 242
tgtcctacct gccgaaagaa gctgg                                    25

<210> SEQ ID NO 243
<211> LENGTH: 21
<212> TYPE: DNA
<213> ORGANISM: Human

<400> SEQUENCE: 243
gtgtcctacc tgccgaaaga a                                        21

<210> SEQ ID NO 244
<211> LENGTH: 25
<212> TYPE: DNA
<213> ORGANISM: Human

<400> SEQUENCE: 244
gtcctacctg ccgaaagaag ctggt                                    25

<210> SEQ ID NO 245
<211> LENGTH: 21
<212> TYPE: DNA
<213> ORGANISM: Human

<400> SEQUENCE: 245
tgtcctacct gccgaaagaa g                                        21

<210> SEQ ID NO 246
<211> LENGTH: 25
<212> TYPE: DNA
<213> ORGANISM: Human

<400> SEQUENCE: 246
tcctacctgc cgaaagaagc tggtg                                    25

<210> SEQ ID NO 247
<211> LENGTH: 21
<212> TYPE: DNA
<213> ORGANISM: Human

<400> SEQUENCE: 247
gtcctacctg ccgaaagaag c                                        21
```

```
<210> SEQ ID NO 248
<211> LENGTH: 25
<212> TYPE: DNA
<213> ORGANISM: Human

<400> SEQUENCE: 248
cctacctgcc gaaagaagct ggtgt                                    25

<210> SEQ ID NO 249
<211> LENGTH: 21
<212> TYPE: DNA
<213> ORGANISM: Human

<400> SEQUENCE: 249
gaagctggtg tccaagcgat c                                        21

<210> SEQ ID NO 250
<211> LENGTH: 25
<212> TYPE: DNA
<213> ORGANISM: Human

<400> SEQUENCE: 250
agctggtgtc caagcgatcc ctacg                                    25

<210> SEQ ID NO 251
<211> LENGTH: 21
<212> TYPE: DNA
<213> ORGANISM: Human

<400> SEQUENCE: 251
gctggtgtcc aagcgatccc t                                        21

<210> SEQ ID NO 252
<211> LENGTH: 25
<212> TYPE: DNA
<213> ORGANISM: Human

<400> SEQUENCE: 252
tggtgtccaa gcgatcccta cggcc                                    25

<210> SEQ ID NO 253
<211> LENGTH: 21
<212> TYPE: DNA
<213> ORGANISM: Human

<400> SEQUENCE: 253
ctggtgtcca agcgatccct a                                        21

<210> SEQ ID NO 254
<211> LENGTH: 25
<212> TYPE: DNA
<213> ORGANISM: Human

<400> SEQUENCE: 254
ggtgtccaag cgatccctac ggcca                                    25

<210> SEQ ID NO 255
<211> LENGTH: 21
<212> TYPE: DNA
<213> ORGANISM: Human

<400> SEQUENCE: 255
tggtgtccaa gcgatcccta c                                        21
```

```
<210> SEQ ID NO 256
<211> LENGTH: 25
<212> TYPE: DNA
<213> ORGANISM: Human

<400> SEQUENCE: 256
gtgtccaagc gatccctacg gccag                                            25

<210> SEQ ID NO 257
<211> LENGTH: 21
<212> TYPE: DNA
<213> ORGANISM: Human

<400> SEQUENCE: 257
ggtgtccaag cgatccctac g                                                21

<210> SEQ ID NO 258
<211> LENGTH: 25
<212> TYPE: DNA
<213> ORGANISM: Human

<400> SEQUENCE: 258
tgtccaagcg atccctacgg ccaga                                            25

<210> SEQ ID NO 259
<211> LENGTH: 21
<212> TYPE: DNA
<213> ORGANISM: Human

<400> SEQUENCE: 259
tccaagcgat ccctacggcc a                                                21

<210> SEQ ID NO 260
<211> LENGTH: 25
<212> TYPE: DNA
<213> ORGANISM: Human

<400> SEQUENCE: 260
caagcgatcc ctacggccag acccc                                            25

<210> SEQ ID NO 261
<211> LENGTH: 21
<212> TYPE: DNA
<213> ORGANISM: Human

<400> SEQUENCE: 261
ccaagcgatc cctacggcca g                                                21

<210> SEQ ID NO 262
<211> LENGTH: 25
<212> TYPE: DNA
<213> ORGANISM: Human

<400> SEQUENCE: 262
aagcgatccc tacggccaga cccca                                            25

<210> SEQ ID NO 263
<211> LENGTH: 21
<212> TYPE: DNA
<213> ORGANISM: Human

<400> SEQUENCE: 263
caagcgatcc ctacggccag a                                                21
```

```
<210> SEQ ID NO 264
<211> LENGTH: 25
<212> TYPE: DNA
<213> ORGANISM: Human

<400> SEQUENCE: 264
agcgatccct acggccagac cccaa                                       25

<210> SEQ ID NO 265
<211> LENGTH: 21
<212> TYPE: DNA
<213> ORGANISM: Human

<400> SEQUENCE: 265
actttgatgc cctgatctct a                                           21

<210> SEQ ID NO 266
<211> LENGTH: 25
<212> TYPE: DNA
<213> ORGANISM: Human

<400> SEQUENCE: 266
tttgatgccc tgatctctaa gatct                                       25

<210> SEQ ID NO 267
<211> LENGTH: 21
<212> TYPE: DNA
<213> ORGANISM: Human

<400> SEQUENCE: 267
tgatctctaa gatctatcct a                                           21

<210> SEQ ID NO 268
<211> LENGTH: 25
<212> TYPE: DNA
<213> ORGANISM: Human

<400> SEQUENCE: 268
atctctaaga tctatcctag ccggg                                       25

<210> SEQ ID NO 269
<211> LENGTH: 21
<212> TYPE: DNA
<213> ORGANISM: Human

<400> SEQUENCE: 269
gatctctaag atctatccta g                                           21

<210> SEQ ID NO 270
<211> LENGTH: 25
<212> TYPE: DNA
<213> ORGANISM: Human

<400> SEQUENCE: 270
tctctaagat ctatcctagc cggga                                       25

<210> SEQ ID NO 271
<211> LENGTH: 21
<212> TYPE: DNA
<213> ORGANISM: Human

<400> SEQUENCE: 271
atctctaaga tctatcctag c                                           21
```

```
<210> SEQ ID NO 272
<211> LENGTH: 25
<212> TYPE: DNA
<213> ORGANISM: Human

<400> SEQUENCE: 272
ctctaagatc tatcctagcc gggag                                  25

<210> SEQ ID NO 273
<211> LENGTH: 21
<212> TYPE: DNA
<213> ORGANISM: Human

<400> SEQUENCE: 273
tctaagatct atcctagccg g                                      21

<210> SEQ ID NO 274
<211> LENGTH: 25
<212> TYPE: DNA
<213> ORGANISM: Human

<400> SEQUENCE: 274
taagatctat cctagccggg aggaa                                  25

<210> SEQ ID NO 275
<211> LENGTH: 21
<212> TYPE: DNA
<213> ORGANISM: Human

<400> SEQUENCE: 275
ctaagatcta tcctagccgg g                                      21

<210> SEQ ID NO 276
<211> LENGTH: 25
<212> TYPE: DNA
<213> ORGANISM: Human

<400> SEQUENCE: 276
aagatctatc ctagccggga ggaat                                  25

<210> SEQ ID NO 277
<211> LENGTH: 21
<212> TYPE: DNA
<213> ORGANISM: Human

<400> SEQUENCE: 277
taagatctat cctagccggg a                                      21

<210> SEQ ID NO 278
<211> LENGTH: 25
<212> TYPE: DNA
<213> ORGANISM: Human

<400> SEQUENCE: 278
agatctatcc tagccgggag gaata                                  25

<210> SEQ ID NO 279
<211> LENGTH: 21
<212> TYPE: DNA
<213> ORGANISM: Human

<400> SEQUENCE: 279
aagatctatc ctagccggga g                                      21
```

```
<210> SEQ ID NO 280
<211> LENGTH: 25
<212> TYPE: DNA
<213> ORGANISM: Human

<400> SEQUENCE: 280
gatctatcct agccgggagg aatac                                          25

<210> SEQ ID NO 281
<211> LENGTH: 21
<212> TYPE: DNA
<213> ORGANISM: Human

<400> SEQUENCE: 281
gatctatcct agccgggagg a                                              21

<210> SEQ ID NO 282
<211> LENGTH: 25
<212> TYPE: DNA
<213> ORGANISM: Human

<400> SEQUENCE: 282
tctatcctag ccgggaggaa tacga                                          25

<210> SEQ ID NO 283
<211> LENGTH: 21
<212> TYPE: DNA
<213> ORGANISM: Human

<400> SEQUENCE: 283
atctatccta gccgggagga a                                              21

<210> SEQ ID NO 284
<211> LENGTH: 25
<212> TYPE: DNA
<213> ORGANISM: Human

<400> SEQUENCE: 284
ctatcctagc cgggaggaat acgag                                          25

<210> SEQ ID NO 285
<211> LENGTH: 21
<212> TYPE: DNA
<213> ORGANISM: Human

<400> SEQUENCE: 285
ctatcctagc cgggaggaat a                                              21

<210> SEQ ID NO 286
<211> LENGTH: 25
<212> TYPE: DNA
<213> ORGANISM: Human

<400> SEQUENCE: 286
atcctagccg ggaggaatac gaggc                                          25

<210> SEQ ID NO 287
<211> LENGTH: 21
<212> TYPE: DNA
<213> ORGANISM: Human

<400> SEQUENCE: 287
aatacgaggc ccatcaagac c                                              21
```

```
<210> SEQ ID NO 288
<211> LENGTH: 25
<212> TYPE: DNA
<213> ORGANISM: Human

<400> SEQUENCE: 288
tacgaggccc atcaagaccg agtgc                                          25

<210> SEQ ID NO 289
<211> LENGTH: 21
<212> TYPE: DNA
<213> ORGANISM: Human

<400> SEQUENCE: 289
tacgaggccc atcaagaccg a                                              21

<210> SEQ ID NO 290
<211> LENGTH: 25
<212> TYPE: DNA
<213> ORGANISM: Human

<400> SEQUENCE: 290
cgaggcccat caagaccgag tgctt                                          25

<210> SEQ ID NO 291
<211> LENGTH: 21
<212> TYPE: DNA
<213> ORGANISM: Human

<400> SEQUENCE: 291
catcaagacc gagtgcttat c                                              21

<210> SEQ ID NO 292
<211> LENGTH: 25
<212> TYPE: DNA
<213> ORGANISM: Human

<400> SEQUENCE: 292
tcaagaccga gtgcttatcc gcctg                                          25

<210> SEQ ID NO 293
<211> LENGTH: 21
<212> TYPE: DNA
<213> ORGANISM: Human

<400> SEQUENCE: 293
aagaccgagt gcttatccgc c                                              21

<210> SEQ ID NO 294
<211> LENGTH: 25
<212> TYPE: DNA
<213> ORGANISM: Human

<400> SEQUENCE: 294
gaccgagtgc ttatccgcct gagcc                                          25

<210> SEQ ID NO 295
<211> LENGTH: 21
<212> TYPE: DNA
<213> ORGANISM: Human

<400> SEQUENCE: 295
gaccgagtgc ttatccgcct g                                              21
```

```
<210> SEQ ID NO 296
<211> LENGTH: 25
<212> TYPE: DNA
<213> ORGANISM: Human

<400> SEQUENCE: 296
ccgagtgctt atccgcctga gccgc                                           25

<210> SEQ ID NO 297
<211> LENGTH: 21
<212> TYPE: DNA
<213> ORGANISM: Human

<400> SEQUENCE: 297
accgagtgct tatccgcctg a                                               21

<210> SEQ ID NO 298
<211> LENGTH: 25
<212> TYPE: DNA
<213> ORGANISM: Human

<400> SEQUENCE: 298
cgagtgctta tccgcctgag ccgcc                                           25

<210> SEQ ID NO 299
<211> LENGTH: 21
<212> TYPE: DNA
<213> ORGANISM: Human

<400> SEQUENCE: 299
gcctgcacaa ccagcaggca t                                               21

<210> SEQ ID NO 300
<211> LENGTH: 25
<212> TYPE: DNA
<213> ORGANISM: Human

<400> SEQUENCE: 300
ctgcacaacc agcaggcatt gagct                                           25

<210> SEQ ID NO 301
<211> LENGTH: 21
<212> TYPE: DNA
<213> ORGANISM: Human

<400> SEQUENCE: 301
aggaggtgac ggtcctgagg a                                               21

<210> SEQ ID NO 302
<211> LENGTH: 25
<212> TYPE: DNA
<213> ORGANISM: Human

<400> SEQUENCE: 302
gaggtgacgg tcctgaggag cctgc                                           25

<210> SEQ ID NO 303
<211> LENGTH: 21
<212> TYPE: DNA
<213> ORGANISM: Human

<400> SEQUENCE: 303
gcctgctttg cccagcctgg a                                               21
```

```
<210> SEQ ID NO 304
<211> LENGTH: 25
<212> TYPE: DNA
<213> ORGANISM: Human

<400> SEQUENCE: 304
ctgctttgcc cagcctggag ggcgt                                25

<210> SEQ ID NO 305
<211> LENGTH: 21
<212> TYPE: DNA
<213> ORGANISM: Human

<400> SEQUENCE: 305
agcctggagg gcgtcagtga a                                    21

<210> SEQ ID NO 306
<211> LENGTH: 25
<212> TYPE: DNA
<213> ORGANISM: Human

<400> SEQUENCE: 306 cctgagggc gtcagtgaaa agcag                                 25

<210> SEQ ID NO 307
<211> LENGTH: 21
<212> TYPE: DNA
<213> ORGANISM: Human

<400> SEQUENCE: 307
gcctggaggg cgtcagtgaa a                                    21

<210> SEQ ID NO 308
<211> LENGTH: 25
<212> TYPE: DNA
<213> ORGANISM: Human

<400> SEQUENCE: 308
ctggagggcg tcagtgaaaa gcagt                                25

<210> SEQ ID NO 309
<211> LENGTH: 21
<212> TYPE: DNA
<213> ORGANISM: Human

<400> SEQUENCE: 309
aaaagcagta caccatctac a                                    21

<210> SEQ ID NO 310
<211> LENGTH: 25
<212> TYPE: DNA
<213> ORGANISM: Human

<400> SEQUENCE: 310
aagcagtaca ccatctacat cgcac                                25

<210> SEQ ID NO 311
<211> LENGTH: 21
<212> TYPE: DNA
<213> ORGANISM: Human

<400> SEQUENCE: 311
gcagtacacc atctacatcg c                                    21
```

```
<210> SEQ ID NO 312
<211> LENGTH: 25
<212> TYPE: DNA
<213> ORGANISM: Human

<400> SEQUENCE: 312
agtacaccat ctacatcgca cctgg                                         25

<210> SEQ ID NO 313
<211> LENGTH: 21
<212> TYPE: DNA
<213> ORGANISM: Human

<400> SEQUENCE: 313
cagtacacca tctacatcgc a                                             21

<210> SEQ ID NO 314
<211> LENGTH: 25
<212> TYPE: DNA
<213> ORGANISM: Human

<400> SEQUENCE: 314
gtacaccatc tacatcgcac ctgga                                         25

<210> SEQ ID NO 315
<211> LENGTH: 21
<212> TYPE: DNA
<213> ORGANISM: Human

<400> SEQUENCE: 315
gtacaccatc tacatcgcac c                                             21

<210> SEQ ID NO 316
<211> LENGTH: 25
<212> TYPE: DNA
<213> ORGANISM: Human

<400> SEQUENCE: 316
acaccatcta catcgcacct ggagg                                         25

<210> SEQ ID NO 317
<211> LENGTH: 21
<212> TYPE: DNA
<213> ORGANISM: Human

<400> SEQUENCE: 317
caccatctac atcgcacctg g                                             21

<210> SEQ ID NO 318
<211> LENGTH: 25
<212> TYPE: DNA
<213> ORGANISM: Human

<400> SEQUENCE: 318
ccatctacat cgcacctgga ggcgg                                         25

<210> SEQ ID NO 319
<211> LENGTH: 21
<212> TYPE: DNA
<213> ORGANISM: Human

<400> SEQUENCE: 319
accatctaca tcgcacctgg a                                             21
```

```
<210> SEQ ID NO 320
<211> LENGTH: 25
<212> TYPE: DNA
<213> ORGANISM: Human

<400> SEQUENCE: 320
catctacatc gcacctggag gcggg                                              25

<210> SEQ ID NO 321
<211> LENGTH: 21
<212> TYPE: DNA
<213> ORGANISM: Human

<400> SEQUENCE: 321
cggggcgttc acgacgttga a                                                  21

<210> SEQ ID NO 322
<211> LENGTH: 25
<212> TYPE: DNA
<213> ORGANISM: Human

<400> SEQUENCE: 322
gggcgttcac gacgttgaat ggctc                                              25

<210> SEQ ID NO 323
<211> LENGTH: 21
<212> TYPE: DNA
<213> ORGANISM: Human

<400> SEQUENCE: 323
gttcacgacg ttgaatggct c                                                  21

<210> SEQ ID NO 324
<211> LENGTH: 25
<212> TYPE: DNA
<213> ORGANISM: Human

<400> SEQUENCE: 324
tcacgacgtt gaatggctcg ctgac                                              25

<210> SEQ ID NO 325
<211> LENGTH: 21
<212> TYPE: DNA
<213> ORGANISM: Human

<400> SEQUENCE: 325
cacgacgttg aatggctcgc t                                                  21

<210> SEQ ID NO 326
<211> LENGTH: 25
<212> TYPE: DNA
<213> ORGANISM: Human

<400> SEQUENCE: 326
cgacgttgaa tggctcgctg accct                                              25

<210> SEQ ID NO 327
<211> LENGTH: 21
<212> TYPE: DNA
<213> ORGANISM: Human

<400> SEQUENCE: 327
acgacgttga atggctcgct g                                                  21
```

```
<210> SEQ ID NO 328
<211> LENGTH: 25
<212> TYPE: DNA
<213> ORGANISM: Human

<400> SEQUENCE: 328
gacgttgaat ggctcgctga ccctg                                              25

<210> SEQ ID NO 329
<211> LENGTH: 21
<212> TYPE: DNA
<213> ORGANISM: Human

<400> SEQUENCE: 329
cgacgttgaa tggctcgctg a                                                  21

<210> SEQ ID NO 330
<211> LENGTH: 25
<212> TYPE: DNA
<213> ORGANISM: Human

<400> SEQUENCE: 330
acgttgaatg gctcgctgac cctgg                                              25

<210> SEQ ID NO 331
<211> LENGTH: 21
<212> TYPE: DNA
<213> ORGANISM: Human

<400> SEQUENCE: 331
cgctgaccct ggagctggtg a                                                  21

<210> SEQ ID NO 332
<211> LENGTH: 25
<212> TYPE: DNA
<213> ORGANISM: Human

<400> SEQUENCE: 332
ctgaccctgg agctggtgaa tgaga                                              25

<210> SEQ ID NO 333
<211> LENGTH: 21
<212> TYPE: DNA
<213> ORGANISM: Human

<400> SEQUENCE: 333
gctgaccctg gagctggtga a                                                  21

<210> SEQ ID NO 334
<211> LENGTH: 25
<212> TYPE: DNA
<213> ORGANISM: Human

<400> SEQUENCE: 334
tgaccctgga gctggtgaat gagaa                                              25

<210> SEQ ID NO 335
<211> LENGTH: 21
<212> TYPE: DNA
<213> ORGANISM: Human

<400> SEQUENCE: 335
cctggagctg gtgaatgaga a                                                  21
```

```
<210> SEQ ID NO 336
<211> LENGTH: 25
<212> TYPE: DNA
<213> ORGANISM: Human

<400> SEQUENCE: 336
tggagctggt gaatgagaaa ttctg                                              25

<210> SEQ ID NO 337
<211> LENGTH: 21
<212> TYPE: DNA
<213> ORGANISM: Human

<400> SEQUENCE: 337
gagctggtga atgagaaatt c                                                  21

<210> SEQ ID NO 338
<211> LENGTH: 25
<212> TYPE: DNA
<213> ORGANISM: Human

<400> SEQUENCE: 338
gctggtgaat gagaaattct ggaag                                              25

<210> SEQ ID NO 339
<211> LENGTH: 21
<212> TYPE: DNA
<213> ORGANISM: Human

<400> SEQUENCE: 339
gctggtgaat gagaaattct g                                                  21

<210> SEQ ID NO 340
<211> LENGTH: 25
<212> TYPE: DNA
<213> ORGANISM: Human

<400> SEQUENCE: 340
tggtgaatga gaaattctgg aaggt                                              25

<210> SEQ ID NO 341
<211> LENGTH: 21
<212> TYPE: DNA
<213> ORGANISM: Human

<400> SEQUENCE: 341
ctggtgaatg agaaattctg g                                                  21

<210> SEQ ID NO 342
<211> LENGTH: 25
<212> TYPE: DNA
<213> ORGANISM: Human

<400> SEQUENCE: 342
ggtgaatgag aaattctgga aggtg                                              25

<210> SEQ ID NO 343
<211> LENGTH: 21
<212> TYPE: DNA
<213> ORGANISM: Human

<400> SEQUENCE: 343
tgagaaattc tggaaggtgt c                                                  21
```

```
<210> SEQ ID NO 344
<211> LENGTH: 25
<212> TYPE: DNA
<213> ORGANISM: Human

<400> SEQUENCE: 344
agaaattctg gaaggtgtcc cggcc                                          25

<210> SEQ ID NO 345
<211> LENGTH: 21
<212> TYPE: DNA
<213> ORGANISM: Human

<400> SEQUENCE: 345
gaaattctgg aaggtgtccc g                                              21

<210> SEQ ID NO 346
<211> LENGTH: 25
<212> TYPE: DNA
<213> ORGANISM: Human

<400> SEQUENCE: 346
aattctggaa ggtgtcccgg ccact                                          25

<210> SEQ ID NO 347
<211> LENGTH: 21
<212> TYPE: DNA
<213> ORGANISM: Human

<400> SEQUENCE: 347
ctgtgctatg ctcccaccaa g                                              21

<210> SEQ ID NO 348
<211> LENGTH: 25
<212> TYPE: DNA
<213> ORGANISM: Human

<400> SEQUENCE: 348
gtgctatgct cccaccaagg atcca                                          25
```

METHODS FOR ENHANCING THE THERAPEUTIC EFFICACY OF TOPOISOMERASE INHIBITORS

This application claims the benefits of U.S. Provisional Patent Application Ser. Nos. 61/005,636, filed Dec. 5, 2007 and 60/880,775, filed Jan. 16, 2007. The contents of which are hereby incorporated by reference in its entirety.

Throughout this application various publications are referenced in parenthesis. The disclosures of these publications in their entireties are hereby incorporated by reference into this application in order to more fully describe the state of the art to which this invention pertains.

BACKGROUND OF THE INVENTION

DNA topoisomerases are nuclear enzymes that regulate the conformational changes in DNA topology by catalyzing the breakage and rejoining of DNA strands during the normal cell cycle. They relieve torsional stress during replication and transcription.

Five human DNA topoisomerases have been identified and characterized: topoisomerase I (TOPI), topoisomerase IIα (TOPIIα), topoisomerase IIβ (TOPIIβ), topoisomerase IIIα (TOP3α), and topoisomerase IIIβ (TOP3β). TOPI reversibly cleaves a single strand in duplex DNA molecule, whereas TOPII breaks and rejoins both DNA strands. These reactions are believed to occur via transient reaction intermediates, known as "cleavable complexes," where the enzymes (or enzyme subunits) form covalent bonds involving a tyrosine and the cleaved phosphodiester bond of the DNA substrate backbone.

To date, TOPI, TOPIIα, and TOPIIβ have been demonstrated to be important molecular targets for antitumor drugs (Gurrieri, C., et al., J Natl Cancer Inst, 2004. 96(4):269-79). During the past few years topoisomerases have become important chemotherapeutic targets for cancer treatment. Camptothecin (CPT) and its derivatives are reported to act specifically at the level of the TOPI-DNA complex and stimulate DNA cleavage. Other agents, such as β-lapachone, act by blocking the formation of the topoisomerase I-DNA complex. Several novel compounds have been developed that can target either TOPI or TOPIIα/IIβ-isoforms, or that can target all three types of topoisomerases.

As described above, TOPI catalyzes changes in DNA topology via the formation of a reversible enzyme-DNA cleavage complex. Anti-tumor drugs targeting TOPI, such as camptothecin (CPT) and its derivatives, lock the TOPI-DNA complex, resulting in cytotoxic DNA lesions that trigger cell cycle arrest and cell death.

CPT-mediated stabilization of TOPI-DNA complexes also induces TOPI proteasome-mediated degradation, which prevents topoisomerase inhibitor mediated cell death (Gambacorta, M., et al., Am J Pathol, 1996. 149(6): p. 2023-35 and Koken, M. H., et al., 10(7): p. 1315-24). In breast and colorectal cancer cell lines, there is a correlation between the extent of CPT-induced TOPI degradation and CPT resistance. For example, the breast cancer cell line ZR-75-1 is extremely sensitive to CPT and is completely defective in CPT-induced TOPI degradation, while the breast cancer cell line BT474 is insensitive to CPT and exhibits effective CPT-induced TOPI degradation (Zhang, P., et al., Int J Cancer, 2000. 85(5): p. 599-605). Supporting an essential role for ubiquitin-mediated degradation in the emergence of drug resistance, inhibiting proteasomes abolishes CPT-induced degradation of TOPI and selectively sensitized BT474 cells to CPT-induced cytotoxicity and apoptosis (Zhang, P., et al., Int J Cancer, 2000. 85(5): p. 599-605). Human TOPII isozymes, TOPIIα and TOPIIβ, are targeted in cancer cells by anthracyclines, such as doxorubicin, Teniposide (VM26, Alexis Corp.) and epipodophylotoxins, such as etoposide (VP-16)(Sigma, Israel).

TOPII inhibitors act in two diverse mechanisms. The first mechanism is similar to the TOPI inhibitors (e.g. VP-16) (Gurrieri, C., et al., J Natl Cancer Inst, 2004. 96(4): p. 269-79), while the second mechanism (e.g. ICRF-193) inhibits the catalytic activity of TOPII without trapping the covalent ternary complex (Yu, J. H., et al., Cancer Res., 2004. 64(3): p. 928-33 and Son, S. H., et al., Cancer Gene Ther, 2004. 5: p. 5). Most inhibitors of topoisomerase II block the ligation step, leading to stabilized cleavable complexes between DNA and the enzyme. Most enzyme inhibitors function by docking into the enzyme active site or nearby allosteric site to block the reaction of the normal substrate. Inhibition of the topoisomerase II involves two parts: the aromatic part of the inhibitor molecule intercalates between DNA base pairs while another more polar portion interacts with topoisomerase.

Because many topoisomerase II inhibitors (e.g., doxorubicin, and etoposide) act as poisons rather than as classical competitive inhibitors, their action is dependent upon the level of the enzyme in cells. Rapidly proliferating cells, which contain relatively higher levels of topoisomerase II, appear to be more sensitive to these agents. On the other hand, differentiated cells have relatively low topoisomerase II levels and are much more resistant to the action of these inhibitors.

Similarly to TOPI, the TOPII-DNA-Drug complex becomes susceptible to proteasome-mediated degradation contributing to the emergence of drug resistance (Le, X. F., et al., Oncogene, 1998. 16(14): p. 1839-49 and He, D., et al., Chin Med J (Engl), 2003. 116(9): p. 1394-8). Proteasome inhibition can circumvent solid tumor resistance to TOPII-directed drugs (He, D., et al., Cancer Res., 1997. 57(10): p. 1868-72). Physiological cell conditions, such as but not limited to glucose deprivation and hypoxia, play a role in solid tumor drug resistance (Melnick, A. and J. D. Licht, Blood, 1999. 93(10): p. 3167-215). These tumor-specific conditions cause decreases in TOPIIα levels, rendering cells resistant to TOPII-targeted drugs such as etoposide and doxorubicin (Piazza, F. C. Gurrieri, & P. P. Pandolfi, Oncogene, 2001. 20(49): p. 7216-22).

There remains a continuing need for developing approaches and compositions that are useful for enhancing the therapeutic effects of topoisomerase inhibitors.

SUMMARY OF THE INVENTION

This invention provides a method for modulating cell growth, comprising contacting a cell with an effective amount of an inhibitor of an E3 ubiquitin ligase, and contacting the cell with an effective amount of a topoisomerase inhibitor such that the E3 ubiquitin ligase inhibitor and topoisomerase inhibitor modulate cell growth to a greater extent in comparison to a corresponding cell treated with the topoisomerase inhibitor alone.

This invention further provides a method for stabilizing a topoisomerase in a cell, comprising contacting the cell with an effective amount of an inhibitor of E3 ubiquitin ligase.

This invention also provides a method for identifying an E3 ubiquitin ligase inhibitor, the method comprising:
  providing a test agent;
  contacting an E3 ubiquitin ligase with a ubiquitin activating enzyme, a substrate of the E3 ubiquitin ligase, and ubiquitin in the presence or absence of the test agent; and
  determining whether ubiquitination of the substrate is decreased in the presence of the test agent, wherein the test agent is identified as an E3 ubiquitin ligase inhibitor where ubiquitination of the substrate is decreased in the presence of the test agent.

This invention additionally provides an inhibitory compound identified by the method described above.

This invention further provides a process for making a compound that inhibits the ubiquitination of a substrate by an E3 ubiquitin ligase, the method comprising:
carrying out the method as described above to identify the test agent that inhibits the ubiquitination of the E3 ubiquitin ligase substrate by the E3 ubiquitin ligase; and
manufacturing the test agent.

This invention further provides a method for identifying a compound which re-sensitizes a cell to a topoisomerase inhibitor, the method comprising:
providing a test agent;
contacting a cell with an effective amount of a test agent, and contacting the cell with an effective amount of the topoisomerase inhibitor; and
determining whether the treatment with the test agent and topoisomerase inhibitor modulates cell growth in comparison to a cell treated with the topoisomerase inhibitor alone, wherein the test agent is identified as a compound which resensitizes a cell to the topoisomerase inhibitor if the cell growth is reduced.

This invention additionally provides an inhibitory compound identified by the method as described above.

This invention also provides a process for making a compound that inhibits the ubiquitination of a substrate by an E3 ubiquitin ligase, the method comprising:
carrying out the method as described above to identify the test agent that inhibits the ubiquitination of the E3 ubiquitin ligase substrate by the E3 ubiquitin ligase; and
manufacturing the test agent.

This invention additionally provides an isolated double-stranded ribonucleic acid (dsRNA) molecule comprising a first strand of nucleotides that is substantially identical to 19 to 25 consecutive nucleotides set forth in NM_005180.5 or NM_002931.3, and a second strand that is substantially complementary to the first.

This invention also provides an isolated dsRNA molecule comprising a first strand of nucleotides comprising a sequence set forth in NM_005180.5 or NM_002931.3, and a second strand of nucleotides comprising a sequence substantially complementary to the first.

This invention further provides an isolated dsRNA molecule that inhibits expression of a protein encoded by a nucleic acid molecule comprising a strand set forth in NM_005180.5 or NM_002931.3, wherein a first strand of the dsRNA is substantially identical to 19 to 25 consecutive nucleotides set forth in NM_005180.5 or NM_002931.3, and a second strand of the dsRNA is substantially complementary to the first.

This invention also provides an isolated nucleic acid molecule comprising a promoter operatively linked to a nucleotide sequence that is a template for one or both strands of the dsRNA described above.

This invention additionally provides an expression vector comprising the isolated nucleic acid molecule described above.

This invention also provides a pharmaceutical composition comprising a dsRNA molecule having a first and a second strand of nucleotides, wherein the dsRNA molecule is selected from the group consisting of:
a dsRNA molecule comprising a first strand of nucleotides that is substantially identical to 19 to 25 consecutive nucleotides set forth in NM_005180.5 or NM_002931.3, and a second strand that is substantially complementary to the first; and
a dsRNA molecule comprising a first strand of nucleotides comprising a sequence set forth in NM_005180.5 or NM_002931.3, and a second strand of nucleotides comprising a sequence substantially complementary to the first,
wherein the dsRNA molecule inhibits expression of a protein encoded by a nucleic acid molecule comprising a strand set forth in NM_005180.5 or NM_002931.3.

This invention additionally provides a method for stabilizing a topoisomerase, comprising contacting a cell with an effective amount of a dsRNA molecule that is substantially identical to a portion of a target gene selected from the group consisting of:
a polynucleotide as defined in NM_005180.5;
a polynucleotide that hybridizes under stringent conditions to a polynucleotide as defined in NM_005180.5;
a polynucleotide as defined in NM_002931.3; and
a polynucleotide that hybridizes under stringent conditions to a polynucleotide as defined in NM_002931.3,
such that the topoisomerase is stabilized.

This invention further provides a method for identifying a target for RNA interference comprising the steps of:
selecting an E3 ubiquitin ligase as a target gene sequence;
contacting a cell with a dsRNA that is substantially identical to a portion of the target gene sequence; and
determining whether the dsRNA stabilizes a topoisomerase.

DETAILED DESCRIPTION OF THE INVENTION

Figure 1:
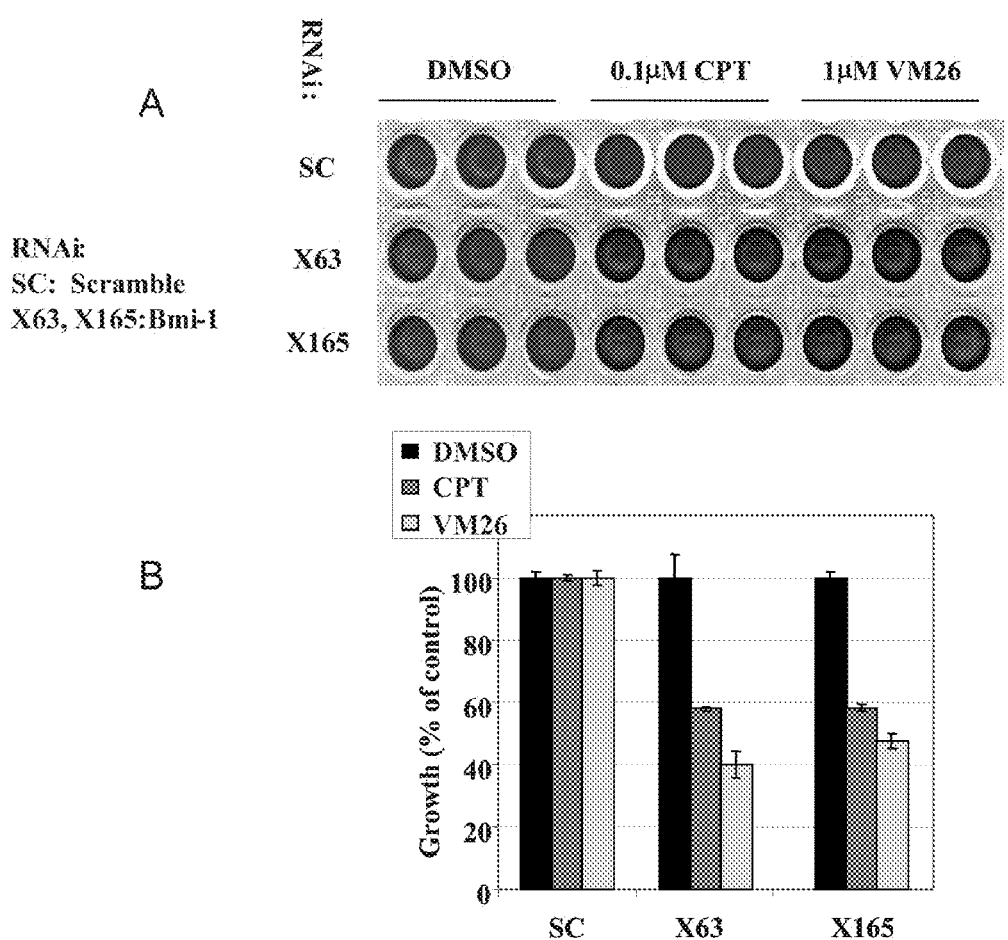
FIGS. 1A and B show HeLa cells transfected with RNAi oligomers targeting Bmi1, X63 or X165, or transfected with a scrambled RNAi, Sc, using SaintRed reagent according to the manufacturer's instructions (Synvolux Therapeutics, B.V., NL). Cells were cultured in the presence of DMSO, 0.1 μM CPT or 1 μM VM26, and stained with AlamarBlue. 1A shows images of the stained cells, while 1B charts and compares cell growth in the different conditions, indicating that inhibition of Bmi1 using RNAi increases VM26 and CPT-induces toxicity in HeLa cells.

This invention provides a method for modulating cell growth, comprising contacting a cell with an effective amount of an inhibitor of an E3 ubiquitin ligase, and contacting the cell with an effective amount of a topoisomerase inhibitor such that the E3 ubiquitin ligase inhibitor and topoisomerase inhibitor modulate cell growth to a greater extent in comparison to a corresponding cell treated with the topoisomerase inhibitor alone.

In one embodiment of the method the cell is a human cell. The cell may be a cancer cell. The cancer cell is a cardiac, lung, gastrointestinal, genitourinary tract, liver, bone, nervous system, gynecological, hematologic, skin, or adrenal gland cancer cell.

In an embodiment of the method cell growth is inhibited. In yet another embodiment of the method the topoisomerase inhibitor is selected from the group consisting of camptothecin, irinotecan, topotecan, doxorubicin, teniposide, etoposide, and analogs, derivatives, and combinations thereof.

In another embodiment of the method the inhibitor of E3 ubiquitin ligase is a compound having the structure

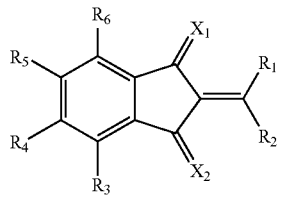

wherein $R_1$ and $R_2$ are independently hydrogen, hydroxyl, alkyl, alkenyl, alkynyl, cycloalkyl, heterocyclic alkyl, aryl, heterocyclic aryl, acyl, alkoxy, amino, carboxyl, nitrile, sulfide, sulfone or sulfonamide, wherein each of the cycloalkyl, heteroclyclic alkyl, aryl, and heterocyclic aryl are optionally substituted with 1 to 3 groups selected from halogen, hydroxyl, amino, nitro, nitrile, sulfide, C1-C6 alkyl, halogenated C1-C6 alkyl, mono- or di-(C1-C6 alkyl) amine, C1-C6 alkoxy, or aryl or heterocyclic aryl;

$X_1$ and $X_2$ are independently oxygen or sulfur; and $R_3$, $R_4$, $R_5$ and $R_6$, are each independently hydrogen, halogen, amine, amide, hydroperoxy, alkyl, alkoxy, alkenyl, acyl, carboxyl, carboxylate, aryl, heterocyclic aryl;

or a salt or an enantiomer of the compound.

In an additional embodiment of the method the inhibitor of E3 ubiquitin ligase is a compound having the structure:

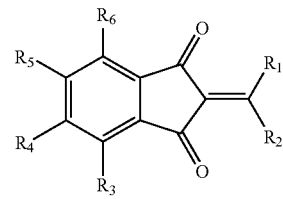

wherein $R_1$ and $R_2$ are independently hydrogen, hydroxyl, alkyl, alkenyl, alkynyl, cycloalkyl, heterocyclic alkyl, aryl, heterocyclic aryl, acyl, alkoxy, amino, carboxyl, nitrile, sulfide, sulfone or sulfonamide, wherein each of the cycloalkyl, heteroclyclic alkyl, aryl, and heterocyclic aryl are optionally substituted with 1 to 3 groups selected from halogen, hydroxyl, amino, nitro, nitrile, sulfide, C1-C6 alkyl, halogenated C1-C6 alkyl, mono- or di-(C1-C6 alkyl) amine, C1-C6 alkoxy, or aryl or heterocyclic aryl; and $R_3$, $R_4$, $R_5$ and $R_6$, are each independently hydrogen, halogen, amine, amide, hydroperoxy, alkyl, alkoxy, alkenyl, acyl, carboxyl, carboxylate, aryl, heterocyclic aryl;

or a salt or an enantiomer of the compound.

In an embodiment of the method $R_3$ is hydrogen, $R_4$ is hydrogen, $R_5$ is hydrogen, $R_6$ is hydrogen, $R_3$ and $R_6$ are hydrogen, or $R_4$ and $R_5$ are hydrogen.

In yet another embodiment of the method the inhibitor of E3 ubiquitin ligase is:

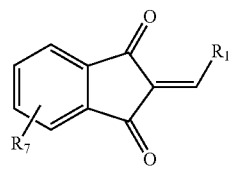

wherein $R_1$ is alkyl, acyl, amine, carboxylic acid, alkoxy, sulfone, sulfonamide aryl, or heterocyclic aryl, and $R_7$ is hydrogen, halogen, alkyl, acyl, carboxylic acid, alkoxy, aryl, or heterocyclic aryl, Or a salt or enantiomer of the compound.

In one embodiment of the method the inhibitor of E3 ubiquitin ligase is compound 1:

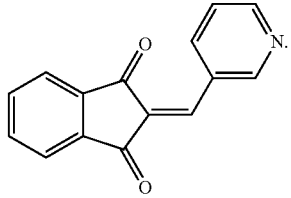

In an additional embodiment of the method the inhibitor of E3 ubiquitin ligase is a compound having the structure:

wherein $R_1$ and $R_2$ are independently hydrogen, hydroxyl, alkyl, alkenyl, alkynyl, cycloalkyl, heterocyclic alkyl, aryl, heterocyclic aryl, acyl, alkoxy, amino, carboxyl, nitrile, sulfide, sulfone or sulfonamide, wherein each of the cycloalkyl, heteroclyclic alkyl, aryl, and heterocyclic aryl are optionally substituted with 1 to 3 groups selected from halogen, hydroxyl, amino, nitro, nitrile, sulfide, C1-C6 alkyl, halogenated C1-C6 alkyl, mono- or di-(C1-C6 alkyl) amine, C1-C6 alkoxy, or aryl or heterocyclic aryl; and $R_3$, $R_4$, $R_5$ and $R_6$, are each independently hydrogen, halogen, amine, amide, hydroperoxy, alkyl, alkoxy, alkenyl, acyl, carboxyl, carboxylate, aryl, heterocyclic aryl;

or a salt or an enantiomer of the compound.

In one embodiment of this method $R_3$ is hydrogen, $R_4$ is hydrogen, $R_5$ is hydrogen, $R_6$ is hydrogen, $R_3$ and $R_6$ are hydrogen, or $R_4$ and $R_5$ are hydrogen.

In an additional embodiment of the method the inhibitor of E3 ubiquitin ligase is a compound having the structure:

wherein $R_1$ is alkyl, acyl, amine, carboxylic acid, alkoxy, sulfone, sulfonamide aryl, or heterocyclic aryl, and $R_7$ is hydrogen, halogen, alkyl, acyl, carboxylic acid, alkoxy, aryl, or heterocyclic aryl, or a salt enantiomer of the compound.

In one embodiment of the inhibitor of E3 ubiquitin ligase is:

This invention further provides a method for stabilizing a topoisomerase in a cell, comprising contacting the cell with an effective amount of an inhibitor of E3 ubiquitin ligase. In this method the E3 ubiquitin ligase is a compound having the structure as described above.

This invention also provides a method for identifying an E3 ubiquitin ligase inhibitor, the method comprising: providing a test agent; contacting an E3 ubiquitin ligase with a ubiquitin activating enzyme, a substrate of the E3 ubiquitin ligase, and ubiquitin in the presence or absence of the test agent; and determining whether ubiquitination of the substrate is decreased in the presence of the test agent, wherein the test agent is identified as an E3 ubiquitin ligase inhibitor where ubiquitination of the substrate is decreased in the presence of the test agent.

In one embodiment of the method the E3 ubiquitin ligase is RING1, Bmi1, and/or a combination thereof.

In an additional embodiment of the method the ubiquitination of the substrate is determined fluorescently.

In a further embodiment of the method the contacting step occurs in a cell.

In yet a further embodiment of the method the substrate is a RING1/Bmi1 complex.

In one embodiment of the method the substrate is a topoisomerase.

This invention additionally provides an inhibitory compound identified by the method described above.

This invention further provides a process for making a compound that inhibits the ubiquitination of a substrate by an E3 ubiquitin ligase, the method comprising carrying out the method as described above to identify the test agent that inhibits the ubiquitination of the E3 ubiquitin ligase substrate by the E3 ubiquitin ligase; and manufacturing the test agent.

This invention further provides a method for identifying a compound which re-sensitizes a cell to a topoisomerase inhibitor, the method comprising:

providing a test agent;

contacting a cell with an effective amount of a test agent, and contacting the cell with an effective amount of the topoisomerase inhibitor; and determining whether the treatment with the test agent and topoisomerase inhibitor modulates cell growth in comparison to a cell treated with the topoisomerase inhibitor alone, wherein the test agent is identified as a compound which resensitizes a cell to the toposiomerase inhibitor if the cell growth is reduced.

In one embodiment of the method the cell is a human cell. The cell may be a cancer cell. The cancer cell may be a cardiac, lung, gastrointestinal, genitourinary tract, liver, bone, nervous system, gynecological, hematologic, skin, or adrenal gland cancer cell.

In another embodiment of the method the cell growth is inhibited.

In one embodiment of the method the test agent stabilizes topoisomerase.

In a further embodiment of the method the topoisomerase inhibitor is selected from the group consisting of camptothecin, irinotecan, topotecan, doxorubicin, teniposide, etoposide, and analogs, derivatives, and combinations thereof.

This invention additionally provides an inhibitory compound identified by the method as described above.

This invention also provides a process for making a compound that inhibits the ubiquitination of a substrate by an E3 ubiquitin ligase, the method comprising carrying out the method as described above to identify the test agent that inhibits the ubiquitination of the E3 ubiquitin ligase substrate by the E3 ubiquitin ligase; and manufacturing the test agent.

This invention additionally provides an isolated double-stranded ribonucleic acid (dsRNA) molecule comprising a first strand of nucleotides that is substantially identical to 19 to 25 consecutive nucleotides set forth in NM_005180.5 or NM_002931.3, and a second strand that is substantially complementary to the first.

This invention also provides an isolated dsRNA molecule comprising a first strand of nucleotides comprising a sequence set forth in NM_005180.5 or NM_002931.3, and a second strand of nucleotides comprising a sequence substantially complementary to the first.

This invention further provides an isolated dsRNA molecule that inhibits expression of a protein encoded by a nucleic acid molecule comprising a strand set forth in NM_005180.5 or NM_0029341.3, wherein a first strand of the dsRNA is substantially identical to 19 to 25 consecutive nucleotides set forth in NM_005180.5 or NM_002931.3, and a second strand of the dsRNA is substantially complementary to the first.

This invention also provides an isolated nucleic acid molecule comprising a promoter operatively linked to a nucleotide sequence that is a template for one or both strands of the dsRNA described above.

This invention additionally provides an expression vector comprising the isolated nucleic acid molecule described above.

In one embodiment of the method a promoter flanks either end of the nucleotide sequence, wherein the promoters drive expression of each individual DNA strand, hereby generating two complementary RNAs that hybridize and form the dsRNA.

In one embodiment of the methods the dsRNA molecule is selected from the group consisting of:
  a dsRNA molecule having a first strand comprising the sequence set forth in SEQ ID NO:3 and the second strand comprising the sequence set forth in SEQ ID NO:4;
  a dsRNA molecule having a first strand comprising the sequence set forth in SEQ ID NO:5 and the second strand comprising the sequence set forth in SEQ ID NO:6;
  a dsRNA molecule having a first strand comprising the sequence set forth in SEQ ID NO:7 and the second strand comprising the sequence set forth in SEQ ID NO:8;
  a dsRNA molecule having a first strand comprising the sequence set forth in SEQ ID NO:9 and the second strand comprises the sequence set forth in SEQ ID NO:10; and
  combinations thereof.

This invention also provides a pharmaceutical composition comprising a dsRNA molecule having a first and a second strand of nucleotides, wherein the dsRNA molecule is selected from the group consisting of:
  a dsRNA molecule comprising a first strand of nucleotides that is substantially identical to 19 to 25 consecutive nucleotides set forth in NM_005180.5 or NM_002931.3, and a second strand that is substantially complementary to the first; and
  a dsRNA molecule comprising a first strand of nucleotides comprising a sequence set forth in NM_005180.5 or NM_002931.3, and a second strand of nucleotides comprising a sequence substantially complementary to the first,
  wherein the dsRNA molecule inhibits expression of a protein encoded by a nucleic acid molecule comprising a strand set forth in NM_005180.5 or NM_002931.3.

In one embodiment of the method the dsRNA molecule is selected from the group as described above.

This invention additionally provides a method for stabilizing a topoisomerase, comprising contacting a cell with an effective amount of a dsRNA molecule that is substantially identical to a portion of a target gene selected from the group consisting of:
  a polynucleotide as defined in NM_005180.5;
  a polynucleotide that hybridizes under stringent conditions to a polynucleotide as defined in NM_005180.5;
  a polynucleotide as defined in NM_002931.3; and
  a polynucleotide that hybridizes under stringent conditions to a polynucleotide as defined in NM_002931.3,
  such that the topoisomerase is stabilized.

In one embodiment of the method the cell is a human cell. The cell may be a cancer cell. The cancer cell is selected from the group consisting of a cardiac, lung, gastrointestinal, genitourinary tract, liver, bone, nervous system, gynecological, hematologic, skin, or adrenal gland cancer cell.

In yet another embodiment of the method the dsRNA molecule is selected from the group as described above.

In another embodiment of the method the E3 ubiquitin ligase inhibitor is selected from the group consisting of DNA and RNA. The RNA may be a dsRNA molecule. The dsRNA molecule may be substantially identical to a portion of a target gene selected from the group consisting of:
  a polynucleotide as defined in NM_005180.5;
  a polynucleotide that hybridizes under stringent conditions to a polynucleotide as defined in NM_005180.5;
  a polynucleotide as defined in NM_002931.3; and
  a polynucleotide that hybridizes under stringent conditions to a polynucleotide as defined in NM_002931.3.

In another embodiment of the method the dsRNA molecule is selected from the group as described above.

This invention further provides a method for identifying a target for RNA interference comprising the steps of:
  selecting an E3 ubiquitin ligase as a target gene sequence;
  contacting a cell with a dsRNA that is substantially identical to a portion of the target gene sequence; and
  determining whether the dsRNA stabilizes a topoisomerase.

In one embodiment of the method the target gene sequence is selected from the group consisting of:
  a polynucleotide as defined in NM_005180.5;
  a polynucleotide that hybridizes under stringent conditions to a polynucleotide as defined in NM_005180.5;
  a polynucleotide as defined in NM_002931.3; and
  a polynucleotide that hybridizes under stringent conditions to a polynucleotide as defined in NM_002931.3.

In another embodiment of the method the topoisomerase is selected from the group consisting of human topoisomerase I, human topoisomerase IIα, human topoisomerase IIβ, and combinations thereof.

In yet another embodiment of the method the cell is contacted with an effective amount of a topoisomerase inhibitor and cell growth is modulated.

In one embodiment of the method the test agent is a dsRNA molecule. The dsRNA molecule may be substantially identical to a portion of a target gene selected from the group consisting of:
  a polynucleotide as defined in NM_005180.5;
  a polynucleotide that hybridizes under stringent conditions to a polynucleotide as defined in NM_005180.5;
  a polynucleotide as defined in NM_002931.3; and
  a polynucleotide that hybridizes under stringent conditions to a polynucleotide as defined in NM_002931.3.

In a further embodiment of the method the dsRNA molecule is selected from the group as described above.

This invention further provides a method of treating a subject with cancer, comprising administering an effective amount of the pharmaceutical composition with an effective amount of a topoisomerase inhibitor to a subject with cancer.

In one embodiment of the method the treatment modulates growth of a cancer cell. The modulation may comprise an increase in cell death. The treatment may increase sensitivity to the topoisomerase inhibitor.

In a further embodiment of the method the topoisomerase inhibitor is selected from the group consisting of Camptothecin, Campto, Camptosar, Hycamtin, Doxorubicin, Teniposide, Adriamycin, VePesid, etoposide, and analogs, derivatives, and combinations thereof.

This invention further provides a method of treating a subject with lung cancer, comprising administering an effective amount of the pharmaceutical composition indicated above to a subject with lung cancer.

In another embodiment of the method the dsRNA molecule of the pharmaceutical composition is selected from the group consisting of:
 a dsRNA molecule comprising a first strand of nucleotides that is substantially identical to 19 to 25 consecutive nucleotides set forth in NM_005180.5, and a second strand that is substantially complementary to the first; and
 a dsRNA molecule comprising a first strand of nucleotides comprising a sequence set forth in NM_005180.5, and a second strand of nucleotides comprising a sequence substantially complementary to the first,
 wherein the dsRNA molecule inhibits expression of a protein encoded by a nucleic acid molecule comprising a strand set forth in NM_005180.5.

The method wherein the dsRNA molecule is selected from the group consisting of:
 a dsRNA molecule having a first strand comprising the sequence set forth in SEQ ID NO:3 and the second strand comprising the sequence set forth in SEQ ID NO:4;
 a dsRNA molecule having a first strand comprising the sequence set forth in SEQ ID NO:5 and the second strand comprising the sequence set forth in SEQ ID NO:6; and
 combinations thereof.

The invention also provides for A kit comprising an effective amount of a dsRNA molecule substantially identical to a portion of a target gene selected from the group consisting of:
 a polynucleotide as defined in NM_005180.5;
 a polynucleotide that hybridizes under stringent conditions to a polynucleotide as defined in NM_005180.5;
 a polynucleotide as defined in NM_002931.3;
 a polynucleotide that hybridizes under stringent conditions to a polynucleotide as defined in NM_002931.3; and
 an instruction means for administering said compound to a mammal having cancer.

In one embodiment of the kit the dsRNA molecule is selected from the group as described above.

In another embodiment of the kit, the kit further comprises an effective amount of a topoisomerase inhibitor.

Definitions

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

As used herein, the singular form "a", "an", and "the" includes plural references unless indicated otherwise. For example, "a" target cell includes one or more target cells. By "subject" is meant an organism, which is a donor or recipient of explanted cells or the cells themselves. "Subject" also refers to an organism (including a mammal or a human) to which the nucleic acid molecules of the invention can be administered. In one embodiment, a subject is a mammal or mammalian cell. Mammals include, but are not limited to, humans, farm animals, sport animals, rodents and pets. In another embodiment, a subject is a human subject or human cell.

As used herein, an "effective amount" or a "sufficient amount" of a substance is that amount sufficient to effect beneficial or desired results, including clinical results, and, as such, an "effective amount" depends upon the context in which it is being applied. An effective amount can be administered in one or more administrations. In one aspect, the term "effective amount" refers to an amount of an inhibitory compound that when administered alone or in combination with an additional therapeutic agent to a cell, tissue, or subject is effective to prevent or ameliorate the symptoms of a cancer or the progression of the disease. In another aspect, an effective amount refers to that amount of an inhibitory compound that stabilizes degradation of a topoisomerase. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

As used herein, the term "amount sufficient to inhibit expression" refers to a concentration or amount of the dsRNA that is sufficient to reduce levels or stability of mRNA or protein produced from a target gene. As used herein, "inhibiting expression" refers to the absence or observable decrease in the level of protein and/or mRNA product from a target gene. Specificity refers to the ability to inhibit the target gene without manifest effects on other genes of the cell. The consequences of inhibition can be confirmed by examination of the outward properties of the cell or organism (such as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression can be conveniently assayed by use of a reporter or drug resistance gene whose protein product is easily assayed. Such reporter genes include alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows the determination of a degree of inhibition that is greater than 10%, 25%, 35%, 50%, 60%, 65%, 70%, 75%, 80%, 85%, 90%, 91%, 92%, 93%, 94%, 95%, 96%, 97%, 98% or 99% as compared to a cell not treated according to the present invention. Lower doses of injected material and longer times after administration of dsRNA may result in inhibition in a smaller fraction of cells (e.g., at least 10%, 15%, 20%, 25%, 30%, 35%, 40%, 45%, 50%, 75%, 90%, or 95% or more of targeted cells). Quantitation of gene expression in a cell may show similar amounts of inhibition at the level of accumulation of target mRNA or translation of target protein. As an example, the efficiency of inhibition may be determined by assessing the amount of gene product in the cell: mRNA may be detected with a hybridization probe having a nucleotide sequence outside the region used for the inhibitory dsRNA, or translated polypeptide may be detected with an antibody raised against the polypeptide sequence of that region.

As used herein, "to treat" or "therapeutic" and grammatically related terms refer to any improvement of any consequence of disease, such as prolonged survival, less morbidity, and/or a lessening of side effects which are the byproducts of an alternative therapeutic modality; full eradication of disease is not required. In one aspect, the administration of an inhibitory compound improves the efficacy of chemotherapy, preferably by increasing cell death or damage in response to a topoisomerase inhibitor. In another aspect, the inhibitory compound stabilizes a topoisomerase.

As used herein, "stabilizes a topoisomerase" refers to increasing protein or RNA levels encoded by a target gene in comparison to a subject that is not treated with the inhibitory compound. The increased protein or RNA levels can occur due to an increase in transcription or translation, a decrease in the rate of degradation, or a combination of these factors. In one aspect, the inhibitory compound decreases the rate of degradation of the topoisomerase.

As used herein, a "topoisomerase" refers to enzymes that act on the topology of DNA. Five human DNA topoisomerases have been identified and characterized: topoisomerase I (TOPI), topoisomerase IIα (TOPIIα), topoisomerase IIβ (TOPIIβ), topoisomerase IIIα (TOP3α), and topoisomerase IIIβ (TOP3β). Any human or mammalian topoisomerase may be stabilized by administration of the inhibitory compound. In one aspect, the inhibitory compound stabilizes TOPI, TOPII (α and/or β), or combinations thereof.

As used herein, a "topoisomerase inhibitor" is a compound that decreases the biological activity of one or more topoisomerase enzymes. Topoisomerase inhibitors are typically used to treat cancers, although they have other therapeutic applications. Any topoisomerase inhibitor can be used in conjunction with the inhibitory compound of the invention. Non-limiting examples of topoisomerase inhibitors include camptothecin, irinotecan, topotecan, doxorubicin, teniposide, etoposide, and analogs, derivatives, and combinations thereof. Topoisomerase inhibitors seem to be effective against several types of cancer, including but not limited to cardiac, lung, gastrointestinal, genitourinary tract, liver, bone, nervous system, gynecological, hematologic (such as acute lymphocytic leukemia or non-lymphocytic leukemia), skin, adrenal gland, breast, prostate, testicular, lymphoma, and glioblastoma multiforme. They can be administered in conjunction with other therapies, such as the inhibitory compounds of the current invention, chemotherapy, radiation, photodynamic therapy, immunotherapy, bone marrow transplants, gene therapy, hormone therapy, proton therapy, targeted therapy, and vaccine therapy.

As used herein, an "E3 ubiquitin ligase" is a protein or multi-protein complex that covalently attaches ubiquitin to a lysine residue on a target protein in order to label the target protein for degradation by the proteasome. The E3 ligase can receive the ubiquitin molecule from an E2 enzyme and transfer it to the target protein, or alternatively, can interact with both the E2 enzyme and the substrate but never itself receive the ubiquitin. If is a multi-protein complex, the term "E3 ubiquitin ligase" applies equally to any protein within that complex.

As used herein, the term "inhibitor compound" includes both protein and non-protein moieties. In some embodiments, the inhibitors are small molecules. Preferably, the inhibitors are compounds with sufficient specificity to avoid systemic toxicity. In other embodiments, the inhibitors are nucleotides.

As used herein, a compound is an "inhibitory compound" or an "E3 ubiquitin ligase inhibitor" when it is an inhibitor of one or more E3 ubiquitin ligases. It is an inhibitor of an E3 ubiquitin ligase when the compound reduces the expression or activity of the ligase relative to that observed in the absence of the inhibitory compound. In one aspect, the compound is an inhibitor of a gene encoding an E3 ubiquitin ligase. In other aspects, it is an inhibitor of the ligase itself. In one embodiment, a compound is an inhibitor of an E3 ubiquitin ligase when the compound increases cell damage or death in the presence of a topoisomerase inhibitor relative to the observed in the absence of the inhibitory compound. Cell death or damage can be assessed, for example, by examining levels of apoptosis, anti-tumor activity, or tumor metastasis (as ascertained by microscopic or macroscopic analysis). In another embodiment, the compound is an inhibitor of an E3 ubiquitin ligase when it stabilizes the degradation of a topoisomerase.

Salts and stereoisomers, including enantiomers, of the compounds disclosed herein are within the scope of the invention.

As used herein, a "salt" is salt of the instant compounds which has been modified by making acid or base salts of the compounds. The salt can be pharmaceutically acceptable. Examples of pharmaceutically acceptable salts include, but are not limited to, mineral or organic acid salts of basic residues such as amines; alkali or organic salts of acidic residues such as carboxcylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Carboxylate salts are the alkaline earth metal salts, sodium, potassium or lithium.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , or n carbons in a linear or branched arrangement, and specifically includes methyl, ethyl, propyl, butyl, pentyl, hexyl, and so on. For example, $C_1$-$C_6$, as in "C1-C6 alkyl" is defined to include individual moieties having 1, 2, 3, 4, 5, or 6 carbons in a linear or branched arrangement. "Alkoxy" represents an alkyl moiety of indicated number of carbon atoms which is attached to the core through an oxygen bridge such as —$C_x$—O—$C_y$ wherein x and y are independently carbons 1 through 6.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

If no number of carbon atoms is specified, the term "alkenyl" refers to a non-aromatic hydrocarbon radical, straight or branched, containing at least 1 carbon to carbon double bond, and up to the maximum possible number of non-aromatic carbon-carbon double bonds may be present.

The term "alkynyl" refers to a hydrocarbon radical straight or branched, containing at least 1 carbon to carbon triple bond, and up to the maximum possible number of non-aromatic carbon-carbon triple bonds may be present. Thus, "$C_2$-$C_6$ alkynyl" means an alkynyl radical radical having 2, 3, 4; 5, or 6 carbon atoms, and for example 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated.

In differing embodiments of alkyl as used herein the alkyl is a C1-C6 alkyl. In differing embodiments of alkenyl as used herein the alkenyl is a C2-C6 alkenyl. In differing embodiments of alkynyl as used herein the alkynyl is a C1-C6 alkynyl.

As used herein, "aryl" is intended to mean any stable monocyclic, bicyclic or tricyclic carbon ring of up to 10 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heterocyclic aryl", as used herein, represents a stable monocyclic or bicyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclic alkyl" as used herein is intended to mean a 5- to 10-membered nonaromatic ring containing from 1 to 4 heteroatoms selected from the group consisting of O, N and S, and includes bicyclic groups. "Heterocyclylic alkyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

The alkyl, alkenyl, alkynyl, cycloalkyl, aryl, heterocyclic aryl and heterocyclic alkyl substituents may be substituted or unsubstituted, unless specifically defined otherwise. For example, a ($C_1$-$C_7$)alkyl may be substituted with one or more substituents selected from OH, halogen, alkoxy, mono- or dialkylamino, or heterocyclic alkyl, such as morpholinyl, piperidinyl, and so on. "halogenated $C_1$-$C_6$ alkyl" is defined to include groups having 1 to 6 carbons in a linear or branched arrangement wherein each carbon can be independently substituted with 1, 2 or 3 halogens on each of $C_1$ to $C_6$ or on any of $C_1$ to $C_6$. In the compounds of the present invention, alkyl, alkenyl, cycloalkyl, heterocyclic alkyl, aryl and heterocyclic aryl groups can be further substituted by replacing one or more hydrogen atoms by alternative non-hydrogen groups. These include, but are not limited to, halo, hydroxy, mercapto, amino, carboxy, cyano and carbamoyl.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In embodiments of this invention, unsubstituted substituted aromatic rings include six-membered rings. In an embodiment the ring is substituted by a $C_1$-$C_{10}$ alkyl, alkenyl or alkynyl, each of which may be linear or branched, and each of which may be substituted themselves with one or more amino groups.

In an embodiment the alkyl, alkenyl or alkynyl, alkylene, alkenylene or alkynylene groups of this invention have 1, 2, 3, 4, 5, 6, 7, 8, 9 or 10 carbon atoms.

In choosing compounds of the present invention, one of ordinary skill in the art will recognize that the various substituents, i.e. $R_1$, $R_2$, and $R_3$, are to be chosen in conformity with well-known principles of chemical structure connectivity.

All combinations of the various elements disclosed herein are within the scope of the invention.

As used herein, the terms "contacting" and "administering" are used interchangeably, and refer to a process by which an inhibitory compound of the present invention is delivered to a cell, either in vitro, in vivo, or ex vivo, in order to silence a gene.

By "modulate" and "modulation" is meant that the expression of the target gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" and within the scope of the invention, the preferred form of modulation is inhibition but the use of the word "modulate" is not limited to this definition.

By "inhibit" it is meant that the levels of expression product or level of RNAs or equivalent RNAs encoding one or more gene products is reduced below that observed in the absence of the nucleic acid molecule of the invention. In one embodiment, inhibition with a siRNA molecule preferably is below that level observed in the presence of an inactive or attenuated molecule that is unable to mediate an RNAi response.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; and Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR). Single chain antibodies are also included by reference in the term "antibody."

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include non-expressed DNA segments that, for example, form recognition sequences for other proteins. "Genes" can be obtained from a variety of sources, including cloning from a source of interest or synthesizing from known or predicted sequence information, and may include sequences designed to have desired parameters. The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

By "target gene" is meant a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, more preferably an animal, and most preferably a human. Non-limiting examples of animals include vertebrates and invertebrates. In the context of the invention, "gene" or "target gene" is most an E3 ubiquitin ligase, such as, but not limited to Bmi1 and RING1.

The term "naturally occurring" is used to describe an object that can be found in nature as distinct from being artificially produced. For example, a protein or nucleotide sequence present in an organism (including a virus), which can be isolated from a source in nature and which has not been intentionally modified by a person in the laboratory, is naturally occurring.

The term "isolated" includes a material removed from its original environment, e.g., the natural environment if it is naturally occurring. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

The term "genome" refers to the complete genetic material of an organism.

By "target site" is meant a sequence within a target RNA that is "targeted" or cleavage mediated by a siRNA construct which contains sequences within its antisense region that are complementary to the target sequence.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells, and organisms comprising transgenic cells are referred to as "transgenic organisms".

The terms "transfection of cells" refer to the acquisition by a cell of new nucleic acid material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-facilitated microparticle bombardment (Johnston (1990)). Strontium phosphate DNA co-precipitation is also a transfection method.

The terms "transduction of cells" refer to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The terms "transformed", "transduced", "transgenic", and "recombinant" refer to a host cell or organism into which a heterologous nucleic acid molecule has been introduced. The nucleic acid molecule can be stably integrated into the genome generally known in the art and are disclosed in Sambrook, infra. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

The term "gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference. In some embodiments, gene silencing may be allele-specific. "Allele-specific" gene silencing refers to the specific silencing of one allele of a gene.

The term "RNA interference" (RNAi) refers to the process of sequence-specific, posttranscriptional gene silencing initiated by siRNA. RNAi is seen in a number of organisms such as *Drosophila*, nematodes, fungi and plants, and is believed to be involved in anti-viral defense, modulation of transposon activity, and regulation of gene expression. During RNAi, siRNA induces degradation of target mRNA with consequent sequence-specific inhibition of gene expression.

The phrases "small interfering RNA" or "short interfering RNA" or "siRNA" refer to a RNA duplex of nucleotides, or, in some alternative aspects, a single molecule of RNA (which can, in some embodiments, have secondary structure, such as loops) that is targeted to a nucleic acid, e.g., a gene, of interest. A "RNA duplex" refers to the structure formed by the complementary pairing between at least two regions of a RNA molecule. Thus, the "RNA duplex" can comprise one, two, three or more RNA molecules. siRNA is "targeted" to a gene in that the nucleotide sequence of the duplex portion of the siRNA is complementary to a nucleotide sequence of the targeted gene. Thus, by using the sequence of a target gene, any siRNA can be routinely designed and made. In some embodiments, the length of the duplex siRNA is less than 30 nucleotides. In some embodiments, the length of the duplex siRNA is more than 30 nucleotides. In some embodiments, the duplex can be 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 or 10 or fewer nucleotides in length. In some embodiments, the length of the duplex is 19-25 nucleotides in length. The RNA duplex portion of the siRNA can be part of a hairpin structure. In one aspect, there is no hairpin structure in a siRNA of the invention. In addition to the duplex portion, the hairpin structure may contain a loop portion positioned between the two sequences that form the duplex. The loop can vary in length. In some embodiments the loop is 2, 3, 4, 5, 6, 7, 8, 9, 10, 11, 12 or 13 or more nucleotides in length. The hairpin structure can also contain 3' or 5' overhang portions. In some embodiments, the overhang is a 3' or a 5' overhang 0, 1, 2, 3, 4 or 5 nucleotides in length. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal. The siRNA can be entirely, or in part, comprised of synthetic nucleotides, natural bases or modified bases.

"Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Certain vectors are capable of directing the expression of genes to which they are operatively linked. Such vectors are referred to herein as "expression vectors." Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

As used herein, the term "promoter" includes all sequences capable of driving transcription of a coding sequence in a cell, e.g., a plant cell or animal cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions.

"Tissue-specific" promoters are transcriptional control elements that are only active in particular cells or tissues or organs. Tissue-specific regulation may be achieved by certain intrinsic factors which ensure that genes encoding proteins specific to a given tissue are expressed. Such factors are known to exist in mammals so as to allow for specific tissues to develop.

The term "overexpression" refers to the level of expression in transgenic cells or organisms that exceeds levels of expression in normal or untransformed cells or organisms.

The phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides, naturally occurring nucleic acids, synthetic nucleic acids, and recombinant nucleic acids. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

As used herein, the term "recombinant" can include nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest.

In one aspect, the enriched nucleic acids represent 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more of the number of nucleic acid inserts in the population of recombinant backbone molecules.

"Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence can be "operably linked to" a coding sequence when RNA polymerase which initiates transcription at the promoter will transcribe the coding sequence into mRNA.

"Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

The phrase "substantially identical" in the context of two nucleic acids or polypeptides, can refer to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one any known sequence comparison algorithm, as discussed in detail below, or by visual inspection.

A "substantially identical" amino acid sequence also can include a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a polypeptide, resulting in modification of the structure of the polypeptide without significantly altering its biological activity.

"Variant" includes polynucleotides or polypeptides modified at one or more base pairs, codons, introns, exons, or amino acid residues (respectively) yet still retain the biological activity of a polypeptide of the naturally occurring sequence. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof.

"Hybridization" includes the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions as set forth herein.

In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example, 0.015 M sodium chloride/0.0015 M sodium citrate/0.1% sodium dodecyl sulfate at 50° C.; and/or (2) employ a denaturing agent such as formamide during hybridization, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

By complementarily or "complementary" it is meant that a nucleic acid can form hydrogen bond(s) with another nucleic acid sequence by either traditional Watson-Crick or other non-traditional types or precise pairing, such that stable and specific binding occurs between the oligonucleotide and the DNA or RNA target. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. As used herein, the term "substantially complementary" means that two nucleic acid sequences are complementary at least at 80% of their nucleotides. Preferably, the two nucleic acid sequences are complementary at least at 85%, 90%, 91%, 92%, 93%, 94%, 95%, 96%, 97%, 98%, 99% or more of their nucleotides. Alternatively, "substantially complementary" means that two nucleic acid sequences can hybridize under high stringency conditions. As used herein, the term "substantially identical" means that two nucleic acid sequences have at least 80% sequence identity. Preferably, the two nucleic acid sequences have at least 85%, 90%, 91%, 92%, 93%, 94%, 95%, 96%, 97%, 98%, 99% or 100% of sequence identity.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

By "pharmaceutically acceptable formulation" or "pharmaceutical composition" it is meant a composition or formulation that allows for the effective distribution of the inhibitory compounds of the invention in that physical location most suitable for their desired activity.

By "systemic administration" is meant in vivo systemic absorption or accumulation of a compound in the blood stream followed by distribution throughout the entire body.

The siRNA molecules of the invention can be administered to an individual in a dose corresponding to about 0.01 μg–100 mg/_kg body weight, preferably about 0.01 μg–10 mg/kg body weight, more preferably about 0.01 μg–1 mg/kg body weight and most preferably about 0.01 μg–0.1 mg/kg body weight.

Gene Suppression

The invention provides a method of suppressing or silencing genes in animal cells. In one aspect of the invention, the gene silencing is transcriptional. In another aspect of the invention, the animals are mammals, such as humans.

The invention specifically provides siRNAs that can be used to silence or suppress gene expression. Provided herein are compositions and methods of gene suppression in which target sequence specific siRNAs interact with target sequences and suppress gene expression. In one aspect of the invention, gene suppression is transcriptional gene expression. In particular, siRNAs enter the nuclear membrane of host cells and specifically target a sequence of interest. Marker or reporter genes and compounds can be used to monitor gene expression. Other methods and assays known in the art, including but not limited to computer-based methods, can be used to monitor gene expression. Any amount of reduction in transcription or gene expression is within the scope of the invention, including a decrease in anywhere from about 1% to 100%.

Target Sequences

In one aspect of the method of gene silencing provided herein, target sequences are identified. Target sequences are sequences that are targeted, recognized, and/or bound by siRNAs. Target sequences include, but are not limited to, nucleic acids and proteins or derivatives, variants, or portions thereof. In one aspect of the invention, target sequences include promoter, intronic, and exonic sequences. In one aspect of the invention, the target sequences encode an E3 ubiquitin ligase. In another aspect, E3 ubiquitin ligase is Bmi1 and/or RING1. In a further aspect, the E3 ubiquitin ligase is targeted by siRNA.

Promoters include, but are not limited to, CMV immediate early, HSV thymidine kinase, early and late SV40, LTRs from retrovirus, and mouse metallothionein I, heat shock promoters, and LTRs from retroviruses. Other promoters known to control expression of genes in prokaryotic or eukaryotic cells or their viruses may also be used.

In another aspect of the invention, the target sequences include a reporter or marker gene. The reporter or marker gene is used to monitor gene expression. In particular, the reporter or marker gene is used to monitor gene suppression or silencing. In one aspect of the invention, the reporter gene is green fluorescent protein. Any compound, label, or gene that has a reporting or marking function can be used in the methods provided herein.

In another aspect of the invention, target sequences are inserted into the genome of a host cell by e.g. a vector. A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and PSVL (Pharmacia). However, any other vector may be used as long as it is replicable and viable in the host cell.

Obtaining siRNA and Target Sequences

The nucleic acids of the invention, including siRNA and nucleic acids that encode them, can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

The nucleic acids used to practice this invention, whether RNA, iRNA, siRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066. Alternatively, nucleic acids can be obtained from commercial sources.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Ausubel, ed. John Wiley & Sons, Inc., New York (1997); Laboratory Techniques in Biochemistry and Molecular Biology: Hybridization with Nucleic Acid Probes, Part I. Theory and Nucleic Acid Preparation, Tijssen, ed. Elsevier, N.Y. (1993); Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In practicing the invention, nucleic acids of the invention or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library is amplified.

The skilled artisan can select and design suitable oligonucleotide amplification primers. Amplification methods are also well known in the art, and include, e.g., polymerase chain reaction, PCR (see, e.g., PCR Protocols, A Guide to Methods and Applications, ed. Innis, Academic Press, N.Y. (1990) and PCR Strategies (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990)

Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; and Sooknanan (1995) Biotechnology 13:563-564.

Cells

The invention also provides cells whose gene expression has been silenced using the methods or compositions of the invention. In one aspect of the invention, cells have gene expression that has been transcriptionally silenced. The cells whose genes have been transcriptionally silenced include animal cells. Animal cells include mammalian cells, such as human cells. Exemplary animal cells include CHO, COS, HeLa, HT29, or any mouse or human cell line, either in vitro, ex vivo, or in vivo. The selection of an appropriate host is within the abilities of those skilled in the art.

Where appropriate, host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to interact with siRNAs.

In other aspects, the cells whose genes have been silenced are present in the host animal.

siRNAs siRNAs used in the methods provided herein can be obtained from a variety of sources, as described herein. siRNAs can contain from about 1 to about 200 nucleotides, from about 5 to about 100 nucleotides, from about 10 to about 50 nucleotides, from about 15 to about 30 nucleotides, or from about 19 to about 25 nucleotides.

The dsRNA of the invention may comprise one or more strands of polymerized ribonucleotide; it may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms that is generated by dsRNA. Likewise, bases may be modified to block the activity of adenosine deaminase. RNA may be produced enzymatically or by partial/total organic synthesis, any modified ribonucleotide can be introduced by in vitro enzymatic or organic synthesis.

The double-stranded structure may be formed by a single self-complementary RNA strand (i.e. forming a hairpin loop) or two complementary RNA strands. RNA duplex formation may be initiated either inside or outside the cell. The RNA may be introduced in an amount that allows delivery of at least one copy per cell. Higher doses of double-stranded material may yield more effective inhibition.

In one aspect of the invention provided herein, siRNAs have perfect homology with target sequences to effect target specific responses. In another aspect of the invention, siRNAs have about 99%, 98%, 97%, 96%, 95%, 94%, 92%, 91%, 90%, 88%, 86%, 84%, 82%, 80%, 78%, 76%, 74%, 72%, 70%, 65%, 60%, 55%, 50%, 45%, 40%, 35%, 30%, 25%, 20%, 15%, 10%, or 5% homology with target sequences. In another aspect of the invention, siRNAs target more than one target sequence and target marker or reporter genes. The extent of sequence identity (homology) may be determined using any computer program and associated parameters, including those described herein, such as BLAST 2.2.2. or FASTA version 3.0t78, with the default parameters. It is to be understood that for the purposes of determining sequence identity, when comparing a DNA sequence to an RNA sequence, a thymidine nucleotide is equivalent to a uracil nucleotide.

Homology or sequence identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence, e.g., a sequence of the invention, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Entry of siRNAs into the Nucleus

In one aspect of the invention, target sequence specific siRNAs are designed to enter (pass through) nuclear membranes and thereby silence gene expression. In various aspects of the methods and compositions of the invention, entry into the nucleus is effected by macromolecular transport processes across the nuclear envelope, vectors capable of transporting nucleic acids into a nucleus, e.g., a viral vector, such as a lentiviral vector, nuclear-transport mediating peptides, electroporation, lipid vesicles, MPG, or a combination thereof, including all techniques known in the art, see, e.g., Morris, M. C., Vidal, P., Chaloin, L., Heitz, F. & Divita, G. A new peptide vector for efficient delivery of oligonucleotides into mammalian cells. Nucleic Acids Res 25: 2730-6 (1997)), including any transfecting agent known in the art, see, e.g., Davis, L., Dibner, M., Battey, I., Basic Methods in Molecular Biology, (1986).

Macromolecular transport processes across the nuclear envelope are known in the art and a large number of soluble transport receptors mediating either nuclear import or nuclear export have been identified. Most of these receptors belong to one large family of proteins, all of which share homology with the protein import receptor importin β (also named karyopherin β). Members of this family have been classified as importins or exportins on the basis of the direction they carry their cargo. To date, the family includes 14 members in the yeast Saccharomyces cerevisiae and at least 22 members in humans. In addition to comprising importin β (karyopherin β) as macromolecular transport compositions, some aspects of the invention can comprise SV40 T antigen nuclear localization signal, Human LEDGF/p75 protein, nucleoporins and transport factors, or any other macromolecular transport process. See, e.g., Yasuhara, Exp Cell Res. 2004 Jul. 1; 297(1): 285-93; Maertens, J Biol. Chem. 2004 May 25; Zolotukhin, J. Virol. 1999 Jan.; 73(1):120-7.

Application of Gene Silencing

The invention provides compositions and methods to inhibit gene expression of a target sequence or gene for disease treatment. Genes of interest that can be inhibited using a composition or method of the invention include, but are not limited to, genes associated with cancer or genes associated with a response to a cancer treatment. In one aspect, the gene associated with a response to a cancer treatment encodes an E3 ubiquitin ligase, such as, but not limited to, Bmi1 and/or RING1. Thus, the invention also provides siRNAs that target genes associated with a response to a cancer treatment. The methods provided herein may be practiced in vitro, ex vivo or in vivo.

In one aspect of the invention, the siRNA silences an E3 ubiquitin ligase. In another aspect, the siRNA silences Bmi1 and/or RING1, which are E3 ubiquitin ligases. The nucleotide sequence of human Bmi1 is found at NM_005180.5, and the nucleotide sequence of human RING1 is found at NM_002931.3. Accordingly, exemplary siRNA include siRNA selected from the group consisting of (a) a dsRNA molecule having a first strand comprising the sequence set forth in SEQ ID NO:3 and the second strand comprising the sequence set forth in SEQ ID NO:4; (b) a dsRNA molecule having a first strand comprising the sequence set forth in SEQ ID NO:5 and the second strand comprising the sequence set forth in SEQ ID NO:6; (c) a dsRNA molecule having a first strand comprising the sequence set forth in SEQ ID NO:7 and the second strand comprising the sequence set forth in SEQ ID NO:8; (d) a dsRNA molecule having a first strand comprising the sequence set forth in SEQ ID NO:9 and the second strand comprises the sequence set forth in SEQ ID NO:10; and (e) combinations thereof. Other exemplary siRNA sequences are shown in the following tables, which are readily tested for gene silencing activity as set out herein, and are fragments of Bmi1 and RING1.

TABLE 1

Candidate cDNA target sequences for silencing Bmi1.

| Start Position relative to NM_005180.5 | N19 target | N25 extended target |
| --- | --- | --- |
| 1 | AAATGCATCGAACAACGAGAA (SEQ ID NO: 13) | ATGCATCGAACAACGAGAATCAAGA (SEQ ID NO: 14) |
| 125 | GTGTATTGTTCGTTACCTGGA (SEQ ID NO: 15) | GTATTGTTCGTTACCTGGAGACCAG (SEQ ID NO: 16) |
| 126 | TGTATTGTTCGTTACCTGGAG (SEQ ID NO: 17) | TATTGTTCGTTACCTGGAGACCAGC (SEQ ID NO: 18) |
| 127 | GTATTGTTCGTTACCTGGAGA (SEQ ID NO: 19) | ATTGTTCGTTACCTGGAGACCAGCA (SEQ ID NO: 20) |
| 129 | ATTGTTCGTTACCTGGAGACC (SEQ ID NO: 21) | TGTTCGTTACCTGGAGACCAGCAAG (SEQ ID NO: 22) |
| 131 | TGTTCGTTACCTGGAGACCAG (SEQ ID NO: 23) | TTCGTTACCTGGAGACCAGCAAGTA (SEQ ID NO: 24) |
| 149 | CAGCAAGTATTGTCCTATTTG (SEQ ID NO: 25) | GCAAGTATTGTCCTATTTGTGATGT (SEQ ID NO: 26) |
| 164 | TATTTGTGATGTCCAAGTTCA (SEQ ID NO: 27) | TTTGTGATGTCCAAGTTCACAAGAC (SEQ ID NO: 28) |
| 165 | ATTTGTGATGTCCAAGTTCAC (SEQ ID NO: 29) | TTGTGATGTCCAAGTTCACAAGACC (SEQ ID NO: 30) |
| 166 | TTTGTGATGTCCAAGTTCACA (SEQ ID NO: 31) | TGTGATGTCCAAGTTCACAAGACCA (SEQ ID NO: 32) |
| 169 | GTGATGTCCAAGTTCACAAGA (SEQ ID NO: 33) | GATGTCCAAGTTCACAAGACCAGAC (SEQ ID NO: 34) |
| 17 | GAGAATCAAGATCACTGAGCT (SEQ ID NO: 35) | GAATCAAGATCACTGAGCTAAATCC (SEQ ID NO: 36) |
| 171 | GATGTCCAAGTTCACAAGACC (SEQ ID NO: 37) | TGTCCAAGTTCACAAGACCAGACCA (SEQ ID NO: 38) |
| 179 | AGTTCACAAGACCAGACCACT (SEQ ID NO: 39) | TTCACAAGACCAGACCACTACTGAA (SEQ ID NO: 40) |
| 180 | GTTCACAAGACCAGACCACTA (SEQ ID NO: 41) | TCACAAGACCAGACCACTACTGAAT (SEQ ID NO: 42) |
| 195 | CCACTACTGAATATAAGGTCA (SEQ ID NO: 43) | ACTACTGAATATAAGGTCAGATAAA (SEQ ID NO: 44) |

TABLE 1-continued

Candidate cDNA target sequences for silencing Bmi1.

| Start Position relative to NM_005180.5 | N19 target | N25 extended target |
|---|---|---|
| 2 | AATGCATCGAACAACGAGAAT (SEQ ID NO: 45) | TGCATCGAACAACGAGAATCAAGAT (SEQ ID NO: 46) |
| 219 | AAAACTCTCCAAGATATTGTA (SEQ ID NO: 47) | AACTCTCCAAGATATTGTATACAAA (SEQ ID NO: 48) |
| 240 | TACAAATTAGTTCCAGGGCTT (SEQ ID NO: 49) | CAAATTAGTTCCAGGGCTTTTCAAA (SEQ ID NO: 50) |
| 241 | ACAAATTAGTTCCAGGGCTTT (SEQ ID NO: 51) | AAATTAGTTCCAGGGCTTTTCAAAA (SEQ ID NO: 52) |
| 265 | AAAATGAAATGAAGAGAAGAA (SEQ ID NO: 53) | AATGAAATGAAGAGAAGAAGGGATT (SEQ ID NO: 54) |
| 297 | GCAGCTCATCCTTCTGCTGAT (SEQ ID NO: 55) | AGCTCATCCTTCTGCTGATGCTGCC (SEQ ID NO: 56) |
| 304 | ATCCTTCTGCTGATGCTGCCA (SEQ ID NO: 57) | CCTTCTGCTGATGCTGCCAATGGCT (SEQ ID NO: 58) |
| 305 | TCCTTCTGCTGATGCTGCCAA (SEQ ID NO: 59) | CTTCTGCTGATGCTGCCAATGGCTC (SEQ ID NO: 60) |
| 308 | TTCTGCTGATGCTGCCAATGG (SEQ ID NO: 61) | CTGCTGATGCTGCCAATGGCTCTAA (SEQ ID NO: 62) |
| 309 | TCTGCTGATGCTGCCAATGGC (SEQ ID NO: 63) | TGCTGATGCTGCCAATGGCTCTAAT (SEQ ID NO: 64) |
| 336 | GAAGATAGAGGAGAGGTTGCA (SEQ ID NO: 65) | AGATAGAGGAGAGGTTGCAGATGAA (SEQ ID NO: 66) |
| 389 | GATAATAAGCTTATCCATTGA (SEQ ID NO: 67) | TAATAAGCTTATCCATTGAATTCTT (SEQ ID NO: 68) |
| 394 | TAAGCTTATCCATTGAATTCT (SEQ ID NO: 69) | AGCTTATCCATTGAATTCTTTGACC (SEQ ID NO: 70) |
| 4 | TGCATCGAACAACGAGAATCA (SEQ ID NO: 71) | CATCGAACAACGAGAATCAAGATCA (SEQ ID NO: 72) |
| 423 | AACAGATTGGATCGGAAAGTA (SEQ ID NO: 73) | CAGATTGGATCGGAAAGTAAACAAA (SEQ ID NO: 74) |
| 424 | ACAGATTGGATCGGAAAGTAA (SEQ ID NO: 75) | AGATTGGATCGGAAAGTAAACAAAG (SEQ ID NO: 76) |
| 425 | CAGATTGGATCGGAAAGTAAA (SEQ ID NO: 77) | GATTGGATCGGAAAGTAAACAAAGA (SEQ ID NO: 78) |
| 427 | GATTGGATCGGAAAGTAAACA (SEQ ID NO: 79) | TTGGATCGGAAAGTAAACAAAGACA (SEQ ID NO: 80) |
| 428 | ATTGGATCGGAAAGTAAACAA (SEQ ID NO: 81) | TGGATCGGAAAGTAAACAAAGACAA (SEQ ID NO: 82) |
| 429 | TTGGATCGGAAAGTAAACAAA (SEQ ID NO: 83) | GGATCGGAAAGTAAACAAAGACAAA (SEQ ID NO: 84) |
| 437 | GAAAGTAAACAAAGACAAAGA (SEQ ID NO: 85) | AAGTAAACAAAGACAAAGAGAAATC (SEQ ID NO: 86) |
| 439 | AAGTAAACAAAGACAAAGAGA (SEQ ID NO: 87) | GTAAACAAAGACAAAGAGAAATCTA (SEQ ID NO: 88) |
| 441 | GTAAACAAAGACAAAGAGAAA (SEQ ID NO: 89) | AAACAAAGACAAAGAGAAATCTAAG (SEQ ID NO: 90) |
| 445 | ACAAAGACAAAGAGAAATCTA (SEQ ID NO: 91) | AAAGACAAAGAGAAATCTAAGGAGG (SEQ ID NO: 92) |

TABLE 1-continued

Candidate cDNA target sequences for silencing Bmi1.

| Start Position relative to NM_005180.5 | N19 target | N25 extended target |
|---|---|---|
| 446 | CAAAGACAAAGAGAAATCTAA (SEQ ID NO: 93) | AAGACAAAGAGAAATCTAAGGAGGA (SEQ ID NO: 94) |
| 447 | AAAGACAAAGAGAAATCTAAG (SEQ ID NO: 95) | AGACAAAGAGAAATCTAAGGAGGAG (SEQ ID NO: 96) |
| 457 | AGAAATCTAAGGAGGAGGTGA (SEQ ID NO: 97) | AAATCTAAGGAGGAGGTGAATGATA (SEQ ID NO: 98) |
| 458 | GAATCTAAGGAGGAGGTGAA (SEQ ID NO: 99) | AATCTAAGGAGGAGGTGAATGATAA (SEQ ID NO: 100) |
| 482 | TAAAAGATACTTACGATGCCC (SEQ ID NO: 101) | AAAGATACTTACGATGCCCAGCAGC (SEQ ID NO: 102) |
| 484 | AAAGATACTTACGATGCCCAG (SEQ ID NO: 103) | AGATACTTACGATGCCCAGCAGCAA (SEQ ID NO: 104) |
| 486 | AGATACTTACGATGCCCAGCA (SEQ ID NO: 105) | ATACTTACGATGCCCAGCAGCAATG (SEQ ID NO: 106) |
| 487 | GATACTTACGATGCCCAGCAG (SEQ ID NO: 107) | TACTTACGATGCCCAGCAGCAATGA (SEQ ID NO: 108) |
| 510 | ATGACTGTGATGCACTTAAGA (SEQ ID NO: 109) | GACTGTGATGCACTTAAGAAAGTTT (SEQ ID NO: 110) |
| 526 | TAAGAAAGTTTCTCAGAAGTA (SEQ ID NO: 111) | AGAAAGTTTCTCAGAAGTAAAATGG (SEQ ID NO: 112) |
| 546 | AAAATGGACATACCTAATACT (SEQ ID NO: 113) | AATGGACATACCTAATACTTTCCAG (SEQ ID NO: 114) |
| 547 | AAATGGACATACCTAATACTT (SEQ ID NO: 115) | ATGGACATACCTAATACTTTCCAGA (SEQ ID NO: 116) |
| 548 | AATGGACATACCTAATACTTT (SEQ ID NO: 117) | TGGACATACCTAATACTTTCCAGAT (SEQ ID NO: 118) |
| 549 | ATGGACATACCTAATACTTTC (SEQ ID NO: 119) | GGACATACCTAATACTTTCCAGATT (SEQ ID NO: 120) |
| 550 | TGGACATACCTAATACTTTCC (SEQ ID NO: 121) | GACATACCTAATACTTTCCAGATTG (SEQ ID NO: 122) |
| 551 | GGACATACCTAATACTTTCCA (SEQ ID NO: 123) | ACATACCTAATACTTTCCAGATTGA (SEQ ID NO: 124) |
| 580 | TCATGTATGAGGAGGAACCTT (SEQ ID NO: 125) | ATGTATGAGGAGGAACCTTTAAAGG (SEQ ID NO: 126) |
| 583 | TGTATGAGGAGGAACCTTTAA (SEQ ID NO: 127) | TATGAGGAGGAACCTTTAAAGGATT (SEQ ID NO: 128) |
| 618 | CTAATGGATATTGCCTACATT (SEQ ID NO: 129) | AATGGATATTGCCTACATTTATACC (SEQ ID NO: 130) |
| 634 | ACATTTATACCTGGAGAAGGA (SEQ ID NO: 131) | ATTTATACCTGGAGAAGGAATGGTC (SEQ ID NO: 132) |
| 635 | CATTTATACCTGGAGAAGGAA (SEQ ID NO: 133) | TTTATACCTGGAGAAGGAATGGTCC (SEQ ID NO: 134) |
| 642 | ACCTGGAGAAGGAATGGTCCA (SEQ ID NO: 135) | CTGGAGAAGGAATGGTCCACTTCCA (SEQ ID NO: 136) |
| 665 | TCCATTGAAATACAGAGTTCG (SEQ ID NO: 137) | CATTGAAATACAGAGTTCGACCTAC (SEQ ID NO: 138) |
| 666 | CCATTGAAATACAGAGTTCGA (SEQ ID NO: 139) | ATTGAAATACAGAGTTCGACCTACT (SEQ ID NO: 140) |

TABLE 1-continued

Candidate cDNA target sequences for silencing Bmi1.

| Start Position relative to NM_005180.5 | N19 target | N25 extended target |
|---|---|---|
| 675 | TACAGAGTTCGACCTACTTGT (SEQ ID NO: 141) | CAGAGTTCGACCTACTTGTAAAAGA (SEQ ID NO: 142) |
| 704 | GAAGATCAGTCACCAGAGAGA (SEQ ID NO: 143) | AGATCAGTCACCAGAGAGATGGACT (SEQ ID NO: 144) |
| 705 | AAGATCAGTCACCAGAGAGAT (SEQ ID NO: 145) | GATCAGTCACCAGAGAGATGGACTG (SEQ ID NO: 146) |
| 77 | CATTGATGCCACAACCATAAT (SEQ ID NO: 147) | TTGATGCCACAACCATAATAGAATG (SEQ ID NO: 148) |
| 78 | ATTGATGCCACAACCATAATA (SEQ ID NO: 149) | TGATGCCACAACCATAATAGAATGT (SEQ ID NO: 150) |
| 80 | TGATGCCACAACCATAATAGA (SEQ ID NO: 151) | ATGCCACAACCATAATAGAATGTCT (SEQ ID NO: 152) |
| 838 | TGCAGTCTCCTCATCCACAGT (SEQ ID NO: 153) | CAGTCTCCTCATCCACAGTTTCCTC (SEQ ID NO: 154) |
| 841 | AGTCTCCTCATCCACAGTTTC (SEQ ID NO: 155) | TCTCCTCATCCACAGTTTCCTCACA (SEQ ID NO: 156) |
| 868 | TTTCCAGTACTATGAATGGAA (SEQ ID NO: 157) | TCCAGTACTATGAATGGAACCAGCA (SEQ ID NO: 158) |
| 869 | TTCCAGTACTATGAATGGAAC (SEQ ID NO: 159) | CCAGTACTATGAATGGAACCAGCAA (SEQ ID NO: 160) |
| 871 | CCAGTACTATGAATGGAACCA (SEQ ID NO: 161) | AGTACTATGAATGGAACCAGCAACA (SEQ ID NO: 162) |
| 873 | AGTACTATGAATGGAACCAGC (SEQ ID NO: 163) | TACTATGAATGGAACCAGCAACAGC (SEQ ID NO: 164) |
| 923 | TTTTGCCAATAGACCTCGAAA (SEQ ID NO: 165) | TTGCCAATAGACCTCGAAAATCATC (SEQ ID NO: 166) |
| 949 | CAGTAAATGGGTCATCAGCAA (SEQ ID NO: 167) | GTAAATGGGTCATCAGCAACTTCTT (SEQ ID NO: 168) |
| 950 | AGTAAATGGGTCATCAGCAAC (SEQ ID NO: 169) | TAAATGGGTCATCAGCAACTTCTTC (SEQ ID NO: 170) |
| 953 | AAATGGGTCATCAGCAACTTC (SEQ ID NO: 171) | ATGGGTCATCAGCAACTTCTTCTGG (SEQ ID NO: 172) |

TABLE 2

Candidate cDNA target sequences for silencing RING1.

| Start Position relative to NM_02931.3 | N19 target | N25 extended target |
|---|---|---|
| 114 | TCCCCTCGGTCACTGCATTCA (SEQ ID NO: 173) | CCCCTCGGTCACTGCATTCAGAACTC (SEQ ID NO: 174) |
| 115 | CCCCTCGGTCACTGCATTCAG (SEQ ID NO: 175) | CCTCGGTCACTGCATTCAGAACTCA (SEQ ID NO: 176) |
| 116 | CCCTCGGTCACTGCATTCAGA (SEQ ID NO: 177) | CTCGGTCACTGCATTCAGAACTCAT (SEQ ID NO: 178) |
| 121 | GGTCACTGCATTCAGAACTCA (SEQ ID NO: 179) | TCACTGCATTCAGAACTCATGTGCC (SEQ ID NO: 180) |
| 122 | GTCACTGCATTCAGAACTCAT (SEQ ID NO: 181) | CACTGCATTCAGAACTCATGTGCCC (SEQ ID NO: 182) |

TABLE 2-continued

Candidate cDNA target sequences for silencing RING1.

| Start Position relative to NM_02931.3 | N19 target | N25 extended target |
|---|---|---|
| 123 | TCACTGCATTCAGAACTCATG (SEQ ID NO: 183) | ACTGCATTCAGAACTCATGTGCCCT (SEQ ID NO: 184) |
| 127 | TGCATTCAGAACTCATGTGCC (SEQ ID NO: 185) | CATTCAGAACTCATGTGCCCTATCT (SEQ ID NO: 186) |
| 129 | CATTCAGAACTCATGTGCCCT (SEQ ID NO: 187) | TTCAGAACTCATGTGCCCTATCTGC (SEQ ID NO: 188) |
| 130 | ATTCAGAACTCATGTGCCCTA (SEQ ID NO: 189) | TCAGAACTCATGTGCCCTATCTGCC (SEQ ID NO: 190) |
| 165 | CTGAAGAATACGATGACCACC (SEQ ID NO: 191) | GAAGAATACGATGACCACCAAGGAG (SEQ ID NO: 192) |
| 166 | TGAAGAATACGATGACCACCA (SEQ ID NO: 193) | AAGAATACGATGACCACCAAGGAGT (SEQ ID NO: 194) |
| 167 | GAAGAATACGATGACCACCAA (SEQ ID NO: 195) | AGAATACGATGACCACCAAGGAGTG (SEQ ID NO: 196) |
| 170 | GAATACGATGACCACCAAGGA (SEQ ID NO: 197) | ATACGATGACCACCAAGGAGTGCCT (SEQ ID NO: 198) |
| 179 | GACCACCAAGGAGTGCCTCCA (SEQ ID NO: 199) | CCACCAAGGAGTGCCTCCACAGATT (SEQ ID NO: 200) |
| 180 | ACCACCAAGGAGTGCCTCCAC (SEQ ID NO: 201) | CACCAAGGAGTGCCTCCACAGATTC (SEQ ID NO: 202) |
| 181 | CCACCAAGGAGTGCCTCCACA (SEQ ID NO: 203) | ACCAAGGAGTGCCTCCACAGATTCT (SEQ ID NO: 204) |
| 187 | AGGAGTGCCTCCACAGATTCT (SEQ ID NO: 205) | GAGTGCCTCCACAGATTCTGCTCTG (SEQ ID NO: 206) |
| 198 | CACAGATTCTGCTCTGACTGC (SEQ ID NO: 207) | CAGATTCTGCTCTGACTGCATTGTC (SEQ ID NO: 208) |
| 207 | TGCTCTGACTGCATTGTCACA (SEQ ID NO: 209) | CTCTGACTGCATTGTCACAGCCCTA (SEQ ID NO: 210) |
| 209 | CTCTGACTGCATTGTCACAGC (SEQ ID NO: 211) | CTGACTGCATTGTCACAGCCCTACG (SEQ ID NO: 212) |
| 212 | TGACTGCATTGTCACAGCCCT (SEQ ID NO: 213) | ACTGCATTGTCACAGCCCTACGGAG (SEQ ID NO: 214) |
| 213 | GACTGCATTGTCACAGCCCTA (SEQ ID NO: 215) | CTGCATTGTCACAGCCCTACGGAGC (SEQ ID NO: 216) |
| 214 | ACTGCATTGTCACAGCCCTAC (SEQ ID NO: 217) | TGCATTGTCACAGCCCTACGGAGCG (SEQ ID NO: 218) |
| 215 | CTGCATTGTCACAGCCCTACG (SEQ ID NO: 219) | GCATTGTCACAGCCCTACGGAGCGG (SEQ ID NO: 220) |
| 217 | GCATTGTCACAGCCCTACGGA (SEQ ID NO: 221) | ATTGTCACAGCCCTACGGAGCGGGA (SEQ ID NO: 222) |
| 219 | ATTGTCACAGCCCTACGGAGC (SEQ ID NO: 223) | TGTCACAGCCCTACGGAGCGGGAAC (SEQ ID NO: 224) |
| 227 | AGCCCTACGGAGCGGGAACAA (SEQ ID NO: 225) | CCCTACGGAGCGGGAACAAGGAGTG (SEQ ID NO: 226) |
| 228 | GCCCTACGGAGCGGGAACAAG (SEQ ID NO: 227) | CCTACGGAGCGGGAACAAGGAGTGT (SEQ ID NO: 228) |
| 230 | CCTACGGAGCGGGAACAAGGA (SEQ ID NO: 229) | TACGGAGCGGGAACAAGGAGTGTCC (SEQ ID NO: 230) |

TABLE 2-continued

Candidate cDNA target sequences for silencing RING1.

| Start Position relative to NM_02931.3 | N19 target | N25 extended target |
|---|---|---|
| 237 | AGCGGGAACAAGGAGTGTCCT (SEQ ID NO: 231) | CGGGAACAAGGAGTGTCCTACCTGC (SEQ ID NO: 232) |
| 238 | GCGGGAACAAGGAGTGTCCTA (SEQ ID NO: 233) | GGGAACAAGGAGTGTCCTACCTGCC (SEQ ID NO: 234) |
| 239 | CGGGAACAAGGAGTGTCCTAC (SEQ ID NO: 235) | GGAACAAGGAGTGTCCTACCTGCCG (SEQ ID NO: 236) |
| 240 | GGGAACAAGGAGTGTCCTACC (SEQ ID NO: 237) | GAACAAGGAGTGTCCTACCTGCCGA (SEQ ID NO: 238) |
| 244 | ACAAGGAGTGTCCTACCTGCC (SEQ ID NO: 239) | AAGGAGTGTCCTACCTGCCGAAAGA (SEQ ID NO: 240) |
| 250 | AGTGTCCTACCTGCCGAAAGA (SEQ ID NO: 241) | TGTCCTACCTGCCGAAAGAAGCTGG (SEQ ID NO: 242) |
| 251 | GTGTCCTACCTGCCGAAAGAA (SEQ ID NO: 243) | GTCCTACCTGCCGAAAGAAGCTGGT (SEQ ID NO: 244) |
| 252 | TGTCCTACCTGCCGAAAGAAG (SEQ ID NO: 245) | TCCTACCTGCCGAAAGAAGCTGGTG (SEQ ID NO: 246) |
| 253 | GTCCTACCTGCCGAAAGAAGC (SEQ ID NO: 247) | CCTACCTGCCGAAAGAAGCTGGTGT (SEQ ID NO: 248) |
| 269 | GAAGCTGGTGTCCAAGCGATC (SEQ ID NO: 249) | AGCTGGTGTCCAAGCGATCCCTACG (SEQ ID NO: 250) |
| 272 | GCTGGTGTCCAAGCGATCCCT (SEQ ID NO: 251) | TGGTGTCCAAGCGATCCCTACGGCC (SEQ ID NO: 252) |
| 273 | CTGGTGTCCAAGCGATCCCTA (SEQ ID NO: 253) | GGTGTCCAAGCGATCCCTACGGCCA (SEQ ID NO: 254) |
| 274 | TGGTGTCCAAGCGATCCCTAC (SEQ ID NO: 255) | GTGTCCAAGCGATCCCTACGGCCAG (SEQ ID NO: 256) |
| 275 | GGTGTCCAAGCGATCCCTACG (SEQ ID NO: 257) | TGTCCAAGCGATCCCTACGGCCAGA (SEQ ID NO: 258) |
| 279 | TCCAAGCGATCCCTACGGCCA (SEQ ID NO: 259) | CAAGCGATCCCTACGGCCAGACCCC (SEQ ID NO: 260) |
| 280 | CCAAGCGATCCCTACGGCCAG (SEQ ID NO: 261) | AAGCGATCCCTACGGCCAGACCCCA (SEQ ID NO: 262) |
| 281 | CAAGCGATCCCTACGGCCAGA (SEQ ID NO: 263) | AGCGATCCCTACGGCCAGACCCCAA (SEQ ID NO: 264) |
| 307 | ACTTTGATGCCCTGATCTCTA (SEQ ID NO: 265) | TTTGATGCCCTGATCTCTAAGATCT (SEQ ID NO: 266) |
| 319 | TGATCTCTAAGATCTATCCTA (SEQ ID NO: 267) | ATCTCTAAGATCTATCCTAGCCGGG (SEQ ID NO: 268) |
| 320 | GATCTCTAAGATCTATCCTAG (SEQ ID NO: 269) | TCTCTAAGATCTATCCTAGCCGGGA (SEQ ID NO: 270) |
| 321 | ATCTCTAAGATCTATCCTAGC (SEQ ID NO: 271) | CTCTAAGATCTATCCTAGCCGGGAG (SEQ ID NO: 272) |
| 324 | TCTAAGATCTATCCTAGCCGG (SEQ ID NO: 273) | TAAGATCTATCCTAGCCGGGAGGAA (SEQ ID NO: 274) |
| 325 | CTAAGATCTATCCTAGCCGGG (SEQ ID NO: 275) | AAGATCTATCCTAGCCGGGAGGAAT (SEQ ID NO: 276) |
| 326 | TAAGATCTATCCTAGCCGGGA (SEQ ID NO: 277) | AGATCTATCCTAGCCGGGAGGAATA (SEQ ID NO: 278) |

TABLE 2-continued

Candidate cDNA target sequences for silencing RING1.

Start Position relative to NM_02931.3 | N19 target | N25 extended target
---|---|---
327 | AAGATCTATCCTAGCCGGGAG (SEQ ID NO: 279) | GATCTATCCTAGCCGGGAGGAATAC (SEQ ID NO: 280)
329 | GATCTATCCTAGCCGGGAGGA (SEQ ID NO: 281) | TCTATCCTAGCCGGGAGGAATACGA (SEQ ID NO: 282)
330 | ATCTATCCTAGCCGGGAGGAA (SEQ ID NO: 283) | CTATCCTAGCCGGGAGGAATACGAG (SEQ ID NO: 284)
332 | CTATCCTAGCCGGGAGGAATA (SEQ ID NO: 285) | ATCCTAGCCGGGAGGAATACGAGGC (SEQ ID NO: 286)
349 | AATACGAGGCCCATCAAGACC (SEQ ID NO: 287) | TACGAGGCCCATCAAGACCGAGTGC (SEQ ID NO: 288)
351 | TACGAGGCCCATCAAGACCGA (SEQ ID NO: 289) | CGAGGCCCATCAAGACCGAGTGCTT (SEQ ID NO: 290)
360 | CATCAAGACCGAGTGCTTATC (SEQ ID NO: 291) | TCAAGACCGAGTGCTTATCCGCCTG (SEQ ID NO: 292)
364 | AAGACCGAGTGCTTATCCGCC (SEQ ID NO: 293) | GACCGAGTGCTTATCCGCCTGAGCC (SEQ ID NO: 294)
366 | GACCGAGTGCTTATCCGCCTG (SEQ ID NO: 295) | CCGAGTGCTTATCCGCCTGAGCCGC (SEQ ID NO: 296)
367 | ACCGAGTGCTTATCCGCCTGA (SEQ ID NO: 297) | CGAGTGCTTATCCGCCTGAGCCGCC (SEQ ID NO: 298)
391 | GCCTGCACAACCAGCAGGCAT (SEQ ID NO: 299) | CTGCACAACCAGCAGGCATTGAGCT (SEQ ID NO: 300)
1022 | AGGAGGTGACGGTCCTGAGGA (SEQ ID NO: 301) | GAGGTGACGGTCCTGAGGAGCCTGC (SEQ ID NO: 302)
1043 | GCCTGCTTTGCCCAGCCTGGA (SEQ ID NO: 303) | CTGCTTTGCCCAGCCTGGAGGGCGT (SEQ ID NO: 304)
1056 | AGCCTGGAGGGCGTCAGTGAA (SEQ ID NO: 305) | CCTGGAGGGCGTCAGTGAAAAGCAG (SEQ ID NO: 306)
1057 | GCCTGGAGGGCGTCAGTGAAA (SEQ ID NO: 307) | CTGGAGGGCGTCAGTGAAAAGCAGT (SEQ ID NO: 308)
1075 | AAAAGCAGTACACCATCTACA (SEQ ID NO: 309) | AAGCAGTACACCATCTACATCGCAC (SEQ ID NO: 310)
1079 | GCAGTACACCATCTACATCGC (SEQ ID NO: 311) | AGTACACCATCTACATCGCACCTGG (SEQ ID NO: 312)
1080 | CAGTACACCATCTACATCGCA (SEQ ID NO: 313) | GTACACCATCTACATCGCACCTGGA (SEQ ID NO: 314)
1082 | GTACACCATCTACATCGCACC (SEQ ID NO: 315) | ACACCATCTACATCGCACCTGGAGG (SEQ ID NO: 316)
1085 | CACCATCTACATCGCACCTGG (SEQ ID NO: 317) | CCATCTACATCGCACCTGGAGGCGG (SEQ ID NO: 318)
1086 | ACCATCTACATCGCACCTGGA (SEQ ID NO: 319) | CATCTACATCGCACCTGGAGGCGGG (SEQ ID NO: 320)
1109 | CGGGGCGTTCACGACGTTGAA (SEQ ID NO: 321) | GGGCGTTCACGACGTTGAATGGCTC (SEQ ID NO: 322)
1115 | GTTCACGACGTTGAATGGCTC (SEQ ID NO: 323) | TCACGACGTTGAATGGCTCGCTGAC (SEQ ID NO: 324)
1118 | CACGACGTTGAATGGCTCGCT (SEQ ID NO: 325) | CGACGTTGAATGGCTCGCTGACCCT (SEQ ID NO: 326)

TABLE 2-continued

Candidate cDNA target sequences for silencing RING1.

| Start Position relative to NM_02931.3 | N19 target | N25 extended target |
|---|---|---|
| 1119 | ACGACGTTGAATGGCTCGCTG (SEQ ID NO: 327) | GACGTTGAATGGCTCGCTGACCCTG (SEQ ID NO: 328) |
| 1120 | CGACGTTGAATGGCTCGCTGA (SEQ ID NO: 329) | ACGTTGAATGGCTCGCTGACCCTGG (SEQ ID NO: 330) |
| 1135 | CGCTGACCCTGGAGCTGGTGA (SEQ ID NO: 331) | CTGACCCTGGAGCTGGTGAATGAGA (SEQ ID NO: 332) |
| 1136 | GCTGACCCTGGAGCTGGTGAA (SEQ ID NO: 333) | TGACCCTGGAGCTGGTGAATGAGAA (SEQ ID NO: 334) |
| 1142 | CCTGGAGCTGGTGAATGAGAA (SEQ ID NO: 335) | TGGAGCTGGTGAATGAGAAATTCTG (SEQ ID NO: 336) |
| 1146 | GAGCTGGTGAATGAGAAATTC (SEQ ID NO: 337) | GCTGGTGAATGAGAAATTCTGGAAG (SEQ ID NO: 338) |
| 1148 | GCTGGTGAATGAGAAATTCTG (SEQ ID NO: 339) | TGGTGAATGAGAAATTCTGGAAGGT (SEQ ID NO: 340) |
| 1149 | CTGGTGAATGAGAAATTCTGG (SEQ ID NO: 341) | GGTGAATGAGAAATTCTGGAAGGTG (SEQ ID NO: 342) |
| 1157 | TGAGAAATTCTGGAAGGTGTC (SEQ ID NO: 343) | AGAAATTCTGGAAGGTGTCCCGGCC (SEQ ID NO: 344) |
| 1160 | GAAATTCTGGAAGGTGTCCCG (SEQ ID NO: 345) | AATTCTGGAAGGTGTCCCGGCCACT (SEQ ID NO: 346) |
| 1191 | CTGTGCTATGCTCCCACCAAG (SEQ ID NO: 347) | GTGCTATGCTCCCACCAAGGATCCA (SEQ ID NO: 348) |
| 1199 | TGCTCCCACCAAGGATCCAAA (SEQ ID NO: 1) | CTCCCACCAAGGATCCAAAGTGACC (SEQ ID NO: 2) |

Disease Treatment

The invention provides compositions and methods to silence gene expression related to a disease, or more preferably, to silence gene expression related to the treatment of a disease. Many conditions have genes associated with them (i.e. a gene is the cause or part of the cause of the condition to be treated). In other conditions, the expression of gene influences the response to a therapy, such as chemotherapy. Inhibitory compounds such as the siRNAs taught herein can be used to inhibit the expression of the target gene and therefore alleviate symptoms of a disease or enhance responsiveness to a therapeutic modality. The inhibitory compounds taught herein can be used in conjunction with a topoisomerase inhibitor to treat diseases such as cancers.

The inhibitory compound can be administered before, after, or simultaneously with the topoisomerase inhibitor. Repeated administrations of the inhibitory compound and topoisomerase inhibitor are also contemplated.

Single or multiple administration of the test compound can be given using any convenient mode of administration, including but not limited to intravenous, intraperitoneal, intratumoral, subcutaneous, and intradermal.

The inhibitory compound and topoisomerase inhibitor can be administered at different sites and on different dosage regimens. The enhanced therapeutic effectiveness of the combination therapy of the present invention represents a promising alternative to conventional highly toxic regimens of anticancer agents. Similarly, the enhanced effect of the inhibitory compound with topoisomerase inhibitors, in addition to improving the efficacy of these chemotherapeutic agents, may allow for the administration of lower doses of these chemotherapeutic agents, thus reducing the induction of side effects in a subject, and/or reducing the incidence or delaying or preventing the onset of resistance to the topoisomerase inhibitor.

Dosages and administration protocols for the treatment of cancers using the foregoing methods will vary with the method and the target cancer, and will generally depend on a number of other factors appreciated in the art.

The subject treated by the present methods includes a subject having a tumor susceptible to treatment by a topoisomerase inhibitor. Such tumors can be a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. Tumors treated by compounds of the present methods include, but are not limited to: neoplasm of the central nervous system: glioblastomamultiforme, astrocytoma, oligodendroglial tumors, ependymal and choroids plexus tumors, pineal tumors, neuronal tumors, medulloblastoma, schwannoma, meningioma, meningeal sarcoma: neoplasm of the eye: basal cell carcinoma, squamous cell carcinoma, melanoma, rhabdomyosarcoma, retinoblastoma; neoplasm of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors: neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, vermiform appendix and peritoneum, adenocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, adenocarcinoma of the uterine corpus, ovarian cancer, gynecologic sarcomas; neoplasms of the breast; neoplasms of the skin: basal cell carcinoma, squamous carcinoma, dermatofibrosarcoma, Merkel cell tumor; malignant melanoma; neoplasms of the bone and soft tissue: osteogenic sarcoma, malignant fibrous histiocytoma, chrondrosarcoma, Ewing's sarcoma, primitive neuroectodermal tumor, angiosarcoma; neoplasms of the hematopoietic system: myelodysplastic syndromes, acute myeloid leukemia, chronic myeloid leukemia, acute lymphocytic leukemia, HTLV-1, and T-cell leukemia/lymphoma, chronic lymphocytic leukemia, hairy cell leukemia, Hodgkin's disease, non-Hodgkin's lymphomas, mast cell leukemia; neoplasms of children: acute lymphoblastic leukemia, acute myelocytic leukemias, neuroblastoma, bone tumors, rhabdomyosarcoma, lymphomas, renal and liver tumors.

The formulation and delivery methods will generally be adapted according to the site and the disease to be treated. Exemplary formulations include, but are not limited to, those suitable for parenteral administration, e.g., intravenous, intraarterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. The dosage of the compounds of the invention will vary according to the extent and severity of the need for treatment, the activity of the administered composition, the general health of the subject, and other considerations well known to the skilled artisan.

Pharmaceutical Compositions

The inhibitory compounds as described herein can be incorporated into pharmaceutical compositions suitable for administration. Such compositions typically comprise the agent and a pharmaceutically acceptable carrier. Supplementary active compounds can also be incorporated into the compositions.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as Remington: The Science and Practice of Pharmacy 20th Ed. (Lippincott, Williams & Wilkins 2003).

Pharmaceutically-acceptable materials, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. One formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Treatment of Patients

The gene silencing methods and compositions of the invention can be used to treat patients. In one aspect, a target sequence can be integrated into a patient's genome, and the patient can be treated with target sequence specific siRNAs. Methods (e.g., protocols) and compositions (e.g., formulations) for transfecting cells in vivo are known in the art, as discussed herein.

The above therapeutic approaches can be combined with any one of a wide variety of surgical, chemotherapy or radiation therapy regimens. In one embodiment, the inhibitory compound is combined with a topoisomerase inhibitor, which can optionally include other treatment regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular inhibitory compound or a combination of such compounds can be evaluated using various in vitro and in vivo assay systems, either alone or in combination with a topoisomerase inhibitor, or in the presence of low glucose. In vitro assays that evaluate therapeutic activity include cell growth assays, soft agar assays and other assays indicative of tumor promoting activity, and degradation assays capable of determining the extent to which a inhibitory compound will reduce degradation of a topoisomerase, and binding assays capable of determining the extent to which the compound will stabilize topoisomerase-DNA complexes.

In vivo, the effect of an inhibitory can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating inhibitory compounds. In one embodiment, xenografts from tumor bearing mice treated with the inhibitory compound can be examined for the presence of apoptotic foci and compared to untreated control xenograft-bearing mice. The extent to which apoptotic foci are found in the tumors of the treated mice provides an indication of the therapeutic efficacy of the inhibitory compound(s) in combination with the topoisomerase inhibitor.

Compounds which are determined to be effective for the prevention or treatment of tumors in animals, e.g., dogs, rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals, when adjusted for body surface area.

Screening Using Inhibitory Compounds

The invention also provides screening methods using inhibitory compounds and examining effects on E3 ligase ubiquitination of a substrate, such as, but not limited to, a topoisomerase.

In one embodiment, the method comprises using the test agents in combination with an E3 ubiquitin ligase to identify compounds that modulate ubiquitination of a test substrate. The method can comprise determining the ubiquitination of a E3 ubiquitin ligase substrate in the presence and absence of a test compound; and selecting the test compound as being effective to modulate ubiquitination if the activity of the E3 ubiquitin ligase is altered in the presence of the test compound in comparison to activity in the presence of a control peptide. The determining step can involve measuring the amount of ubiquitination and/or rate of ubiquitination. Ubiquitination can be determined using any of a number of known methods, including using a fluorescence (such as, but not limited to using FRET). The selecting step can involve selecting the test compound as being effective if ubiquitination of the substrate is decreased in the presence of the test compound. The methods can occur within a cell, or in a cell-free environment. In certain embodiments, the test compound is a dsRNA.

The invention further contemplates a process for making a compound that modulates the ubiquitination of a substrate by an E3 ubiquitin ligase, comprising: carrying out a method as described herein to identify a compound that modulates the ubiquitination of a E3 ubiquitin ligase substrate; and manufacturing the compound.

Kits

The invention provides kits comprising compositions and methods of the invention, including cells, inhibitory compounds, target sequences, transfecting agents, transducing agents, instructions (regarding the methods of the invention), therapeutic agents such as but not limited to topoisomerase inhibitors, or any combination thereof.

Typically such kits can comprise a carrier, package or container that is compartmentalized to receive one or more containers such as vials, tubes, and the like, each of the container(s) comprising one of the separate elements to be used in the method. For example, the container(s) can comprise an inhibitory compound that is or can be detectably labeled. Such inhibitory compound can be an antibody or polynucleotide specific for an E3 ubiquitin ligase protein or an E3 ubiquitin ligase gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

In one embodiment, the kit comprises one or more siRNAs that target an E3 ubiquitin ligase. In one aspect, the E3 ubiquitin ligase is Bmi1 and/or RING1.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

The invention will be further described with reference to the following examples; however, it is to be understood that the invention is not limited to such examples.

Throughout this application, various publications are referenced. All patents, patent applications, published applications and publications, Genbank sequences, websites and other published materials referred to throughout the entire disclosure, as well as references cited within those publications, herein are incorporated by reference in their entirety. The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Silencing of a E3 Ubiquitin Ligase Increases Drug Toxicity

RNAi oligomers were designed that specifically targeted 77 candidate genes. Two RNAi oligomers per gene were tested through a toxicity assay in HeLa cells under the assumption that silencing of a critical E3 ubiquitin ligase would increase drug toxicity. The oligomers were obtained from IDT DNA (IL USA). The screen was carried out in the presence of sub-toxic concentrations of CPT (Camptothecin, Sigma, Israel), a TOPI drug, and VM26 (Teniposide, Alexis Biochemicals Corp., CA, U.S.A.), a TOPII drug. HeLa cells were transfected with the RNAi oligomers using the SaintRed reagent (Synvolux Therapeutics, B.V., NL) according to the manufacturer's instructions. 32 hours after transfection, the cells were treated with sub-toxic concentrations of about 0.1 µM CPT or about 1 µm VM26 for an additional 16 hours, after which time the media was changed. The viability of the cells was determined 24 hours later using AlamarBlue reagent (Roche, Germany). Twenty-four candidates RNAi oligomers were identified in the initial toxicity screen using a 20% increase in toxicity as the bench-mark for efficacy (data not shown).

The effects of the candidate RNAi oligomers on drug-induced TOPI or TOPII (α and β) degradation were examined. One candidate, Bmi1, was successfully inhibited as measured by both the toxicity and the degradation assays.

Bmi1 was successfully suppressed by two different RNAi oligomers, named X63 and X165, which sequences are shown below:

|     | Sense | Anti-sense |
| --- | --- | --- |
| X63 | 5'-AUGGGUCAUCAGCAACUUCUUCUdGdG (SEQ ID NO: 3) ("d" stands for deoxynucleotide.) | 5'-CCAGAAGAAGUUGCUGAUGACCCAUUU (SEQ ID NO: 4) |
| X165 | 5'-AACUCUCCAAGAUAUUGUAUACAdAdA (SEQ ID NO: 5) ("d" stands for deoxynucleotide.) | 5'-UUUGUAUACAAUAUCUUGGAGAGUUUU (SEQ ID NO: 6) |

In a follow-up experiment, HeLa cells were transfected with 100 nM of X63 or X165 using SaintRed according to the manufacturer's instructions. Twenty-four hours post-transfection, the cells were treated for 16 hours with DMSO, 0.1 µM CPT or 1 µM VM26, after which time the media was changed. After another twenty-four hours, the viability of the cells was determined visually using AlamarBlue reagent (Roche, Germany) (FIG. 1A), and cell number was quantified (FIG. 1B). Administration of either X63 or X165 increased VM26 and CPT-induced toxicity in HeLa cells (FIGS. 1A and 1B).

Figure 2:
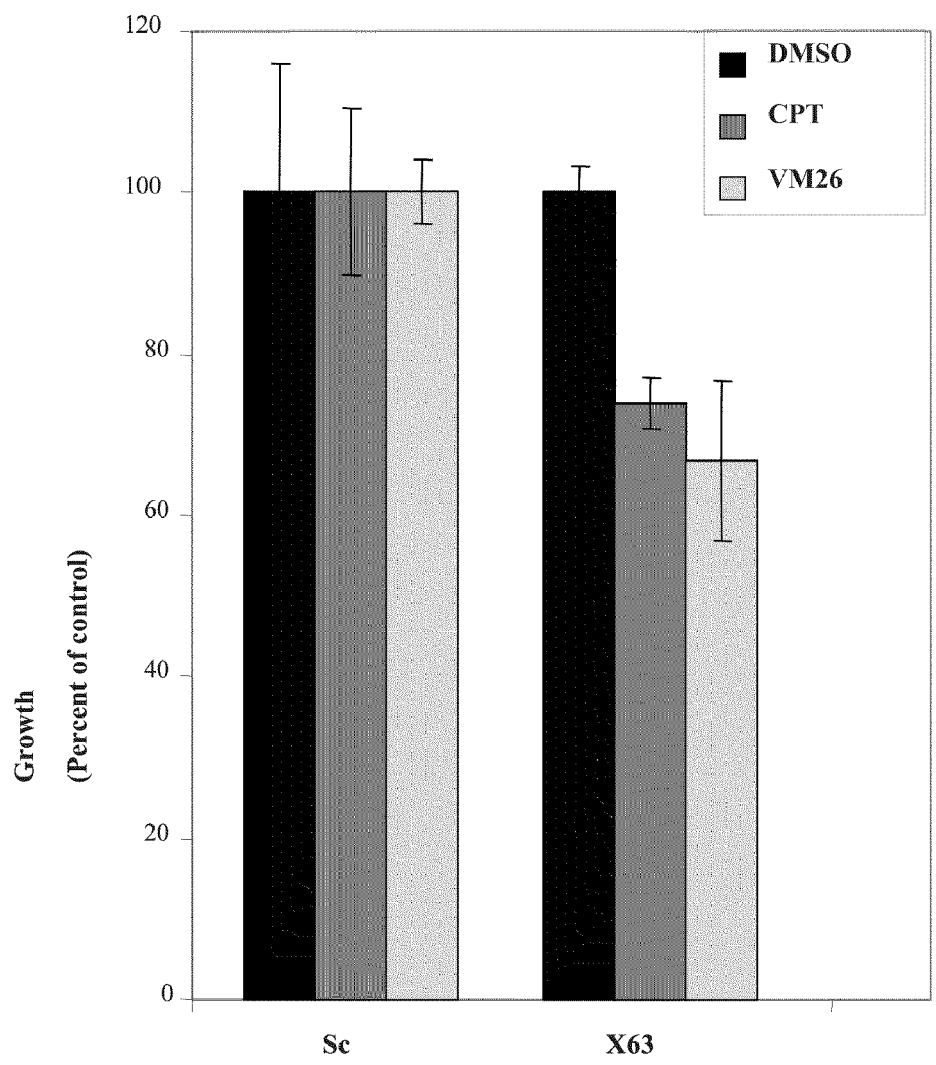
FIG. 2 shows HT29 cells transfected with a scrambled RNAi control (Sc) or the X63 RNAi targeting Bmi1. Silencing of Bmi1 increased the toxic effects of CPT and VM26 in HT29 cells.

Similar results were obtained in HT29 colon cancer cell line (FIG. 2), which were grown in McCoy's 5A medium with 10% FCS and were treated with the same concentrations of siRNA, CPT and VM26, indicating that silencing of Bmi1 increased the toxic effect of VM26 and CPT in more than one cell line.

Example 2 siRNA Silencing of Bmi1 Stabilized TOPI and TOPIIα Degradation

HeLa cells were transfected with the Bmi1 X63 and X165 RNAi oligomers, or a scrambled RNAi oligomer using the conditions described in Example 1. Forty-eight hours post-transfection, the cells were treated for 0, 3, or 5 hours with 100 µM VM26, or for 0, 4.5 or 6 hours in the presence of 25 µM CPT. Certain of the scrambled oligomer-treated cells were treated with 25 µM of the proteasome inhibitor, MG132 (Sigma, Israel). The cells were harvested, alkaline extracted and treated with S7 DNAse (Roche, Germany) to release TOPII from the DNA.

Figure 3:
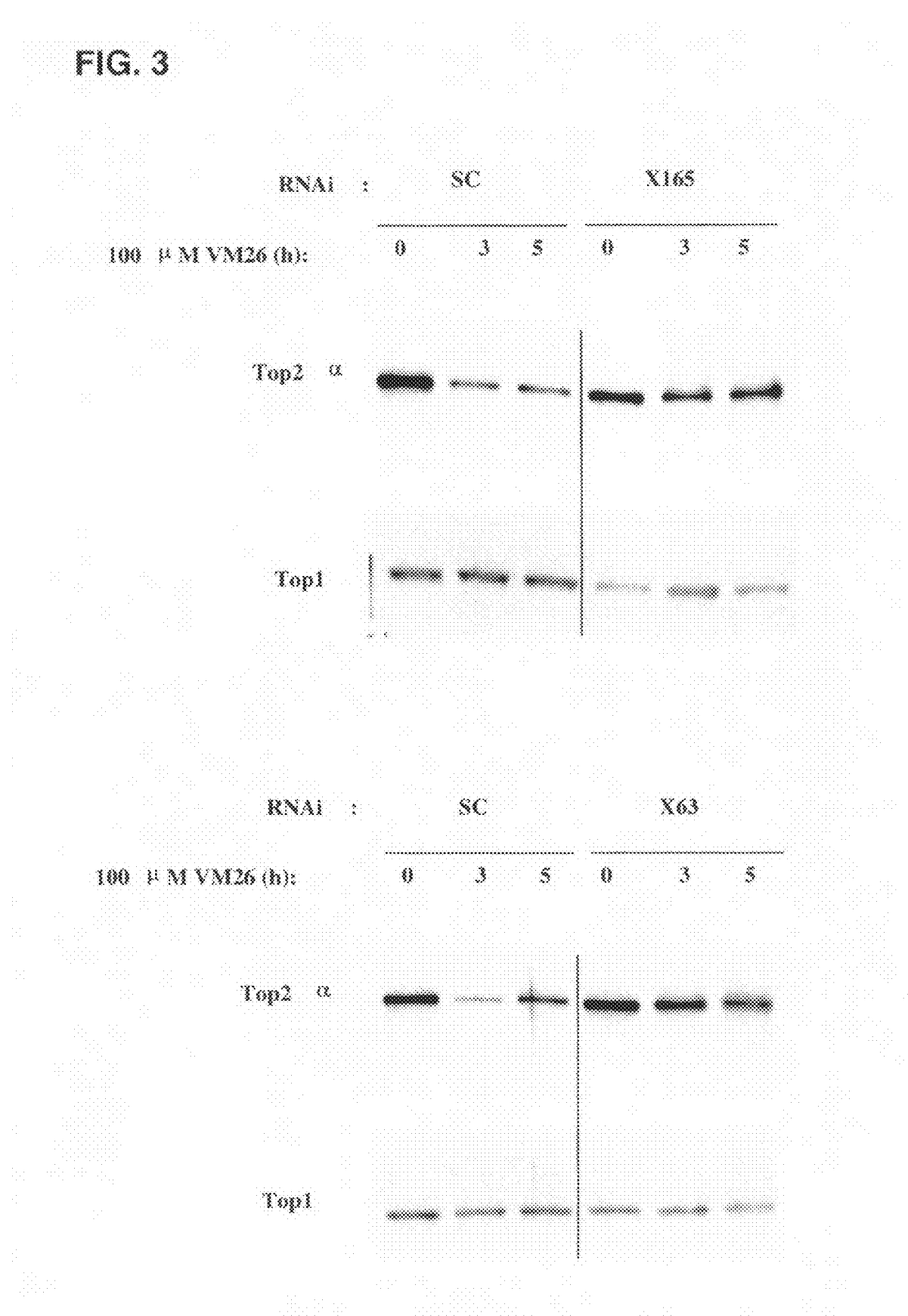
FIG. 3 shows immunoblots of TOPI and TOPIIα levels in HeLa cells transfected with a scrambled RNAI control (Sc) or the X63 and X165 RNAi oligomers targeting Bmi1 and treated with VM26.
Figure 4:
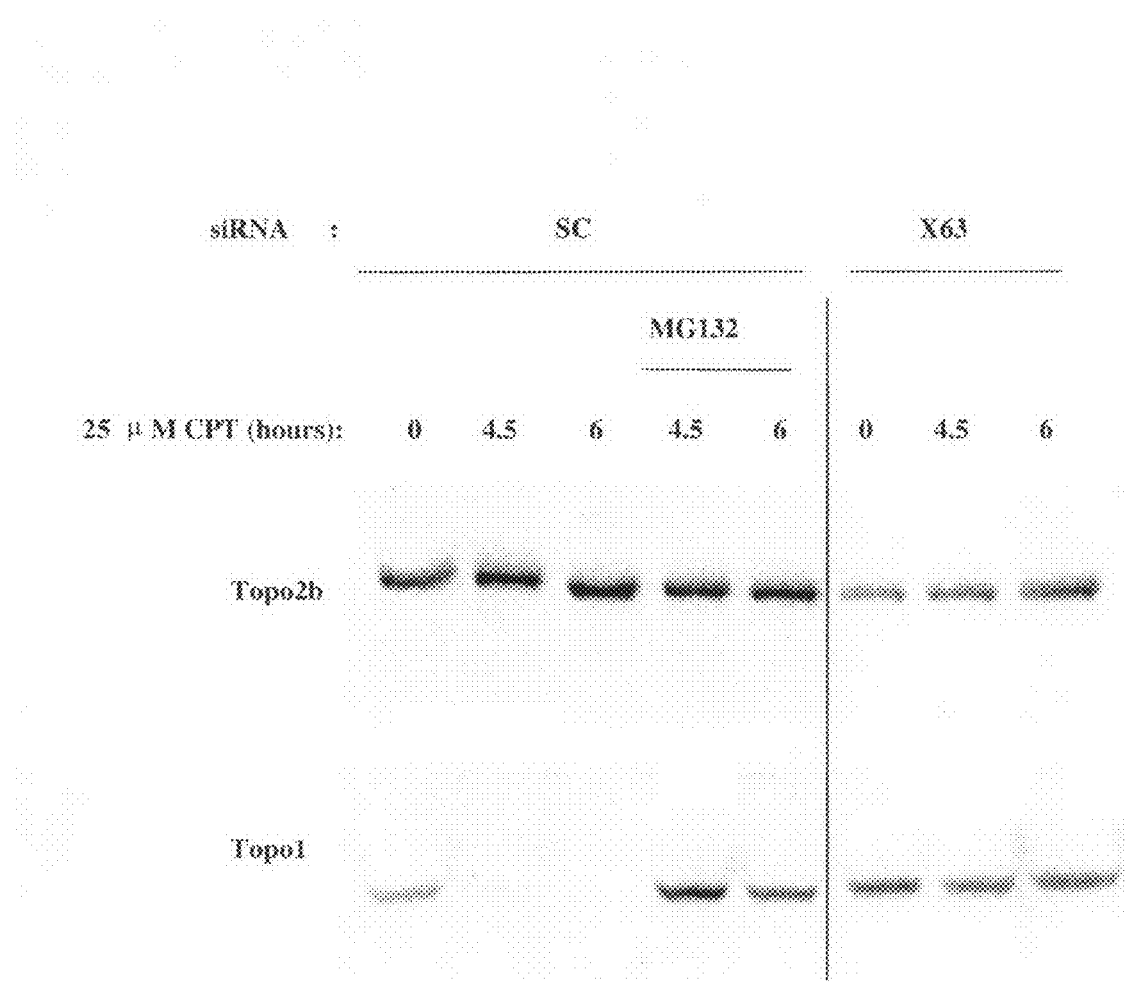
FIG. 4 shows immunoblots of TOPI and TOPIIβ levels in HeLa cells transfected with a scrambled RNAI control (Sc), with or without MG132, or the X63 RNAi oligomers targeting Bmi1 and treated with CPT.

The amounts of TOPIIα, TOPIIβ and TOPI were then assayed by immunoblot with specific anti-TOPII and anti-TOPI antibodies (Santa Cruz Biotechnology, Inc., CA. U.S.A.) (FIGS. 3 and 4). The general protocol for Western analysis was as described previously. Briefly, nitrocellulose membranes were blocked for 0.5-1 hour with 5% non-fat milk in TBS-T (TBS supplemented with 0.5% [v/v] Tween 20), incubated with the primary antibody for 1 hour, washed four times with TBS-T for 5 minutes each, and then incubated for 60 minutes with secondary antibodies conjugated to horse-radish peroxidase (Amersham Bioscience UK). Membranes were then washed as described above. Visualization of antigen and antibody complexes was achieved using chemiluminescent reagents (SuperSignal West Pico Chemiluminescent, PIERCE, Ill., U.S.A.) as substrates for the HRP.

In cells where Bmi1 was suppressed, there was a correlation between increased susceptibility to drug-induced toxicity and TOPI/TOPIIα stabilization. Silencing of Bmi1 by RNAi oligomers stabilized the VM26-induced TOPIIα degradation (FIG. 3) and CPT-induced TOPI degradation (FIG. 4), as did treatment with MG132 (FIG. 4).

Example 3 siRNA Silencing of Bmi1 Stabilized TOPIIα-DNA Degradation

HeLa cells were transfected with control (scrambled) or X63 Bmi1 RNAi oligomers as described in Example 1. Twenty-four hours after transfection, the cells were treated for various times with DMSO, 100 µM VM26 and 25 µM MG132 as indicated in FIG. 5.

The cells were harvested, and genomic DNA was isolated and separated on a cesium-chloride column as previously described (Desai, S. D., et al., Cancer Res., 2001. 61(15): p. 5926-32). Briefly, cells were lysed in Sarkosyl lysis buffer containing 1% sarkosyl in 10 mM Tris-HCl (pH 7.5) and 1 mM EDTA. The cells were then passed through an 18-gauge needle 5 times, and the resultant cell extract was laid on top of a 1.5 g/ml cesium-chloride density centrifugation column and centrifuged for ~5 hours at ~438,000 g. This step was designed to resolve the DNA from any free proteins, such that the covalent complexes containing topoisomerase and genomic DNA pelleted in the column along with the genomic DNA, while free topoisomerase remained at the top of the column. The pelleted DNA was recovered and the amount of TOPIIα covalently bound to equal amount of DNA was determined by the dot-blot method, generally as described in Example 2.

Figure 5:
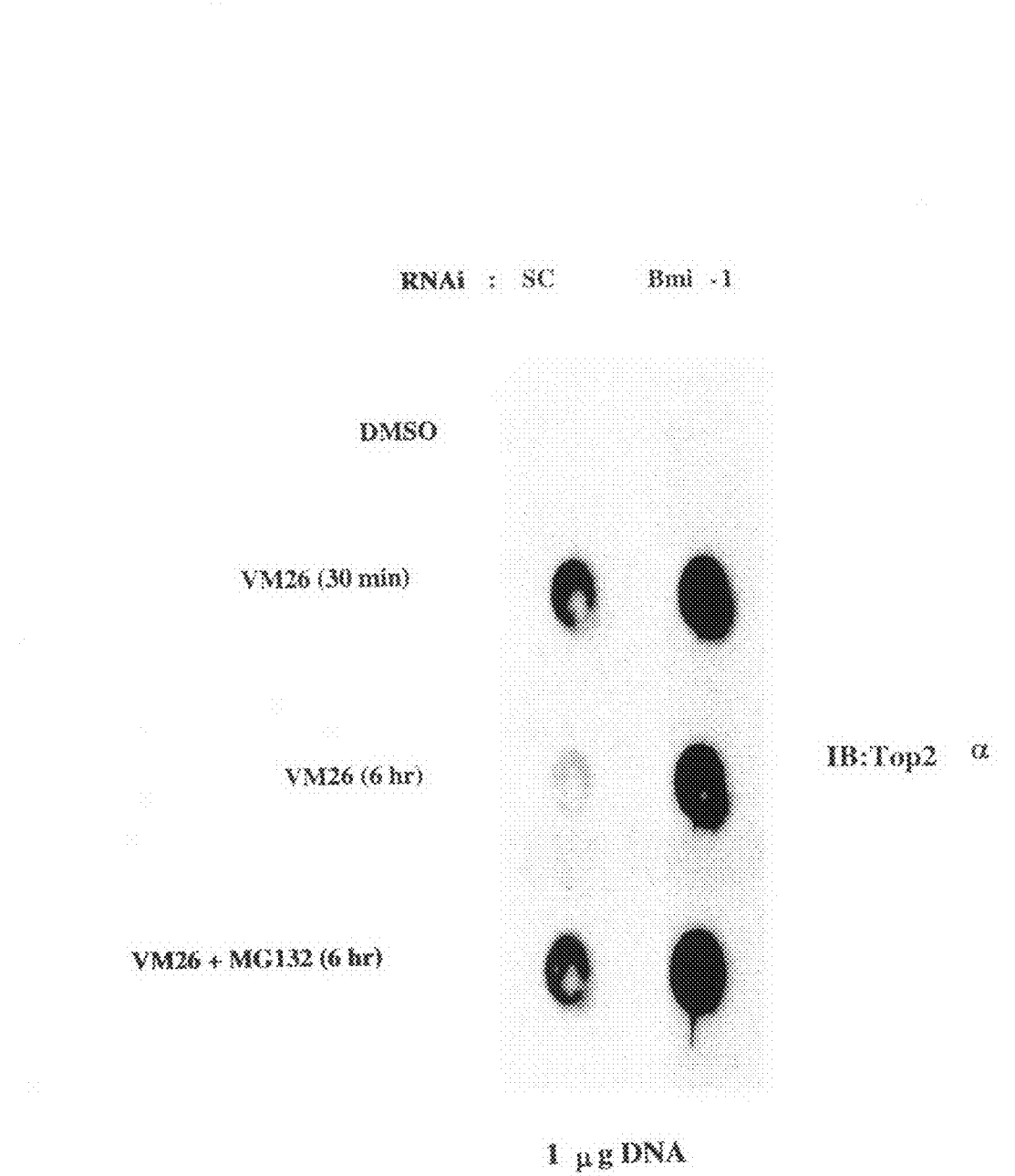
FIG. 5 shows a dot blot of TOPIIα levels in HeLa cells transfected with a scrambled RNAi control (Sc) or the X63 RNAi oligomer targeting Bmi1 and treated with VM26, with or without MG132, for varying lengths of times.

After 30 minutes of VM26 treatment, TOPIIα was found complexed with DNA in both control and Bmi1 RNAi oligomer treated cells (FIG. 5). In control RNAi treated cells, TOPIIα was degraded after 6 hours of VM26 treatment; treatment with the proteasome inhibitor MG132 prevented this degradation (FIG. 5). In contrast, the X63 Bmi1 RNAi stabilized the TOPIIα-DNA complex after 6 hours of drug treatment (FIG. 5).

Example 4 siRNA Silencing of Bmi1 Stabilized TOPI and TOPIIα Degradation in Low Glucose Conditions HeLa and HT29 cell lines were treated with control and X63 Bmi1 RNAi oligomers essentially as described in Example 1. Four hours after transfection, the tissue culture medium was replaced with fresh medium containing either normal or low levels of (or essentially no) glucose for an additional 44 hours of culture.

The cells were harvested and the cell extracts analyzed by immunoblot essentially as described in Example 2.

Figure 6:
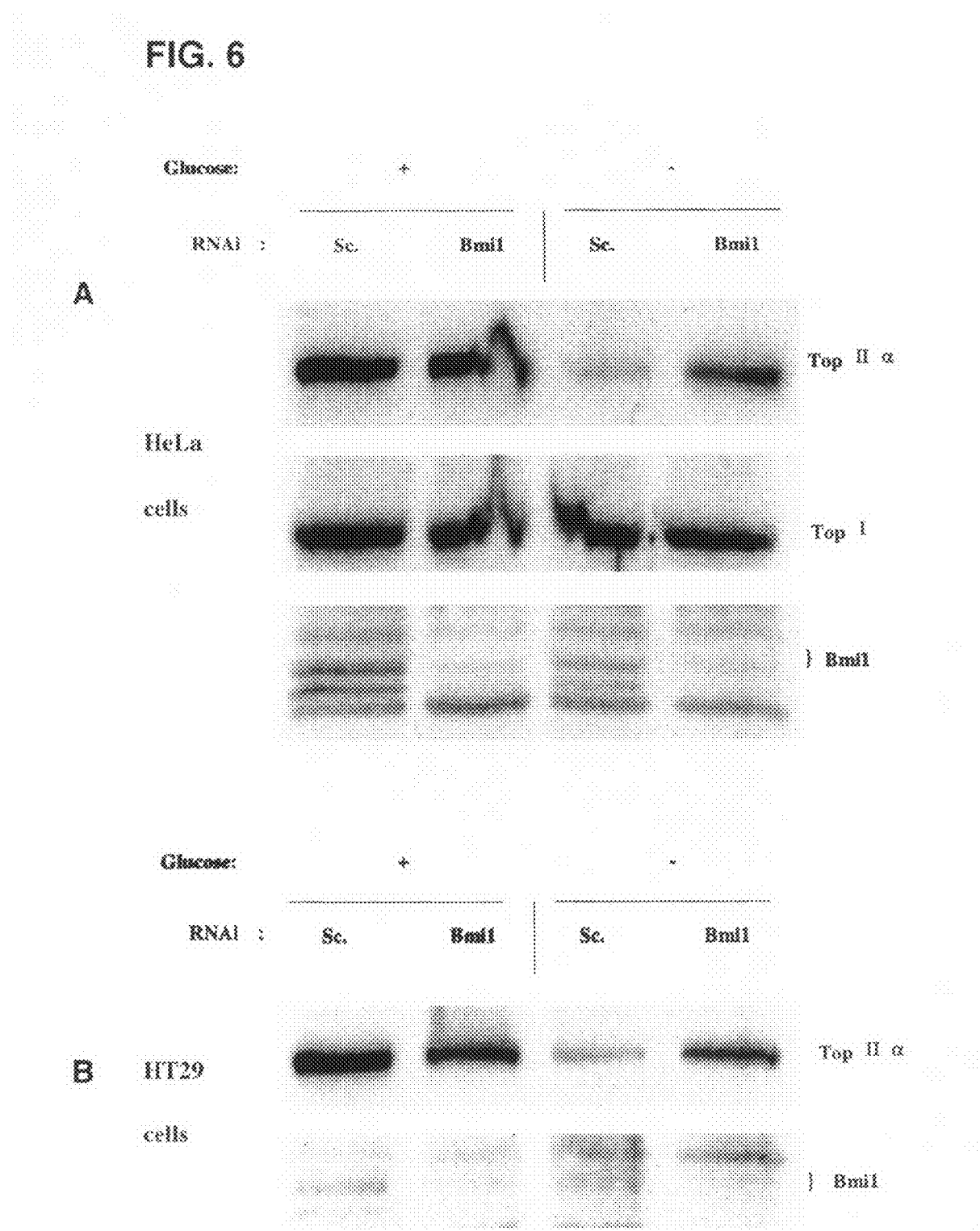
FIGS. 6A and B show immunoblots of TOPI, TOPIIα, and Bmi1 levels in HeLa cells (A) and HT29 cells (B) transfected with a scrambled RNAI control (Sc) or the X63 RNAi oligomer targeting Bmi1 and treated in low glucose conditions.

The level of TOPIIα was reduced in cells that were cultured in low-glucose medium, while treatment with the Bmi1 X63 RNAi oligomer prevented the reduction (FIGS. 6A and B).

Similar results were obtained in both HeLa and HT29 cell lines (FIGS. 6A and B, respectively). TOPI levels were not affected by the low-glucose condition in the HeLa cell line (FIG. 6A).

Example 5 siRNA Silencing of RING1 Stabilized TOPIIα Degradation

RING1 was identified as a candidate in Example 1. Silencing of RING1 but not RING1B inhibited the drug-induced degradation of TOPIIα.

HeLa cells were transfected with a scrambled oligomer, the Bmi1 X63 oligomer, a RING1 X154 oligomer, a RING1 X155 oligomer, or a RING1B X96 oligomer essentially as described in Example 1.

The sequences of the oligomers are as follows:

| | Sense | Anti-sense |
|---|---|---|
| X154 | 5'-CUGCAUUGUCACAGCCCUACGG AdGdC (SEQ ID NO: 7) | 5'-GCUCCGUAGGGCUGUGACAAUG CAGUU (SEQ ID NO: 8) |
| X155 | 5'-AGAUCUAUCCUAGCCGGGAGGA AdTdA (SEQ ID NO: 9) | 5'-UAUUCCUCCCGGCUAGGAUAGA UCUUU (SEQ ID NO: 10) |
| X96 | 5'-GCACAAAUGAGCCUUUAAAAAC CdAdA (SEQ ID NO: 11) | 5'-UUGGUUUUUAAAGGCUCAUUUG UGCUU (SEQ ID NO: 12) |

Forty-eight hours post-transfection the cells were treated for the indicated times with 100 µM of VM26. The cells were harvested, alkaline extracted and treated with S7 DNAse to release TOPIIα from the DNA. The amount of TOPIIα and TOPI was assayed by immunoblot essentially as described in Example 2. Levels of RING1 and RING1B were also analyzed by Western blot. Cell survival in the different conditions was quantified.

Figure 7:
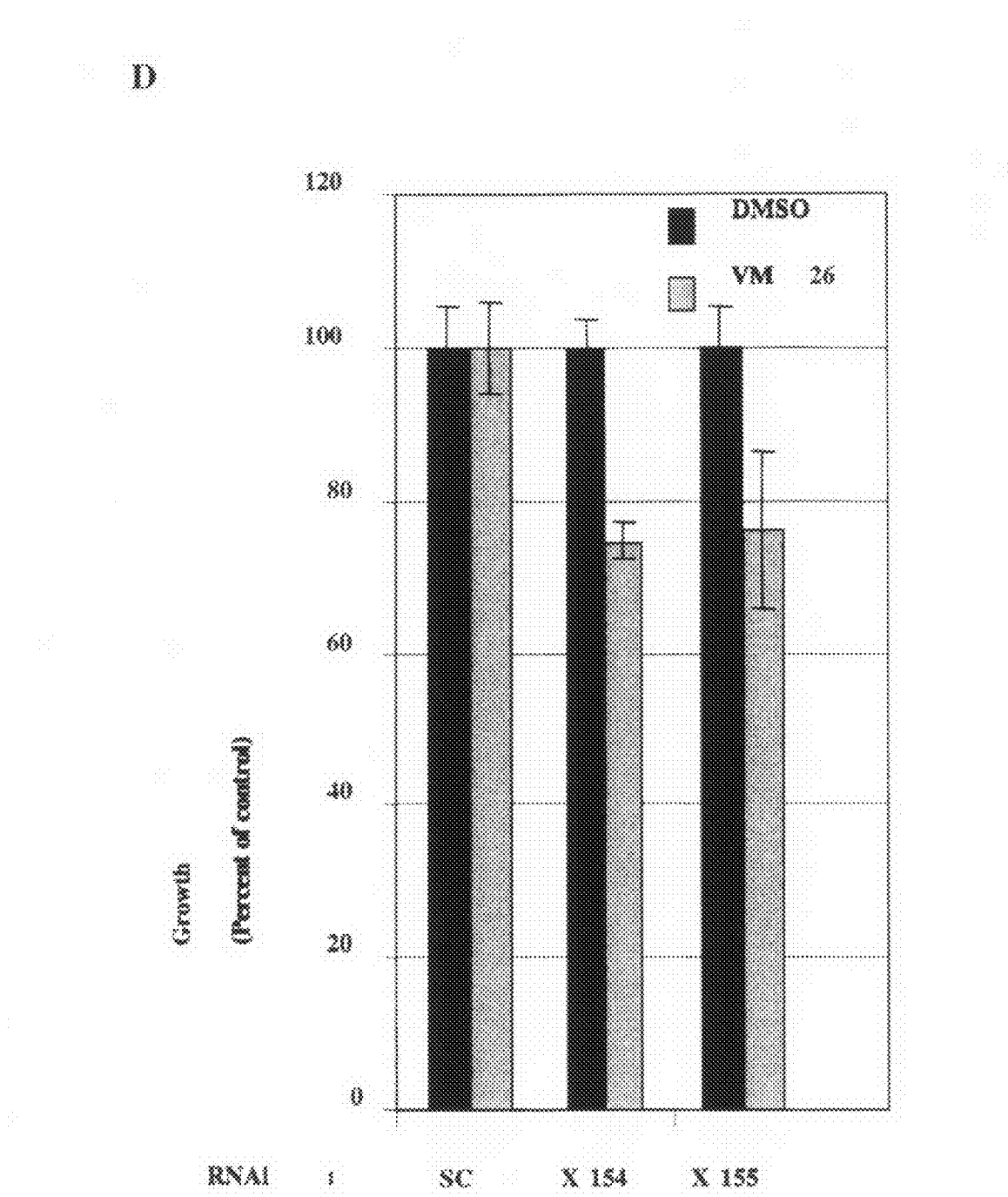
FIGS. 7A, B, and C show immunoblots of TOPI, TOPIIα (A), RING1 (B) and RING1B (C) levels in HeLa cells transfected with a scrambled RNAi control (Sc), the X63 RNAi oligomer targeting Bmi1, the X154 RNAi oligomer targeting RING1, or the X96 oligomer targeting RING1B and treated with VM26.
FIG. 7D charts and compares cell growth in the different conditions. Cells were transfected in triplicate.

Levels of TOPI remained consistent between the various treatments, while levels of TOPIIα decreased in the scrambled and X96 treatments, and remained relatively constant in the X63 and X154 treated cells (FIG. 7A). Silencing of RING1 and RING1B by the RNAi was verified by western blot analysis (FIGS. 7B and 7C respectively). It is notable that RING1B (and not RING1) is the catalytic subunit of PRC1 in the ubiquitination of H2A (Xiao, H., et al., Proc. Natl. Acad. Sci. U.S.A., 2003. 100(6): p. 3239-44. Epub 2003 March 10).

As expected, the silencing of RING1 by the 2 different RNAi oligomers X154 and X155 increased VM26-induced toxicity in HeLa cells (FIG. 7D).

Example 6 siRNA Silencing of Bmi1 and Topoisomerase Treatment Act Synergistically to Reduce Viability of Various Cancer Cells A549 and HeLa cells were cultured with DMEM and 10% FBS. DU145 cells were cultured with MEM-Eagle and 10% FBS. MDA-MB-231 cells were cultured with RPMI and 10% FBS.

Figure 8:
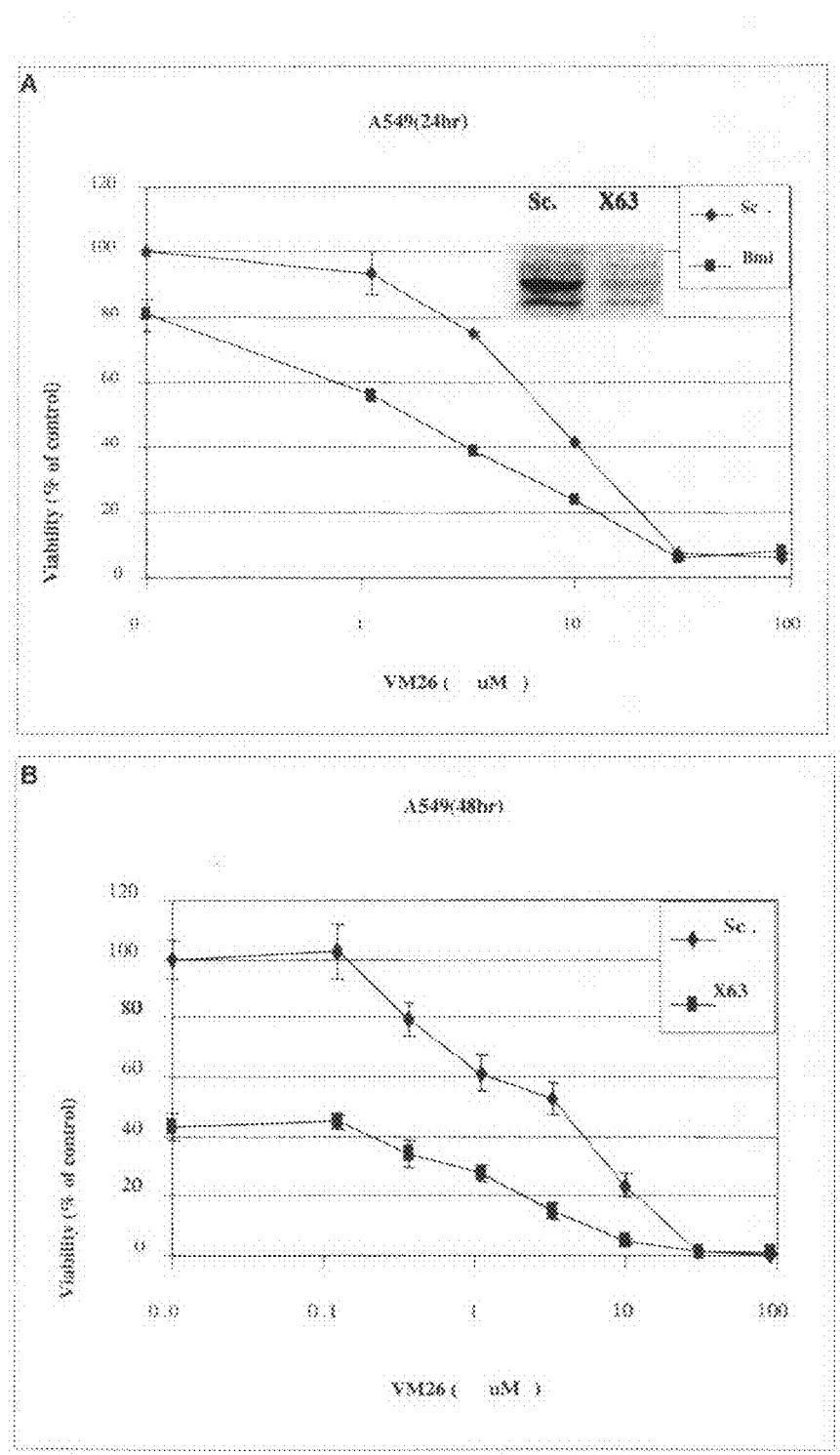
FIG. 8 show the viability of A549 (A and B), HeLA(C), DU145(D) and MDA-MB-231cells(E) transfected with a scrambled RNAi control (Sc) or the X63 RNAi oligomer targeting Bmi1, and treated with DMSO or varying concentrations of VM26. Cells were transfected in triplicate.
Figure 8:
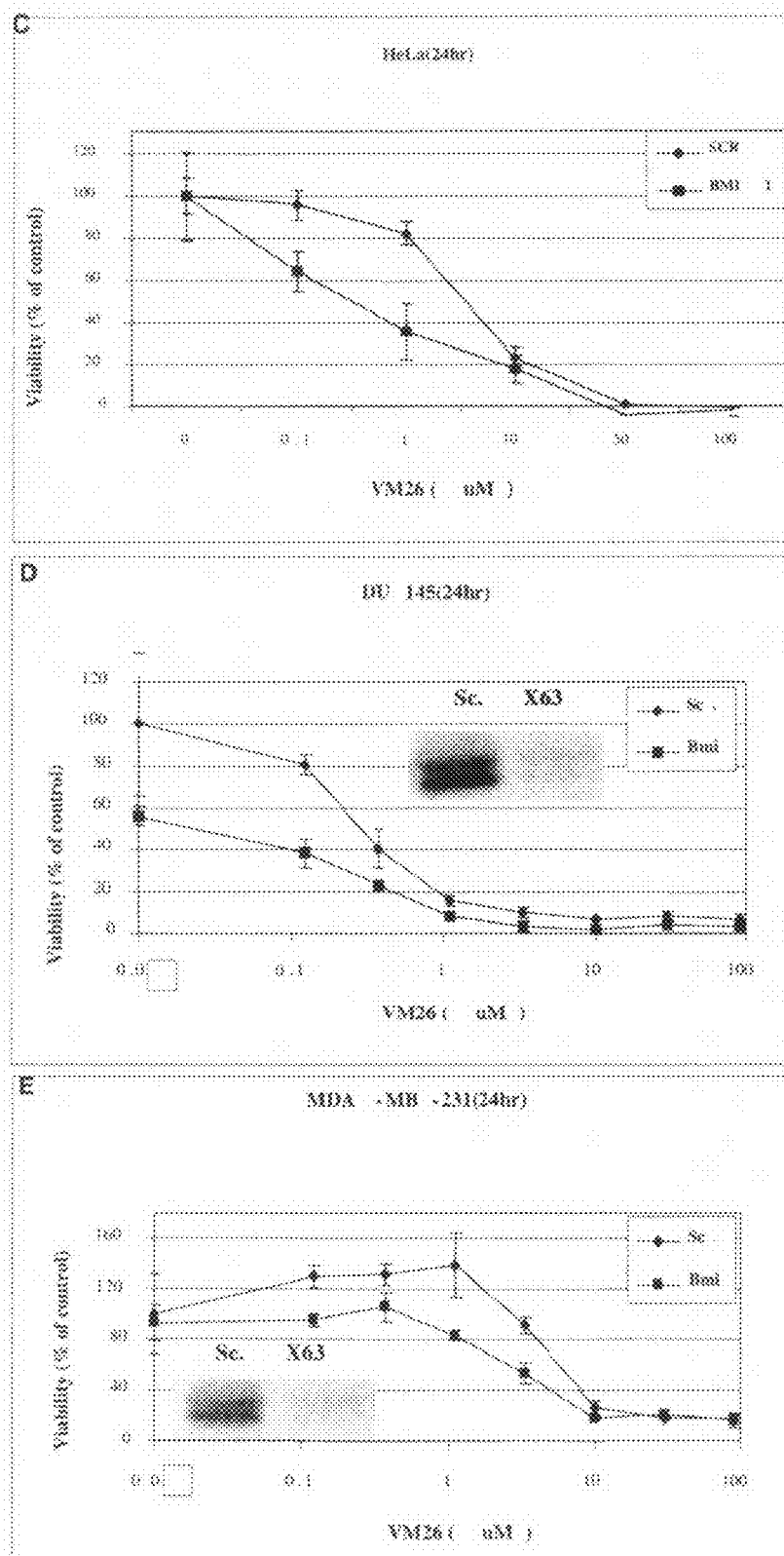

The cells were transfected with RNAi targeting Bmi1 (X63) or control RNAi (Sc) as described in example 1. Twenty-four hours post-transfection, the cells were treated for 16 hours with DMSO (control), or with varying concentration of the TOPII drug, VM26. The viability of the cells was determined after an additional twenty-four hours (FIG. 8A (A549), C (HeLa), D (DU145) and E (MDA-MB-231)) or forty-eight hours (FIG. 8B (A549)) of culture using WST-1 (Roche, Germany) according to the manufacturer's instructions. The experiment was performed in triplicate.

A reduction in Bmi1 protein level was verified by immunoblot assay with Bmi1 specific antibodies, demonstrating that Bmi1 expression was suppressed (see inset panel A, D and E).

Not only were Bmi1 protein levels decreased in the different types of cancer cells, but the siRNA treatment synergistically induced cell death when administered with VM26. Moreover, over time, siRNA treatment induced cell death in the absence of topoisomerase treatment (compare 0 µM VM26 in FIGS. 8A and B).

Example 7

Identification of Modulators of RING1/Bmi1 Ubiquitination Activity

An assay is provided that measures the ubiquitination activity of the E3 ligase RING1 as a complex with Bmi1. A commercially available ubiquitin-derivative can be employed as a fluorescence donor molecule, while a fluorophore-linked antibody is used as a fluorophore acceptor. Ubiquitination of a substrate protein was detected by the emission of the acceptor antibody (specifically bound to a substrate protein, via an antigen-antibody interaction) that was excited by the photon emitted from the donor (ubiquitin-linked) fluorophore, following donor excitation. Since ubiquitin-ligation brings both fluorophores within sufficient proximity for efficient energy-transfer, this reaction can be performed in homogeneous reaction conditions. The Europium Cryptate donor fluorophore fluoresces over a much greater time-period than most common fluorophores, thus enabling the reaction to be detected in a time-resolved format that eliminates interference from auto-fluorescing molecules that may be found in the environment.

Alternatively, the poly-ubiquitin chain can be used as the means to induce proximity between the fluorophores. For this detection method, Biotin-Ubiquitin is added to the reaction and a Streptavidin-fluorophore acceptor molecule is substituted for the antibody described earlier.

The following reagents can be used in the assay:
1. E1 Ubiquitin Activating Enzyme (0.6 mg/ml, 6 µM, Proteologics, Israel)
2. UBCH5a—(Cat# E2616 (50 µM), Boston Biochem Inc., MA, U.S.A.)
3. Recombinant RING1/Bmi1 protein complex (GST, or other unique epitope-tag, Proteologics, Israel)
4. Ubiquitin 1 mg/ml solution in HPLC water
5. Ubiquitin-Cryptate—(cat# 61UBIKLB, CisBio, Mass., U.S.A.)
6. (Optional) Biotin-Ubiquitin (or similar tag), if chain-elongation is to be detected.
7. Anti-GST-XL665—(cat# 61GSTXLB, CisBio, Mass., U.S.A., or similar reagent corresponding to epitope tag in RING1/Bmi1)
8. (Optional) Streptavidin-XL665—(cat# 61SAXLB, CisBio, Mass., U.S.A.—(or corresponding reagent), if chain-elongation is to be detected.)
9. Ovalbumin 100 mg/ml solution in HPLC water
10. ATP—0.1M
11. MgCl$_2$—1M, Sigma
12. EDTA—0.5M, pH=8.
13. Tris 1M pH=7.6—Sigma Biotechnology Grade
14. Tween 20-6% solution in HPLC water 15. KF Buffer (0.8 M KF; 2 mg/ml BSA; and 200 mM phosphate buffer, pH=7.0)
16. DTT—0.1M solution in HPLC water The following solutions are prepared: Dilution Buffer (25 mM Tris, pH=7.6; 0.006% Tween 20; 0.1 mM DTT; and 0.5 mg/ml Ovalbumin); 3× Reaction Mix (15 nM E1 ubiquitin ligase activating enzyme (Proteologics, Israel); 6 mM ATP, 15 mM $MgCl_2$; 105 nM Ubiquitin-Cryptate; 840 mM Ubiquitin (or alternatively, a mix of Ubiquitin/Biotin-Ubiquitin is used if chain-elongation is to be detected); and 300 nM UBCH5a); 2×RING1/Bmi1 Solution (0-100 nM of RING1/Bmi1 in cold dilution buffer); Test Compound Solution (the test compound is diluted in 6% DMSO and 6% PEG-400, typically to 10-50 µM); Antibody Solution (the antibody (such as the anti-GST-XL665 antibody, (CysBio, France)) is diluted 1:50 in KF buffer). The reaction mix is prepared in cold dilution buffer and kept on ice. The test compound solution is kept at room temperature.

The reactions are performed in Costar PS black 96 well plates, and detected using a BMG RubyStar plate-reader (or equivalent).

Briefly, 5 µl of Test Compound solution is added to each well. 15 µl of 2×RING1/Bmi1 solution or Dilution Buffer (negative control) is also added to each well. The solutions are mixed by shaking, and are incubated at room temperature for 10 minutes. 10 µl of 3× Reaction Mix is added to each well, mixed by shaking and incubated at 37° C. for 1 hour. The reaction is stopped by adding 10 µl 0.5 M EDTA to each well. 30 µl of antibody solution is added to each well, mixed by shaking, and incubated for 2 hours at room temperature.

Reactions are read in the RubyStar plate-reader. The reaction mixtures are excited at 310 nm, and emissions are collected at 620 and 665 nm, with 50 µsec delay. Activity is measured by the ratio of emission of acceptor (665 nm) to emission of donor (620 nm)×10,000.

Figure 9:
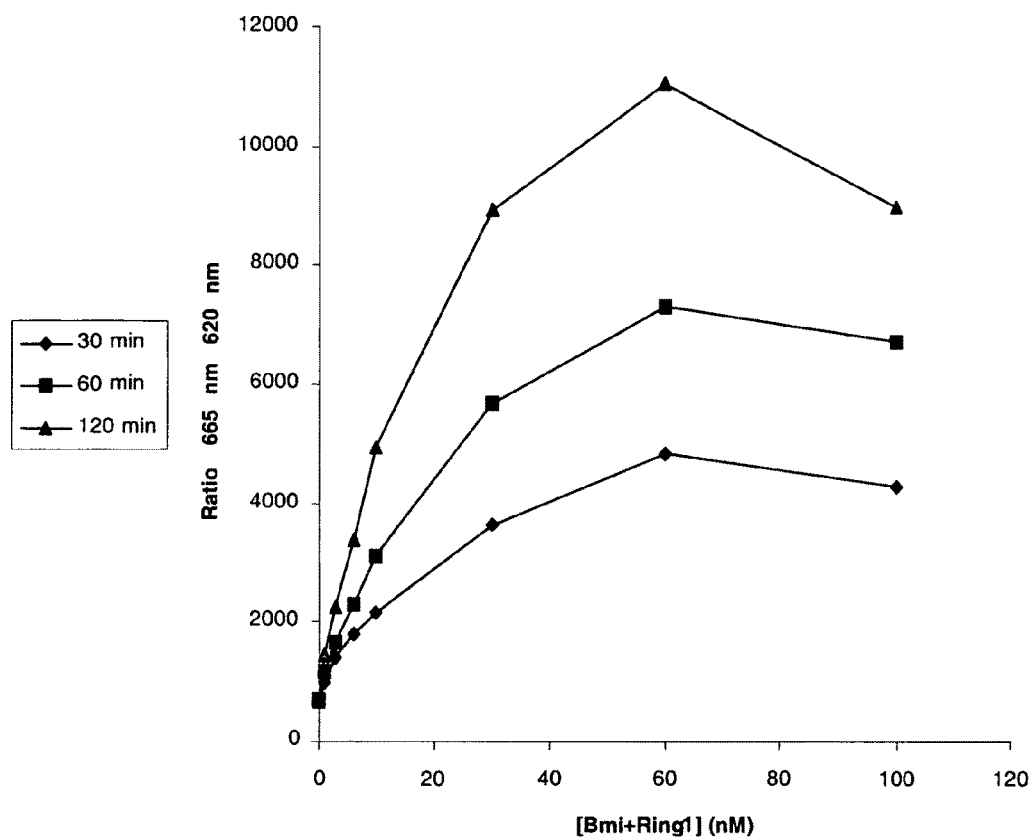
FIG. 9 shows an example of self-ubiquitination of RING1/Bmi1 using a fluorescence based assay.

Different concentrations of RING1/Bmi1 were used, and the reactions were performed as described in the above-described method. Incubation times were at 37° C. for 30, 60, and 120 minutes. The results of the assay are shown in FIG. 9, demonstrating that this assay is useful for determining whether a test compound modulates the ubiquitination activity of RING1 in a complex with Bmi1 by examining the self-ubiquitination of the RING1/Bmi1 complex. Test compounds from chemical libraries are added to the assay in varying concentrations during the screen.

An alternative set of reagents can be used for Ring1/Bmi1 ubiquitination assay:
1. E1 Ubiquitin Activating Enzyme (0.6 mg/ml, 6 µM, Proteologics, Israel
2. UBCH5a (cat #UW9050-0100, Biomol, Pa., U.S.A)
3. Recombinant RING1/Bmi1 protein complex (GST, or other unique epitope-tag, Proteologics, Israel)
4. Anti-FLAG-Cryptate (cat# 61FG2KLB, CisBio, Mass., U.S.A.)
5. Anti-FLAG-XL665—(cat #61FG2XLB, CisBio, Mass., U.S.A.)
6. Ovalbumin 100 mg/ml solution in HPLC water
7. ATP—0.1M
8. $MgCl_2$—1M, Sigma
9. EDTA—0.5M, pH=8.
10. Tris 1M pH=7.6—Sigma Biotechnology Grade
11. Tween 20-6% solution in HPLC water
12. KF Buffer (1.6M Potassium Fluoride in HPLC water)
13. DTT—0.1M solution in HPLC water The following solutions are prepared: Dilution Buffer (25 mM Tris, pH=7.6; 0.006% Tween 20; 0.1 mM DTT; and 0.5 mg/ml Ovalbumin); 4× Reaction Mix (8 mM ATP, 20 mM $MgCl_2$; 1000 nM FLAG-Ubiquitin (Boston Biochem Inc., MA, U.S.A.); 400 nM UBC5A); 4× E1 Solution (20 nM E1 in cold dilution buffer); 4×RING1A/GST-BMI1 Solution (80 nM RING1A\BMI1 in cold dilution buffer, and keep on ice); Test Compound Solution (the test compound is diluted in 4% DMSO and 4% PEG-400, at room temperature); Antibody Solution (1.4% (v/v) Anti-FLAG-XL665, 1% (v/v) Anti-FLAG-Europium Cryptate; 50% (v/v) 1.6M KF; 47.6% (v/v) Dilution buffer). The reaction mix is prepared in cold dilution buffer and kept on ice. The test compound solution is kept at room temperature.

The reactions are performed in Costar PS black 96 well plates, and detected using a BMG RubyStar plate-reader (or equivalent).

Briefly, 11 µl of Test Compound solution is added to each well. 11 µl of 4×RING1/Bmi1 solution or Dilution Buffer (negative control) is also added to each well. The solutions are mixed by shaking, and are incubated at room temperature for 10 minutes. 11 µl of 4× Reaction Mix is added to each well, mixed by shaking and incubated at 37° C. for 1 hour. The reaction is stopped by adding 11 µl 0.5 M EDTA to each well. 22 µl of antibody solution is added to each well, mixed by shaking, and incubated for 2 hours at room temperature.

Reactions are read in the RubyStar plate-reader. The reaction mixtures are excited at 310 nm, and emissions are collected at 620 and 665 nm, with 50 µsec delay. Activity is measured by the ratio of emission of acceptor (665 nm) to emission of donor (620 nm)×10,000.

Example 8

Identification of modulators of Topoisomerase Ubiquitination

An assay is provided that measures the ubiquitination of TOPIIα, via the activity of the E3 ligase RING1 as a complex with Bmi1. A commercially available ubiquitin-derivative can be employed as a fluorescence donor molecule, while a fluorophore-linked antibody is used as a fluorophore acceptor. Ubiquitination of a substrate protein was detected by the emission of the acceptor antibody (specifically bound to a substrate protein, via an antigen-antibody interaction) that was excited by the photon emitted from the donor (ubiquitin-linked) fluorophore, following donor excitation. Since ubiquitin-ligation brings both fluorophores within sufficient proximity for efficient energy-transfer, this reaction can be performed in homogeneous reaction conditions. The Europium Cryptate donor fluorophore fluoresces over a much greater time-period than most common fluorophores, thus enabling the reaction to be detected in a time-resolved format that eliminates interference from auto-fluorescing molecules that may be found in the environment.

Alternatively, the poly-ubiquitin chain can be used the means to induce proximity between the fluorophores. For this detection method, Biotin-Ubiquitin is added to the reaction and a Streptavidin-fluorophore acceptor molecule is substituted for the antibody described earlier.

The following reagents can be used in the assay:
1. E1 Ubiquitin Activating Enzyme (0.6 mg/ml, 6 µM, Proteologics, Israel)
2. UBCH5a (Cat# E2616 (50 µM), Boston Biochem Inc., MA, U.S.A.)
3. RING1/Bmi1 (Proteologics, Israel)
4. Ubiquitin 1 mg/ml solution in HPLC water
5. Ubiquitin-Cryptate—(cat# 61UBIKLB, CisBio, Mass., U.S.A.—(Optional) Biotin-Ubiquitin (or similar tag), if chain-elongation is to be detected.)

6. Anti-FLAG-XL665—(cat# 61FG2XLB, CisBio, Mass., U.S.A., or similar reagent corresponding to epitope tag in topoisomerase IIα

7. (Optional) Streptavidin-XL665—(cat# 61SAXLB, CisBio, Mass., U.S.A.—(or corresponding reagent), if chain-elongation is to be detected.)

8. Plasmid—pcDNA3.1, or equivalent (Invitrogen, CA, U.S.A.)

9. Ovalbumin 100 mg/ml solution in HPLC water

10. ATP—0.1M

11. MgCl$_2$—1M, Sigma

12. EDTA—0.5M, pH=8.

13. Tris 1M pH=7.6—Sigma Biotechnology Grade

14. Tween 20-6% solution in HPLC water

15. KF Buffer (0.8 M KF; 2 mg/ml BSA; and 200 mM phosphate buffer, pH=7.0)

16. DTT—0.1M solution in HPLC water

The following solutions are prepared: Dilution Buffer (25 mM Tris, pH=7.6; 0.006% Tween 20; 0.1 mM DTT; and 0.5 mg/ml Ovalbumin); 3× Reaction Mix (15 nME1 ubiquitin ligase activating enzyme (Proteologics, Israel); 6 mM ATP, 15 mM MgCl$_2$; 105 nM Ubiquitin-Cryptate; 840 nM Ubiquitin (or alternatively, a mix of Ubiquitin/Biotin-Ubiquitin is used if chain-elongation is to be detected); and 90 nM UBCH5a); 2×RING1/Bmi1/Topoisomerase Solution (0-100 nM of RING1/Bmi1 (Proteologics, Israel); 0.4 mg/ml plasmid; and 60 nM topoisomerase (Proteologics, Israel) in cold dilution buffer); Test Compound Solution (the test compound is diluted in 6% DMSO and 6% PEG-400); Antibody Solution (the antibody (such as the anti-FLAG-XL665 antibody) is diluted 1:50 in KF buffer). The reaction mix is prepared in cold dilution buffer and kept on ice. The test compound solution is kept at room temperature.

The reactions are performed in Costar PS black 96 well plates, and detected using a BMG RubyStar plate-reader (or equivalent).

Briefly, 5 µl of Test Compound solution is added to each well. 15 µl of 2×RING1/Bmi1/topoisomerase solution or Dilution Buffer (negative control) is also added to each well. The solutions are mixed by shaking, and are incubated at room temperature for 10 minutes. 10 µl of 3× Reaction Mix is added to each well, mixed by shaking and incubated at 37° C. for 1 hour. The reaction is stopped by adding 10 µl 0.5 M EDTA to each well. 30 µl of antibody solution is added to each well, mixed by shaking, and incubated for 2 hours at room temperature.

Reactions are read in the RubyStar plate-reader. The reaction mixtures are excited at 310 nm, and emissions are collected at 620 and 665 nm, with 50 µsec delay. Activity is measured by the ratio of emission of acceptor (665 nm) to emission of donor (620 nm)×10,000.

Example 9

Compound 1 and TOPII Drug Act Synergistically to Reduce Viability of A549 Cells

Figure 10:
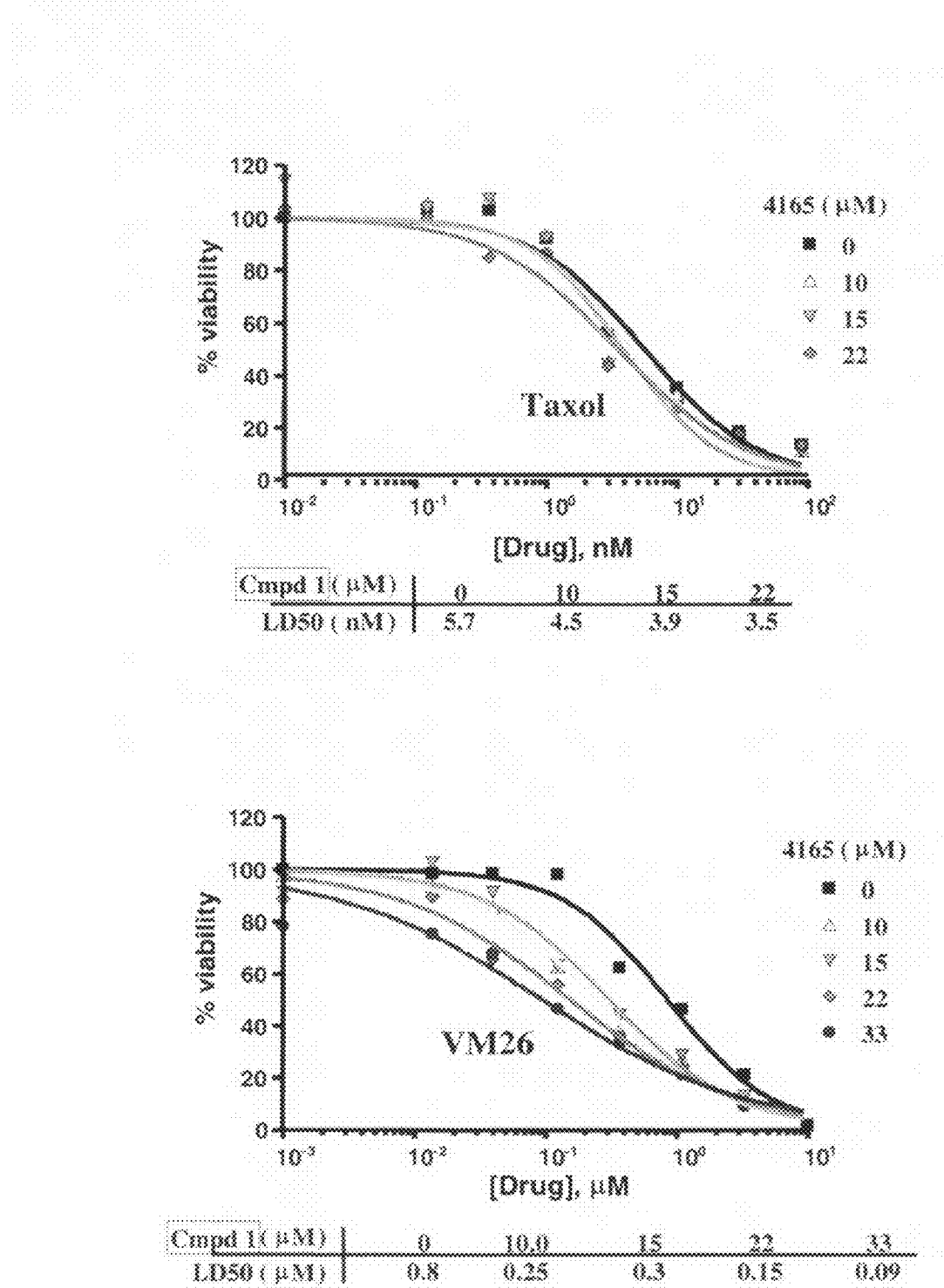
FIG. 10 shows the viability of A549 cells after treatment with compound 1 and TOPII drug (A) or non-TOPII drug (B).

A549 cells were cultured with DMEM and 10% FBS. The cells were treated with different concentrations of compound 1 with or without TOPII drug, VM26 (FIG. 10A) or non TOPII drug, Taxol® (paclitaxel) (Sigma, Israel) (FIG. 10B).

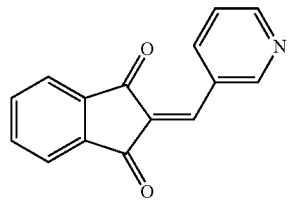

Compound 1, (cat# ST024375, TimTec Inc., DE, U.S.A.)

Seventy two hours post treatment, viability of the cells was tested using WST-1 reagent (Roche, Germany). compound 1 increased the potency of the VM26, an anti-TOPII drug by 10 fold, but has no synergistic effect with Taxol, a non-TOPII drug.

Example 10

Inhibition of TOPIIα Degradation by Compound 1 in HeLa Cells

HeLA cells were cultured with DMEM and 10% FBS. The cells were treated for 1 hr with solvent (50% DMSO, 50% PEG400) or 50 µM or 100 µM of compound 1, then for the indicated time with 100 µM of VM26.

Then the cells were harvested, alkaline extracted and treated with S7 DNAse (Roche, Germany) to release TOPII from the DNA. The amount of TOPIIα was assayed by immunoblot with specific antibodies (Santa-Cruz).

Figure 11:
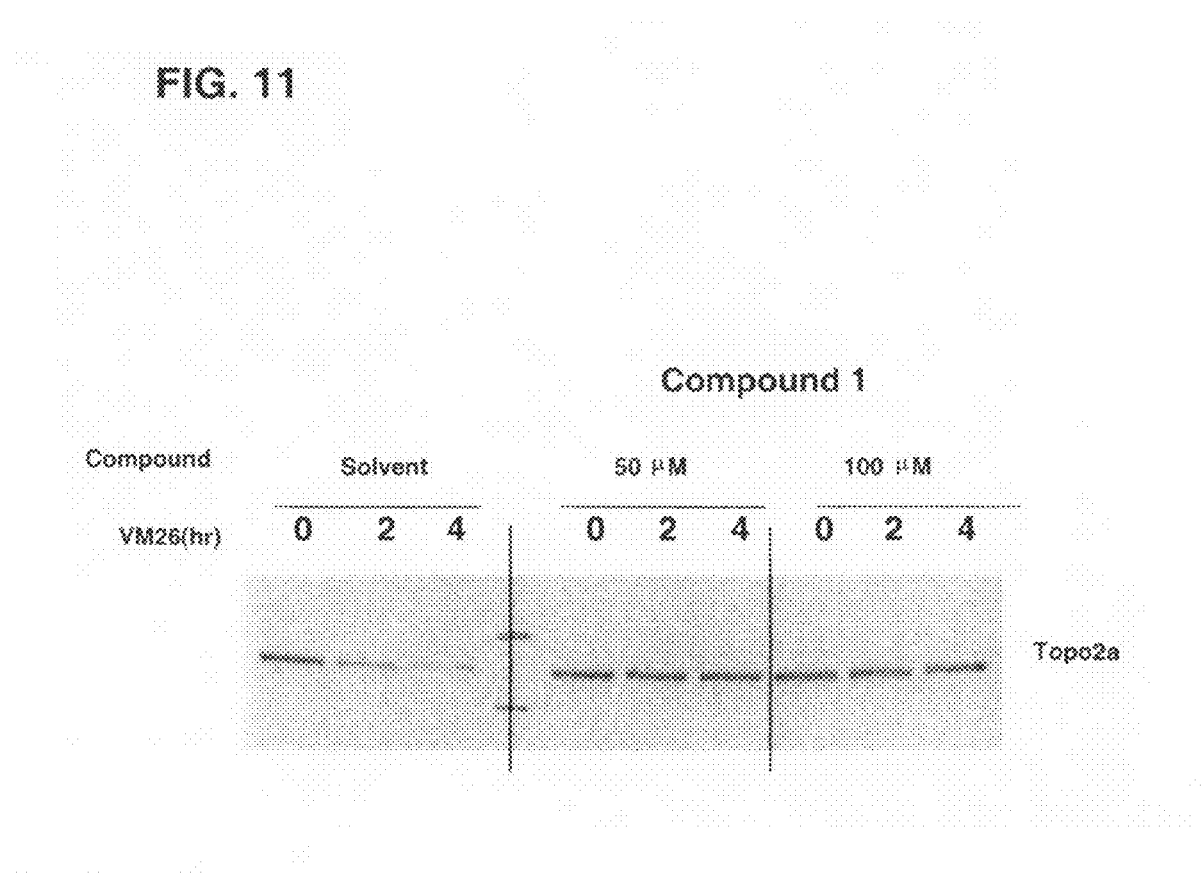
FIG. 11 shows inhibition of drug induced degradation of TOPIIα in HeLa cells by compound 1.

The compound 1 inhibits drug induced degradation of TOPIIα in HeLa cells (FIG. 11).

Example 11

Compound 1 Inhibits Ring1-Bmi1 Ubiquitination Activity in HeLa Cells

HeLa cells were cultured with DMEM and 10% FBS. The cells were transfected with a plasmid encoding HA-ubiquitin, Bmi1-Flag and RING1A unless otherwise is indicated using Lipofectamine-2000 transfection reagent ((Invitrogen, CA, U.S.A.).

Figure 12:
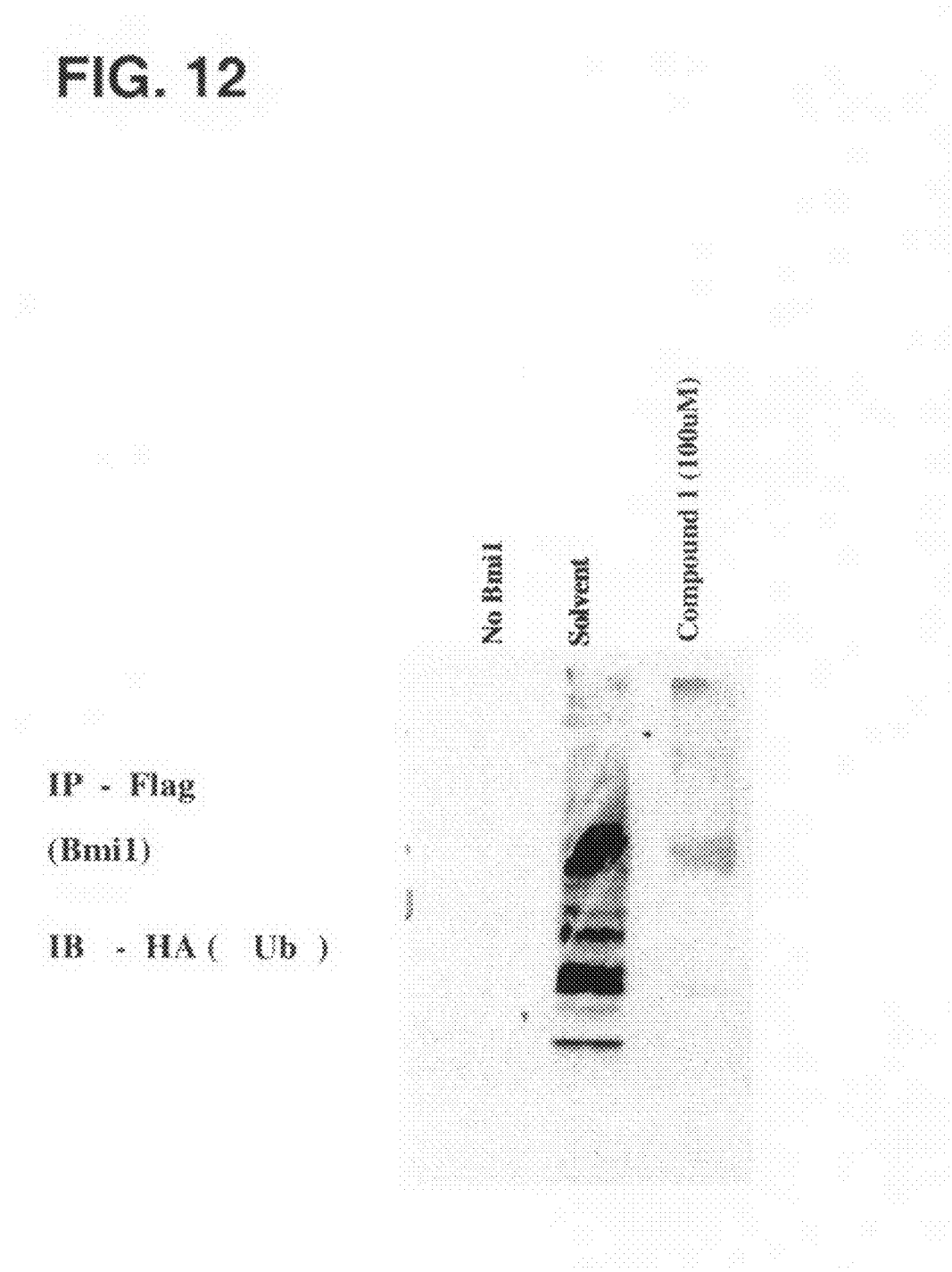
FIG. 12 shows inhibition of RING1-BMI1 ubiquitinisation activity in HeLa cells by compound 1.

Twenty-four hours post-transfection the cells were treated for 6 hours with solvent (50% DMSO, 50% PEG400) or 100 µM compound 1 (FIG. 12).

The cells were harvested; Flag-Bmi1 was immunoprecipitated with anti-Flag antibodies (Sigma Israel). The amount of ubiquitinated Bmi1 was assayed by immunoblot with anti-HA antibodies (Roche, Germany).

Compound 1 (FIG. 12) shows a significant inhibition in Ring1-Bmi-1 ubiquitination activity in HeLa cells.

Example 12

LD50 of Compound 1 in Various Cancer Cells.

Figure 13:
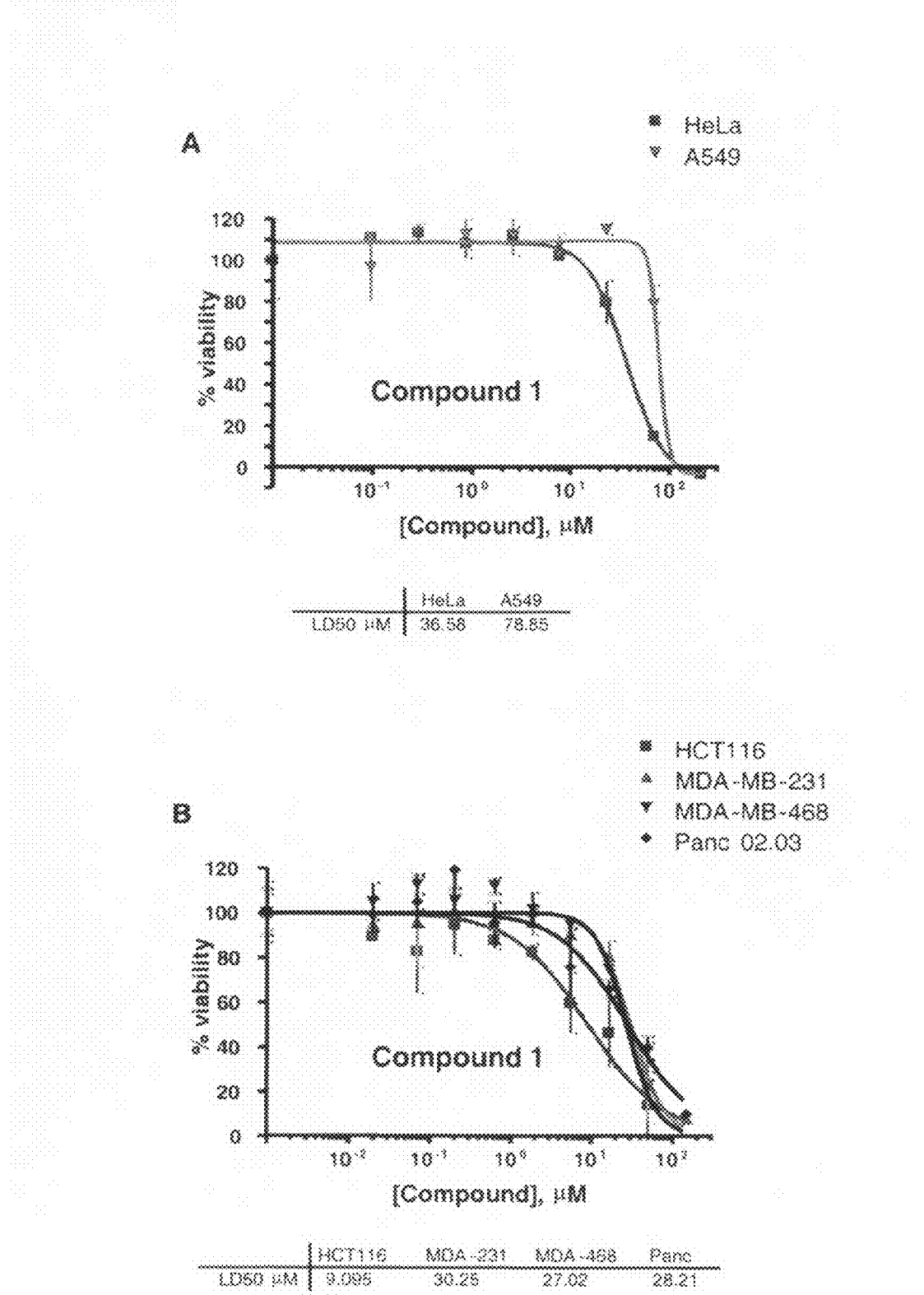
FIG. 13 shows LD50 of compound I in various cancer cells.

A549 cells (lung cancer) and HeLa cells (ovarian cancer) were cultured with DMEM and 10% FBS (FIG. 13A). MDA-MB-231 and MDA-MB-468 cells (breast cancer), HCT116 cells (colon cancer) and Panc02.03 cells (Pancreatic cancer) were cultured with RPMI and 10% FBS (FIG. 13B). The cells were treated with different concentrations of compound 1. Viability of the cells was tested seventy-two hours post treatment using WST-1 reagent (Roche, Germany). The LD50s were calculated using Prism software (Graphpad, Calif., U.S.A.).

DISCUSSION

The above examples show that silencing of Bmi1 or RING1A by siRNA inhibit VM26-induced (Teniposide, TOPII drug) TOPIIα degradation and increase its efficacy in toxicity assay. Bmi1 and RING1A are components of a protein complex termed Polycomb Repressive Complex 1 (PRC1). Wang et al (Wang, H., et al. 2004. Role of histone H2A ubiquitination in Polycomb silencing. Nature. 431:873-8.) identified a PRC1-like complex composed of Ring1A (RNF1), Ring1B (RNF2), Bmi1 and HPH2 that function as histones H2A ubiquitin ligase. Ring1A, Ring1B and Bmi1 all contain a RING domain, a characteristic of E3 ubiquitin-ligase domain. They tested each of these three proteins alone in H2A ubiquitination assay and found that only Ring1B possess H2A ubiquitination activity. Base on these results they reported the Ring1B is the ubiquitin ligase catalytic protein in this complex. Cao et al (Cao, R., et al. 2005. Role of Bmi-1 and Ring1A in H2A ubiquitylation and Hox gene silencing. Mol. Cell. 20:845-54.) showed that both Bmi1 and Ring1A increase the efficacy of Ring1B H2A ubiquitination activity.

Surprisingly, in contrast to the Wang et al article, we have found that Ring1A alone possess E3 ubiquitin ligase activity and we showed that Ring1A-Bmi1 recombinant protein complex ubiquitinates TOPIIα in cell free assay. These results together with the stabilization effect of Bmi1 and Ring1A siRNA on drug-induced TOPIIα degradation suggested that Ring1A-Bmi1 complex functions as TOPIIα ubiquitin ligase. Wei et al reported a similar observation about the effect of Bmi1 on Ring1B activity however they reported that Ring1A didn't affect this activity (Wei, J., et sl. 2006. Role of Bmi1 in H2A ubiquitylation and Hox gene silencing. J Biol. Chem. 281:22537-44.). Fang et al reported that the E3 ligase Ring1B is enriched on inactivated X chromosome (Xi) (Fang et al., 2004. Ring1b-mediated H2A ubiquitination associates with inactive X chromosomes and is involved in initiation of X inactivation. J Biol. Chem. 279:52812-5.). In another work de Napoles et al (de Napoles, M., et al., 2004. Polycomb group proteins Ring1A/B link ubiquitylation of histone H2A to heritable gene silencing and X inactivation. Dev Cell. 7:663-76.) found a link between Ring1A, Ring1B and H2A ubiquitination in embryonic mice stem cells. They reported an extensive depletion of global H2A ubiquitination in Ring1B null embryonic stem cells. On the inactive X chromosome, X1, H2A ubiquitination was maintained in Ring1A or Ring1B null cells but not in the Ring1A/Ring1B double knockout cells suggesting a redundancy in their activity. This work has failed short of shown that H2A on X1 is a direct ubiquitination target of Ring1A and Ring1B. Wei et al reported that although when Ring1B was dropped from the complex the H2a ubiquitination activity was decreased dramatically, a complex containing Bmi1, Ring1a and HPH2 showed some residual activity above the background level. This residual activity can explain the observations of de Napoles et al that on X1, H2A ubiquitination was maintained in Ring1A or Ring1B null cells but not in the Ring1A/Ring1B double knockout cells. PRC1 complex is also involved in stable X chromosome inactivation together with Cullin3/SPOP ubiquitin E3 ligase (Hernandez-Munoz, I., et al., 2005. Stable X chromosome inactivation involves the PRC1 Polycomb complex and requires histone MACROH2A1 and the CULLIN3/SPOP ubiquitin E3 ligase. Proc Natl Acad Sci USA. 102:7635-40.). The PRC1 complex is recruited to the X1 and Bmi1 binds to the Cullin3/SPOP ubiquitin E3 ligase and enable the ubiquitination of the H2A variants MacroH2A by the Cullin3/SPOP complex. These results raise the possibility that part of the effect of Ring1A and Ring1B on X1-H2a ubiquitination is mediated by other E3 ubiquitin ligase. Example 9 shows that the effect of silencing RING1A-Bmi1 by SiRNA, can be mimicked by small molecules that inhibit RING1A-Bmi1 ubiquitination activity.

compound 1 inhibits VM26-induced TOPIIα degradation and Ring1A-Bmi1 ubiquitination activity in HeLa cells. In agreement with the siRNA results, compound 1 showed synergistic effect with VM26, a TOPII-drug, to reduce viability of A549 lung cancer cells. These results further prove that targeting Bmi1 and Ring1A increases the efficacy of anti-TOPII drugs. The effect of compound 1 seems to be pathway dependent since it showed no synergy with Taxol® (paclitaxel), a cancer drug unrelated to TOPII.

It was shown that silencing of Bmi1 by RNAi promotes specific cell death of cancer cell-lines but not primary normal cells (Liu, L., et al., 2006. Loss of the human polycomb group protein BMI1 promotes cancer-specific cell death. Oncogene. 25:4370-5.). Silencing of Bmi1 by RNAi in biliary epithelial cells induced increased p161NK4a expression, decreased cell proliferation, and increased cellular senescence (Sasaki, M., et al., 2006. Decreased expression of Bmi1 is closely associated with cellular senescence in small bile ducts in primary biliary cirrhosis. Am J Pathol. 169:831-45.). Activation of the PcG pathway is mechanistically linked with highly malignant behavior of human prostate carcinoma cells and is essential for in vivo growth and metastasis of human prostate cancer. Silencing of Bmi1 in human adherent cultures of PC-3-derived prostate carcinoma cells treated with chemically modified degradation-resistant stable siRNAs developed less malignant and more slowly growing tumors (Berezovska, O. P., et al., 2006. Essential role for activation of the Polycomb group (PcG) protein chromatin silencing pathway in metastatic prostate cancer. Cell Cycle. 5:1886-901.).

In agreement with the role of Bmi1 in cancer development we have found that compound 1 kills cancer cells with LD50 range of 9-79 µM for various types of cancer cells.

What is claimed is:

1. A method for modulating cancer cell growth, comprising contacting the cancer cell with an effective amount of an inhibitor of an E3 ubiquitin ligase, and contacting the cell with an effective amount of a topoisomerase inhibitor such that the E3 ubiquitin ligase inhibitor and topoisomerase inhibitor modulate cell growth to a greater extent in comparison to a corresponding cell treated with the topoisomerase inhibitor alone, wherein the E3 ubiquitin ligase inhibitor is a compound having the structure:

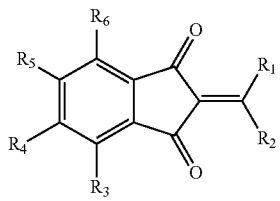

wherein $R_1$ and R2 are independently hydrogen, hydroxyl, alkyl, alkenyl, alkynyl, cycloalkyl, heterocyclic alkyl, aryl, heterocyclic aryl, acyl, alkoxy, amino, carboxyl, nitrile, sulfide, sulfone or sulfonamide, wherein each of the cycloalkyl, heteroclyclic alkyl, aryl, and heterocyclic aryl are optionally substituted with 1 to 3 groups selected from halogen, hydroxyl, amino, nitro, nitrile, sulfide, $C_1$-$C_6$ alkyl, halogenated $C_1$-$C_6$ alkyl, mono- or di-(C1-C6 alkyl) amine, C1-C6 alkoxy, or aryl or heterocyclic aryl; and $R_3$, $R_4$, $R_5$ and $R_6$, are each independently hydrogen, halogen, amine, amide, hydroperoxy, alkyl, alkoxy, alkenyl, acyl, carboxyl, carboxylate, aryl, heterocyclic aryl;

or a salt or an enantiomer of the compound.

2. The method of claim 1, wherein the cell is a human cell.

3. The method of claim 1, wherein the cancer cell is a cardiac, lung, gastrointestinal, genitourinary tract, liver, bone, nervous system, gynecological, hematologic, skin, or adrenal gland cancer cell.

4. The method of claim 1, wherein cell growth is inhibited.

5. The method of claim 1, wherein the topoisomerase inhibitor is selected from the group consisting of camptothecin, irinotecan, topotecan, doxorubicin, teniposide, etoposide, and analogs, derivatives, and combinations thereof.

6. The method of claim 1 wherein the inhibitor of E3 ubiquitin ligase is:

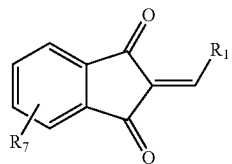

wherein $R_1$ is alkyl, acyl, amine, carboxylic acid, alkoxy, sulfone, sulfonamide aryl, or heterocyclic aryl, and $R_7$ is hydrogen, halogen, alkyl, acyl, carboxylic acid, alkoxy, aryl, or heterocyclic aryl, Or a salt or enantiomer of the compound.

7. The method of claim 6 wherein the inhibitor of E3 ubiquitin ligase is compound 1:

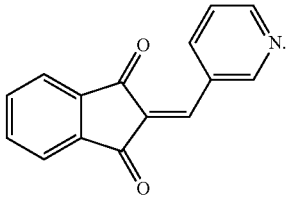

8. The method of claim 1 wherein $R_3$ is hydrogen.
9. The method of claim 1 wherein $R_4$ is hydrogen.
10. The method of claim 1 wherein $R_5$ is hydrogen.
11. The method of claim 1 wherein $R_6$ is hydrogen.
12. The method of claim 1 wherein $R_3$ and $R_6$ is hydrogen.

* * * * *